United States Patent
Klin et al.

(10) Patent No.: US 9,861,307 B2
(45) Date of Patent: Jan. 9, 2018

(54) SYSTEMS AND METHODS FOR DETECTING BLINK INHIBITION AS A MARKER OF ENGAGEMENT AND PERCEIVED STIMULUS SALIENCE

(71) Applicant: Children's Healthcare of Atlanta, Inc., Atlanta, GA (US)

(72) Inventors: Ami Klin, Atlanta, GA (US); Warren Jones, Decatur, GA (US); Sarah Shultz, Atlanta, GA (US)

(73) Assignee: Children's Healthcare of Atlanta, Inc., Atlanta, GA (US)

( * ) Notice: Subject to any disclaimer, the term of this patent is extended or adjusted under 35 U.S.C. 154(b) by 0 days.

(21) Appl. No.: 15/278,557

(22) Filed: Sep. 28, 2016

(65) Prior Publication Data
US 2017/0027493 A1    Feb. 2, 2017

Related U.S. Application Data

(62) Division of application No. 14/103,640, filed on Dec. 11, 2013, now Pat. No. 9,510,752.
(Continued)

(51) Int. Cl.
*A61B 3/14*    (2006.01)
*A61B 3/00*    (2006.01)
(Continued)

(52) U.S. Cl.
CPC ............ *A61B 5/165* (2013.01); *A61B 3/0025* (2013.01); *A61B 3/0041* (2013.01); *A61B 3/112* (2013.01);
(Continued)

(58) Field of Classification Search
USPC ................................................ 351/200–246
See application file for complete search history.

(56) References Cited

U.S. PATENT DOCUMENTS

| 4,889,422 A | 12/1989 | Pavlidis |
|---|---|---|
| 5,035,500 A | 7/1991 | Rorabaugh et al. |

(Continued)

FOREIGN PATENT DOCUMENTS

| DE | 3702528 A1 | 7/1987 |
|---|---|---|
| JP | 2006031475 A | 2/2006 |

(Continued)

OTHER PUBLICATIONS

Dieter Ebert, et al., Eye-Blink Rates and Depression Is the Antidepressant Effect of Sleep Deprivation Mediated by the Dopamine System, Neuropsychopharmacology 1996—vol. 15, No. 4 Published by Elsevier Science Inc. 332-339.
(Continued)

*Primary Examiner* — Mohammed Hasan
(74) *Attorney, Agent, or Firm* — Morris, Manning & Martin, LLP; Daniel E. Sineway, Esq.; R. Lee Strasburger, Jr., Esq.

(57) ABSTRACT

The present systems and methods provide a mechanism to assess viewer behavior, features of stimuli, and the interaction between viewer behavior and stimuli. The systems and methods described herein for quantifying blink response and blink inhibition provide moment-by-moments measurements of viewer engagement by measuring what is or is not engaging enough to warrant viewers' inhibition of blinking. The present disclosure describes measures of visual scanning, eye movements, blink data, and blink timing data to derive a measure of how engaged a person is with what he or she is looking at. Blink-related data as a measure of viewer engagement provides a mechanism for determining the most engaging spatial and temporal aspects of a stimulus.

66 Claims, 21 Drawing Sheets

Related U.S. Application Data

(60) Provisional application No. 61/735,865, filed on Dec. 11, 2012.

(51) Int. Cl.
    *A61B 5/16*     (2006.01)
    *A61B 3/113*     (2006.01)
    *A61B 3/11*     (2006.01)
    *A61B 5/11*     (2006.01)
    *A61B 5/00*     (2006.01)

(52) U.S. Cl.
    CPC ............ *A61B 3/113* (2013.01); *A61B 5/1103* (2013.01); *A61B 5/16* (2013.01); *A61B 5/168* (2013.01); *A61B 5/4088* (2013.01); *A61B 5/7275* (2013.01); *A61B 5/167* (2013.01)

(56) References Cited

U.S. PATENT DOCUMENTS

| | | |
|---|---|---|
| 5,150,716 A | 9/1992 | Franssen et al. |
| 5,384,593 A | 1/1995 | Gell, Jr. et al. |
| 5,880,812 A | 3/1999 | Solomon |
| 6,102,870 A | 8/2000 | Edwards |
| 6,116,736 A | 9/2000 | Stark et al. |
| 6,120,461 A | 9/2000 | Smyth |
| 6,231,187 B1 | 5/2001 | Munoz et al. |
| 6,364,486 B1 | 4/2002 | Ball et al. |
| 6,601,021 B2 | 7/2003 | Card et al. |
| 6,670,963 B2 | 12/2003 | Osberger |
| 6,712,468 B1 | 3/2004 | Edwards |
| 6,755,527 B1 | 6/2004 | Goldberg |
| 7,219,997 B2 | 5/2007 | Yokota et al. |
| 7,384,145 B2 | 6/2008 | Hetling et al. |
| 7,396,129 B2 | 7/2008 | Endrikhovski et al. |
| 7,819,818 B2 | 10/2010 | Ghajar |
| 8,371,693 B2 | 2/2013 | Ebisawa et al. |
| 8,668,337 B2 | 3/2014 | Waldorf et al. |
| 8,808,195 B2 | 8/2014 | Tseng et al. |
| 8,986,218 B2 | 3/2015 | De Lemos et al. |
| 2002/0154833 A1 | 10/2002 | Koch et al. |
| 2003/0158497 A1 | 8/2003 | Graham et al. |
| 2004/0015098 A1 | 1/2004 | Souvestre |
| 2005/0273017 A1 | 12/2005 | Gordon |
| 2006/0167670 A1 | 7/2006 | Deering |
| 2007/0066916 A1 | 3/2007 | Lemos |
| 2007/0265507 A1 | 11/2007 | De Lemos |
| 2008/0039698 A1 | 2/2008 | Burton |
| 2009/0073381 A1 | 3/2009 | Wheeler et al. |
| 2011/0172556 A1 | 7/2011 | Jones et al. |
| 2012/0078115 A1 | 3/2012 | Lonky |
| 2012/0094315 A1 | 4/2012 | Fryar-Williams et al. |
| 2012/0314045 A1 | 12/2012 | Billard et al. |
| 2013/0215390 A1 | 8/2013 | Johns et al. |
| 2013/0250244 A1 | 9/2013 | Yao et al. |
| 2014/0213930 A1 | 7/2014 | Mori et al. |

FOREIGN PATENT DOCUMENTS

| | | |
|---|---|---|
| JP | 2007502630 A | 2/2007 |
| WO | 2005018455 A1 | 3/2005 |
| WO | 2009097430 A1 | 8/2009 |
| WO | 2013035684 A1 | 3/2013 |
| WO | 2013102768 A1 | 7/2013 |

OTHER PUBLICATIONS

Manning, K. A. et al., "Different forms of blinks and their two-stage control", Experimental Brain Research, 1986, pp. 579-588, vol. 64, Springer-Verlag, 1986.

Michael Schiessel et al., "Eye tracking and its application in usability and media research", MMI-Interaktiv, Nr.6, Mar. 2003, p. 41-50.

Vanderwerf, Frans et al., "Eyelid Movements: Behavioral Studies of Blinking in Humans Under Different Stimulus Conditions", Journal of Neurophysiology, 2003, pp. 2784-2796, vol. 89, The American Physiological Society, 2003.

Nakano, Tamami et al., "Synchronization of spontaneous eyeblinks while viewing video stories", Proceedings of The Royal Society B, Accepted Jun. 18, 2009, pp. 1-10, The Royal Society, 2009.

O'Regan, J. Kevin et al., "Picture Changes During Blinks: Looking Without Seeing and Seeing Without Looking", Visual Cognition, 2000, pp. 191-211, vol. 7 (1/2/3), Psychology Press Ltd., 2000.

Ozonoff, S., et al. "Recurrence risk for autism spectrum disorders: a Baby Siblings Research Consortium study", Pediatrics, 2011, 128(3):e488-95.

Ponder, Eric et al., "On the Act of Blinking", Department of Physiology, Edinburgh University, received for publication Apr. 21, 1927, pp. 89-110, Exp Physiol, ep.physoc.org, downloaded Mar. 30, 2011.

Powers, Alice S. et al., "To blink or not to blink: inhibition and facilitation of reflex blinks", Experimental Brain Research, 1997, pp. 283-290, vol. 113, Spring-Verlag, 1997.

Powers, Alice Schade et al., "Conditioned Eyelid Movement Is not a Blink", Journal of Neurophysiol, 2010, pp. 641-647, vol. 103, The American Physiological Society, 2010.

Robert W. Reeder et al., "WebEyeMapper and WebLogger: Tools for Analyzing Eye Tracking Data Collected in Web-use Studies", 2000, 2 pages.

Volkmann, Frances C. et al., "Eyeblinks and Visual Suppression", Science, New Series, Feb. 22, 1980, pp. 900-902, vol. 207 No. 4433, American Association for the Advancement of Science, 1980.

Rosa Salva, O., Farroni, T., Regolin, L., Vallortigara, G., Johnson, M.H. "The evolution of social orienting: evidence from chicks (*Gallus gallus*) and human newborns", PLoS One, 2011.

Volkmann, Frances C., "Human Visual Suppression", Vision Research, 1986, pp. 1401-1416, vol. 26 No. 9, Pergamon Journals Ltd., 1986.

Shultz, Sarah, et al., "Inhibition of Eye Blinking Reveals Subjective Perceptions of Stimulus Salience," Proceedings of the National Academy of Sciences, vol. 108, No. 25, Dec. 27, 2011.

Siegle, Greg J. et al., "Blink before and after you think: Blinks occur prior to and following cognitive load indexed by pupillary responses", Psychophysiology, 2008, pp. 679-687, vol. 45, Society for Psychophysiological Research, USA, 2008.

Simion, F., Regolin, L., Bulf, H. "A predisposition for biological motion in the newborn baby", Proc Natl Acad Sci, 2008, USA. 105(2):809-13.

Simon Lessing et al., "II Cap—A New Environment for Eye Tracking Data Analysis", 2002, 48 pages.

Volkmann, Frances C., "Measurements of Visual Suppression During Opening, Closing and Blinking of the Eyes", Vision Research, 1982, pp. 991-996, vol. 22, Pergamon Press Ltd., 1982.

Speer LL, Cook AE, McMahon WM, Clark E. "Face processing in children with autism: effects of stimulus contents and type", Autism, 2007, 11(3): 265-77.

State, M.W., & Sestan, N. "Neuroscience: The emerging biology of autism spectrum disorders" Science, 2012, 227(6100):1301-3.

Steer, C.D., Golding, J., Bolton, P.F. "Traits contributing to the autistic spectrum" PLoS One, 2010, 5(9):e12633.

Stone, M. "Cross-validatory choice and assessment of statistical predictions", J Roy Stat Soc Ser, 1974, B. 36:111-147.

Tang, R. & Müller, H.G. "Pairwise curve synchronization for functional data", Biometrika, 2008, 95, 875-889.

Taylor, J. R. et al., "Spontaneous Blink Rates Correlate with Dopamine Levels in the Caudate Nucleus of MPTP-Treated Monkeys", Experimental Neurology, Accepted Mar. 24, 1999, pp. 214-220, vol. 158, Academic Press, 1999.

Abrahams, B.S. & Geschwind, D.H. "Advances in autism genetics: on the threshold of a new neurobiology", Nat Rev Genet, 2008, 9, 341-355.

Alfred L. Yarbus, "Eye Movement and Vision", 1967, p. 171-211.

Volkmar, F.R., Lord, C., Bailey, A., Schultz, R.T., Klin, A. "Autism and pervasive developmental disorders" J Child Psychol Psychiatry, 2004, 45, 1-36.

(56) References Cited

OTHER PUBLICATIONS

Averbuch-Heller, Lea, "Neurology of the eyelids", Current Opinion in Ophthalmology, 1997, pp. 27-34, Rapid Science Publishers, 1997.
Beedie, et al., Smooth Pursuit and Visual Scanpaths: Independence of Two Candidate Oculomotor Risk Markers for Schizophernia, The World Journal of Psychiatry, 2012.
Bentivoglio, Anna Rita et al., "Analysis of Blink Rate Patterns in Normal Subjects", Movement Disorders, 1997, pp. 1028-1034, vol. 12 No. 6, Movement Disorder Society, 1997.
Boris M. Velichkovsky et al., "New Technological Windows in Mind: There is More in Eyes and Brains for Human-Computer Interaction", CHI 96, 1996, p. 496-503.
Boris M. Velichkovsky et al., "Visual Fixations and Level of Attentional Processing", Eye Tracking Research & Applications Symposium, 2000, p. 79-85.
Vreugdenhil, Hestien et al., "Spontaneous Eye Blinking, a Measure of Dopaminergic Function, in Children With Acquired Immunodeficiency Syndrome", Yale University, Downloaded on Mar. 23, 2011, pp. 1025-1032, Arch Pediatr Adolesc Med., 1997.
Yao, F., Müller, H.G., Wang, J.L. "Functional data analysis for sparse longitudinal data" J Am Stat Assoc, 2005, 100(470):577-590.
Bour, L. J. et al., "Neurophysiological Aspects of Eye and Eyelid Movements During Blinking in Humans", Journal of Neurophysiology, 2000, pp. 166-176, vol. 83, The American Physiological Society, 2000.
Bristow, Davina et al., "Blinking Suppresses the Neural Response to Unchanging Retinal Stimulation", Current Biology, Jul. 26, 2005, pp. 1296-1300, vol. 15, Elsevier Ltd., 2005.
Bristow, Davina et al., "Two distinct neural effects of blinking on human visual processing", NeuroImage, 2005, pp. 136-145, vol. 27, Elsevier Inc., Jul. 2005.
Burchinal, M., Nelson, L., Poe, M. "Growth curve analysis: An introduction to various methods for analyzing longitudinal data" Best Practices in Quantitative Methods for Developmentalists, 2006.
Burr, David, "Vision: In the Blink of an Eye", Current Biology, 2005, p. R554-R556, vol. 15 No. 14, Elsevier Ltd., 2005.
Centers for Disease Control and Prevention, "Prevalence of autism spectrum disorders—Autism and Developmental Disabilities Monitoring Network", 14 Sites, United States, 2008, Surveillance Summaries, 2012, 1-19.
Yoon, Hyo Woon, "Neural correlates of eye blinking; improved by simultaneous fMRI and EOG measurement", Neuroscience Letters, 2005, pp. 26-30, vol. 381, Elsevier Ireland Ltd., 2005.
Chawarska, Katarzyna et al., "Autism spectrum disorder in the second year: stability and change in syndrome expression", The Journal of Child Psychology and Psychiatry, Feb. 2007, pp. 128-138, vol. 48 No. 2, Blackwell Publishing, 2007.
Constantino J.N., Todorov A., Hilton C., Law P., Zhang Y., Molloy E., Fitzgerald R., Geschwind D. "Autism recurrence in half siblings: strong support for genetic mechanisms of transmission in ASD" Mol Psychiatry, Feb. 2013, 8(2):137-8.
David S. Wooding, "Eye Movement of large population: II Deriving regions of interest, coverage, and similarity using fixation maps", Behavior Research Methods, Instruments, & Computers, Feb. 2002, p. 518-528.
Zwaigenbaum, Lonnie et al., "Behavioral manifestations of autism in the first year of life", International Journal of Developmental Neuroscience, May 5, 2004, pp. 143-152, vol. 23, Elsevier Ltd., 2004.
DeCasper, A.J., & Fifer, W.P. "Of human bonding: newborns prefer their mothers' voices" Science, May 1980, 208(4448):1174-6.
Evinger, C. et al., "Blinking and Associated Eye Movements in Humans, Guinea Pigs, and Rabbits", Blinking and Eye Movements, Journal of Neurophysiology, Aug. 1984, pp. 323-339, vol. 52 No. 2, The American Physiological Society, USA, 1984.
Evinger, C., "Eyelid Anatomy and the Pathophysiology of Blinking", Encyclopedia of the Eye, 2010, pp. 128-133, vol. 2, Elsevier, Ltd., Aug. 2010.

Evinger, Craig et al., "Eyelid Movements—Mechanisms and Normal Data", Investigative Ophthalmology & Visual Science, Feb. 1991, pp. 387-400, vol. 32 No. 2, Association for Research in Vision and Ophthalmology, 1991.
Evinger, Craig et al., "Not looking while leaping: the linkage of blinking and saccadic gave shifts", Exp Brain Res, 1994, pp. 337-344, vol. 100, Springer-Verlag, Feb. 1994.
Evinger, Craig et al., "Pattern of Extraocular muscle activation during reflex blinking", Experimental Brain Research, 1993, pp. 502-506, Springer-Verlag, Feb. 1993.
Evinger, Craig, "A Brain Stem Reflex in the Blink of an Eye", News in Physiological Sciences, Aug. 1995, pp. 147-153, vol. 10, Int. Union Physiol., 1995.
Fogarty, Christine et al., "Eye Movements and blinks: their relationship to higher cognitive processes", International Journal of Psychophysiology, 1989, pp. 35-42, vol. 8, Elsevier Science Publishers B.V. (Biomedical Division), 1989.
Gawne, Timothy J. et al., "Activity of Primate V1 Cortical Neurons During Blinks", Journal of Neurophysiology, 2000, pp. 2691-2694, vol. 84, The American Physiological Society, 2000.
Gawne, Timothy J. et al., "Responses of Primate Visual Cortical Neurons to Stimuli Presented by Flash, Saccade, Blink, and External Darkening", Journal of Neurophysiology, 2002, pp. 2178-2186, vol. 88, The American Physiological Society, 2002.
Grice, S.J., et al. "Neural correlates of eye-gaze detection in young children with autism", Cortex, 2005, 21, 342-353.
Gruart, A. et al., "Kinematics of Spontaneous, Reflex, and Conditioned Eyelid Movements in the Alert Cat", Journal of Neurophysiology, Jul. 1995, pp. 226-248, vol. 74 No. 1, The American Physiological Society, 1995, U.S.A.
Haith, M.M. et al., "Eye Contact and Face Scanning in Early Infancy", Science, Nov. 25, 1977, pp. 853-855, vol. 198 No. 4319, American Association for the Advancement of Science, 1977.
Hall, P., Müller, H.G., Yao, F. "Estimation of functional derivatives", Ann Stat, 2009, 37, 3307-3329.
Hall, Sir Arthur, "The Origin and Purposes of Blinking", The British Journal of Ophthalmology—Communication, Sep. 1945, pp. 445-467, Downloaded from bjo.bmj.com on Mar. 23, 2011, Published by group.bmj.com.
Hari, R. et al., "Visual stability during eyeblinks", Nature, Jan. 13, 1994, pp. 121-122, vol. 367, Nature Publishing Group, 1994.
Horn, G., Nicol, A.U., Brown, M.W. "Tracking memory's trace", Proc Natl Acad Sci, 2001, USA, 98(9):5282-5287.
International Search Report and Written opinion received in International Application PCT/US2013/074487 filed on Dec. 11, 2013.
Johnson, M. "Functional brain development in humans", Nat Rev Neurosci, 2001, 2, 475-483.
Johnson, M.H. "Subcortical face processing", Nat Rev Neurosci, 2005, 6(10):766-774.
Jones, W. Carr, K., Klin, A. "Absence of preferential looking to the eyes of approaching adults predicts level of social disability in 2-year-olds with autism spectrum disorder", Arch Gen Psych, 2008, 65(8):946-954.
Jones, Warren et al., "Heterogeneity and Homogeneity Across the Autism Spectrum: The Role of Development", Clinical Implications of Basic Research, Journal of the American Academy of Child Adolescent Psychiatry, May 2009, pp. 471-473, vol. 48 No. 5, Am.
Jutkiewicz, Emily M. et al., "Effects of Dopamine D1 Ligands on Eye Blinking in Monkeys: Efficacy, Antagonism, and D1/D2 Interactions", The Journal of Pharmacology and Experimental Therapeutics, 2004, pp. 1008-1015, vol. 311, The American Society for Pha.
Kanner, L. "Autistic disturbances of affective contact", Nerv Child, 1943, 2, 217-250.
Karson, Craig N., "Spontaneous Eye-Blinking Rates and Dopaminergic Systems", Brain, 1983, pp. 643-653, vol. 106, Downloaded from brain.oxfordjournals.org at Yale University, Mar. 23, 2011.
Klin, A., Lin, D.J., Gorrindo, P., Ramsay, G., Jones, W. "Two-year-olds with autism fail to orient towards human biological motion but attend instead to non-social, physical contingencies", Nature, 2009, 459, 257-261.

(56) References Cited

OTHER PUBLICATIONS

Klin, A., Saulnier, C.A., Sparrow, S.S., Cicchetti, D.V., Volkmar, F.R., & Lord, C. "Social and communication abilities and disabilities in higher functioning individuals with austism spectrum disorders", J. Autism Dev Disord, 2007, 37(4):748-59.

Klin, Ami et al., "The enactive mind, or from actions to cognition: lessons from autism", Autism: mind and brain, The Royal Society, Feb. 28, 2003, pp. 345-460, vol. 358 No. 1430, The Royal Society, 2003.

Liu, B., Müller, H.G. "Estimating derivatives for samples of sparsely observed functions, with application to online auction dynamics", J Am Stat Assoc, 2008, 104(486):704-717.

Keisuke Matsumura et al., Precise and Real-Time Pupil Position Estimation in Color Camera Face Images Based on Near-infrared Pupil Detection Method, The Journal of the Institute of Image Information and Television Engineers, Japan, vol. 65, No. 12, 2011.

Jeki, et al., Prepulse inhibition of acoustic startle response in mild cognitive impairment and mild dementia of Alzheimer type, Psychiatry and Clinical Neurosciences, Feb. 2006, pp. 55-62.

EXEMPLARY BLINK AND/OR EYE MONITORING SYSTEM

EXEMPLARY DATA INDICATIVE OF OCULAR RESPONSE (EYE MOVEMENT)

EXEMPLARY DISPLAY OF PORTIONS OF A DYNAMIC VISUAL STIMULUS

EXEMPLARY GENERATION OF DISPLAY OF DISTRIBUTION OF VISUAL RESOURCES

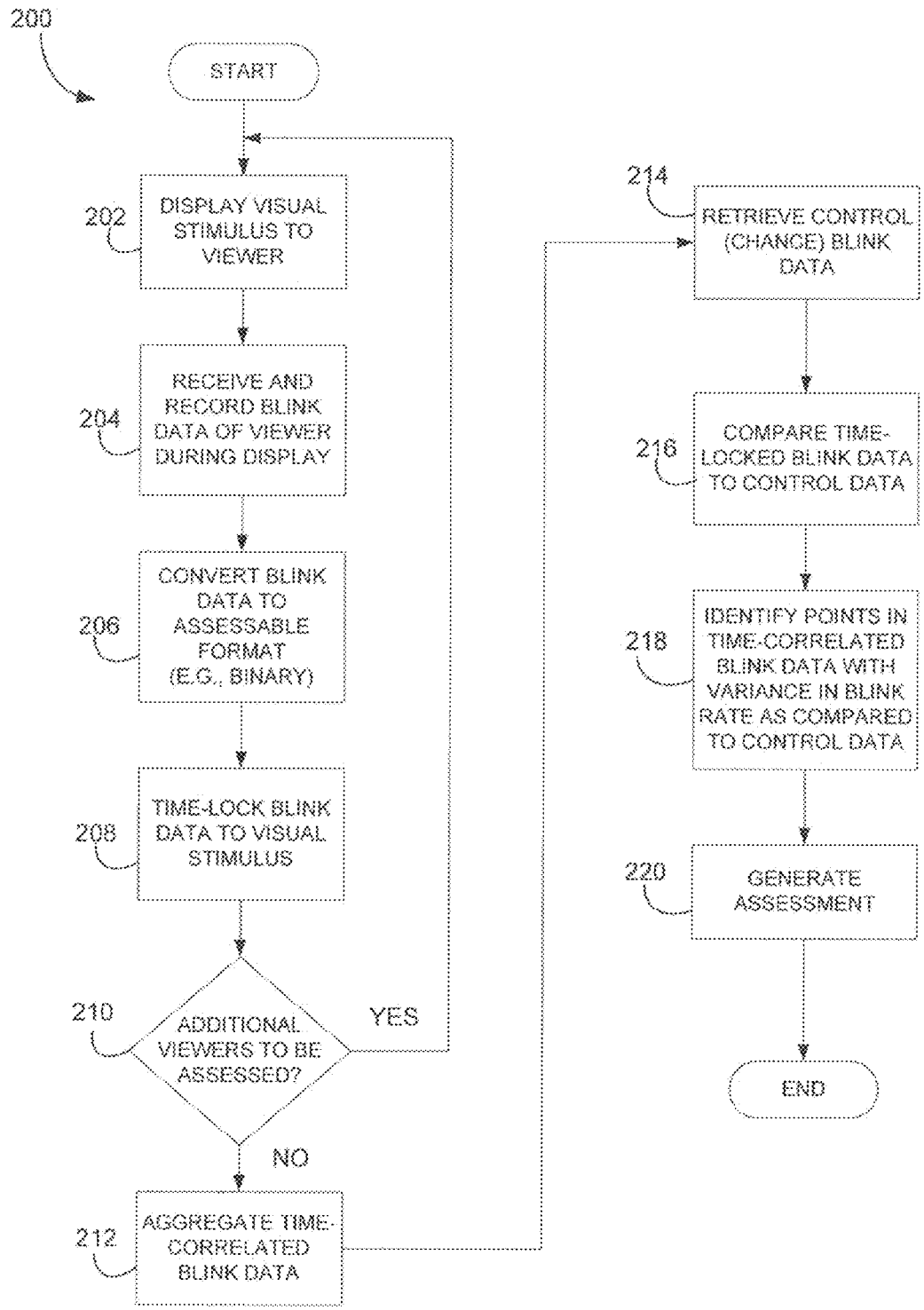
FIG. 2 – EXEMPLARY DATA COLLECTION AND ASSESSMENT PROCESS

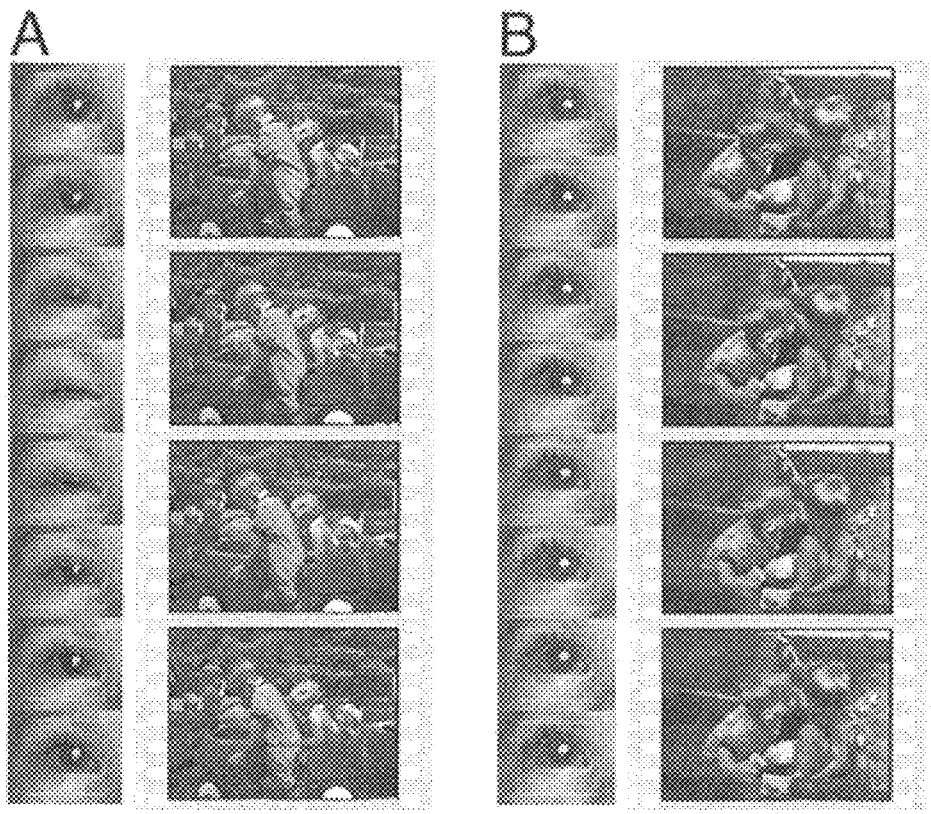
*FIG. 3* — BLINKING AND STATISTICALLY SIGNIFICANT BLINK INHIBITION WHILE VIEWING A VISUAL STIMULUS

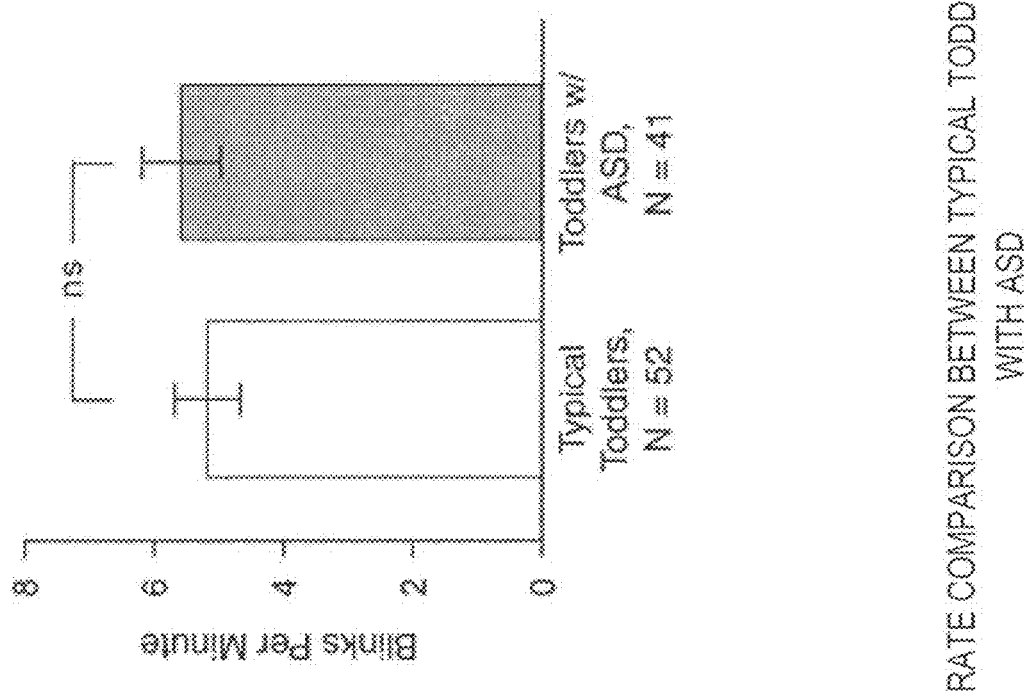
FIG. 4 – BLINK RATE COMPARISON BETWEEN TYPICAL TODDLERS AND TODDLERS WITH ASD

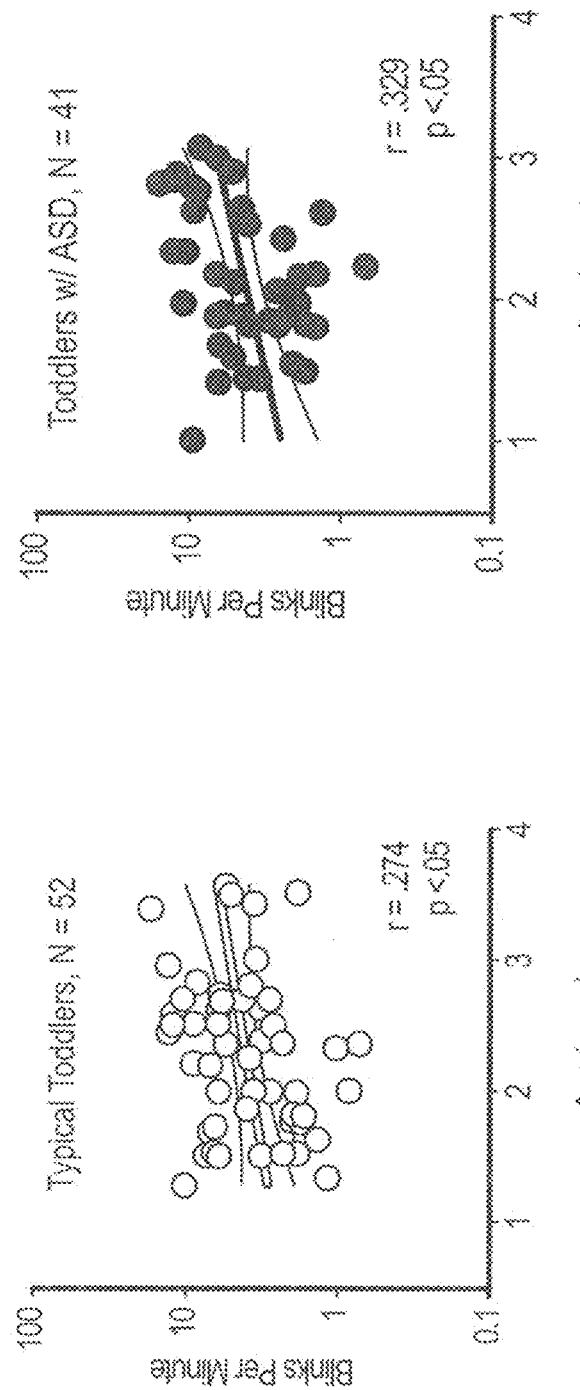

TASK DEPENDENT MODULATION OF BLINKING

COMPARISON OF TASK DEPENDENT MODULATION OF BLINKING BETWEEN TWO DIFFERENT VIEWER GROUPS

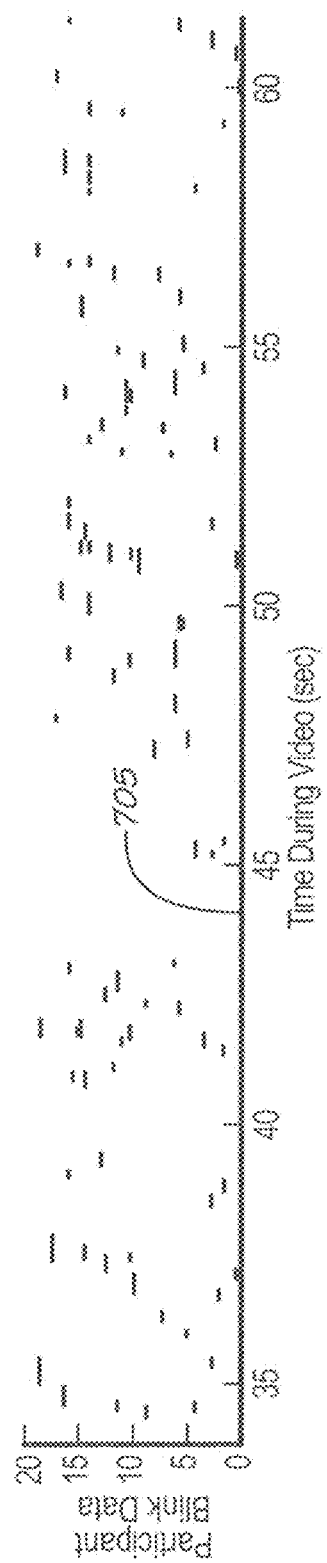
FIG. 7A
FIG. 7B

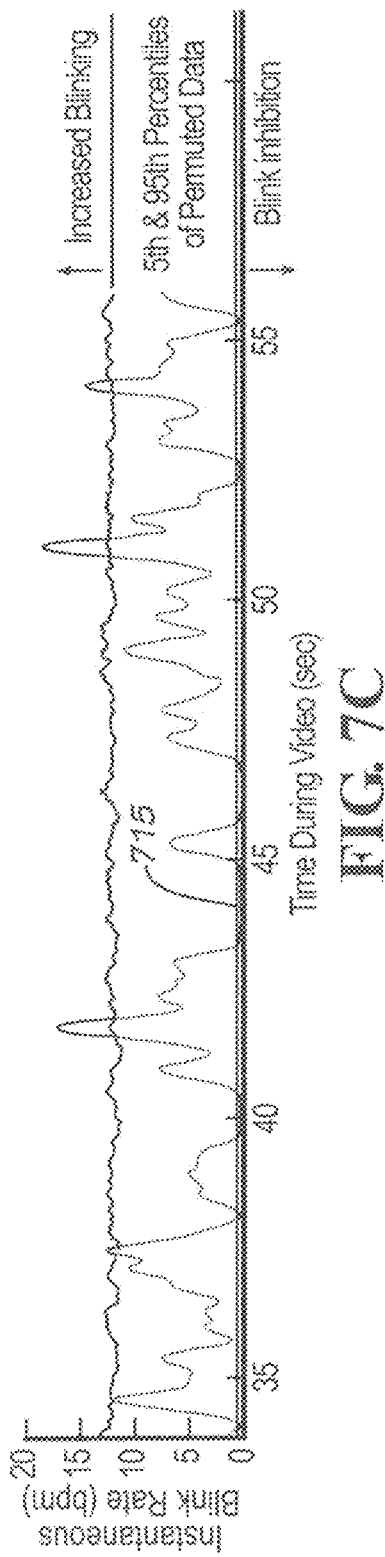
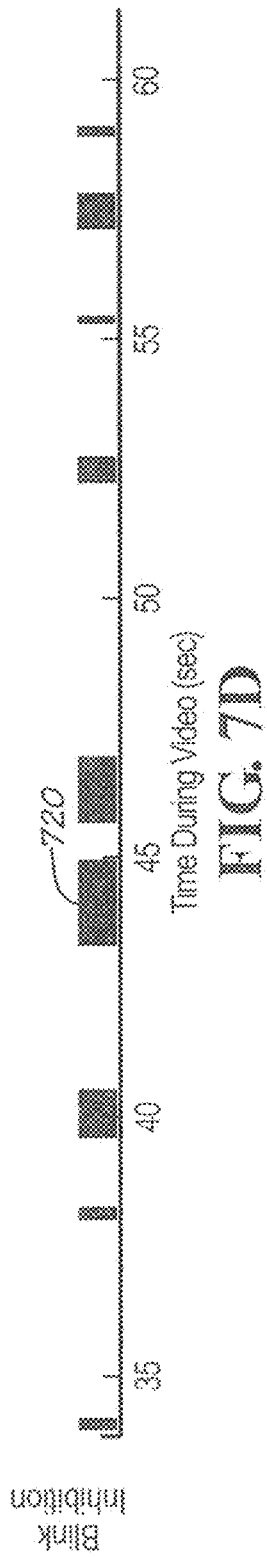
FIG. 7C
FIG. 7D
BLINK INHIBITION DATA CORRELATED WITH TIME

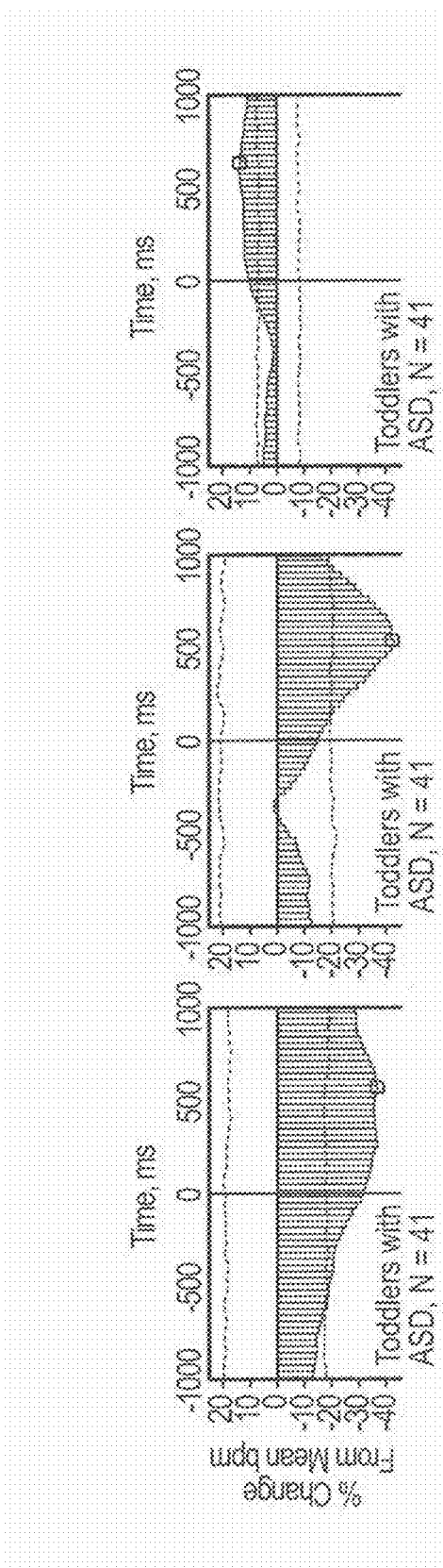
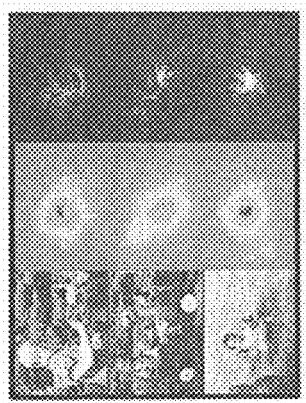
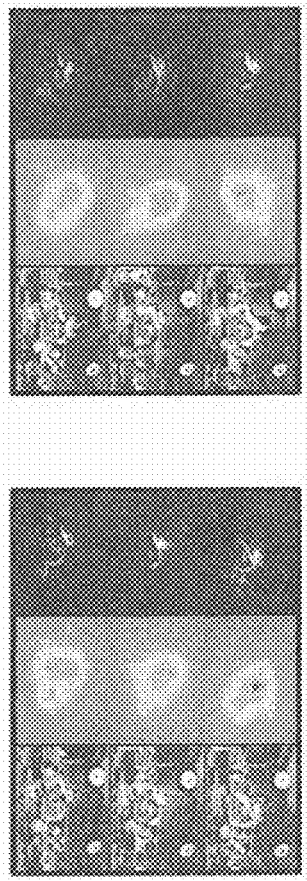
FIG. 8G  FIG. 8H  FIG. 8I
FIG. 8J  FIG. 8K  FIG. 8L

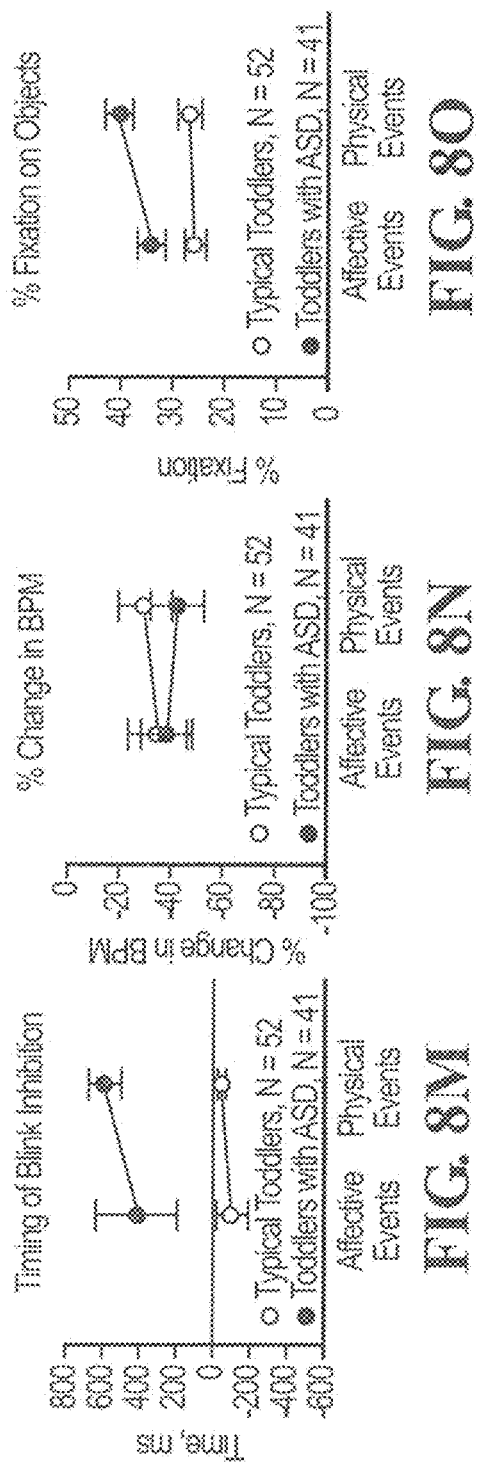
BLINK INHIBITION COMPARISON CORRELATED WITH VARIOUS EVENTS

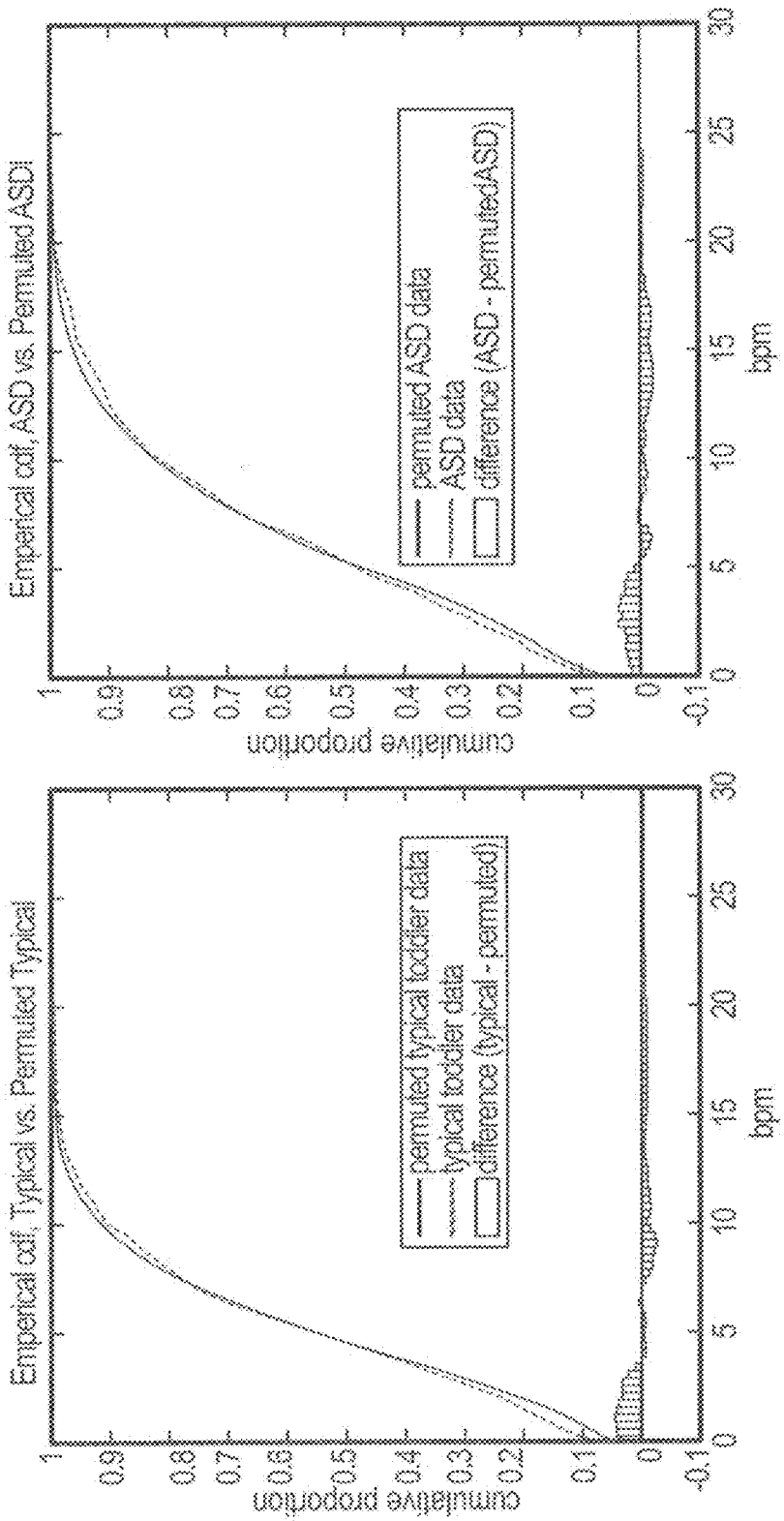

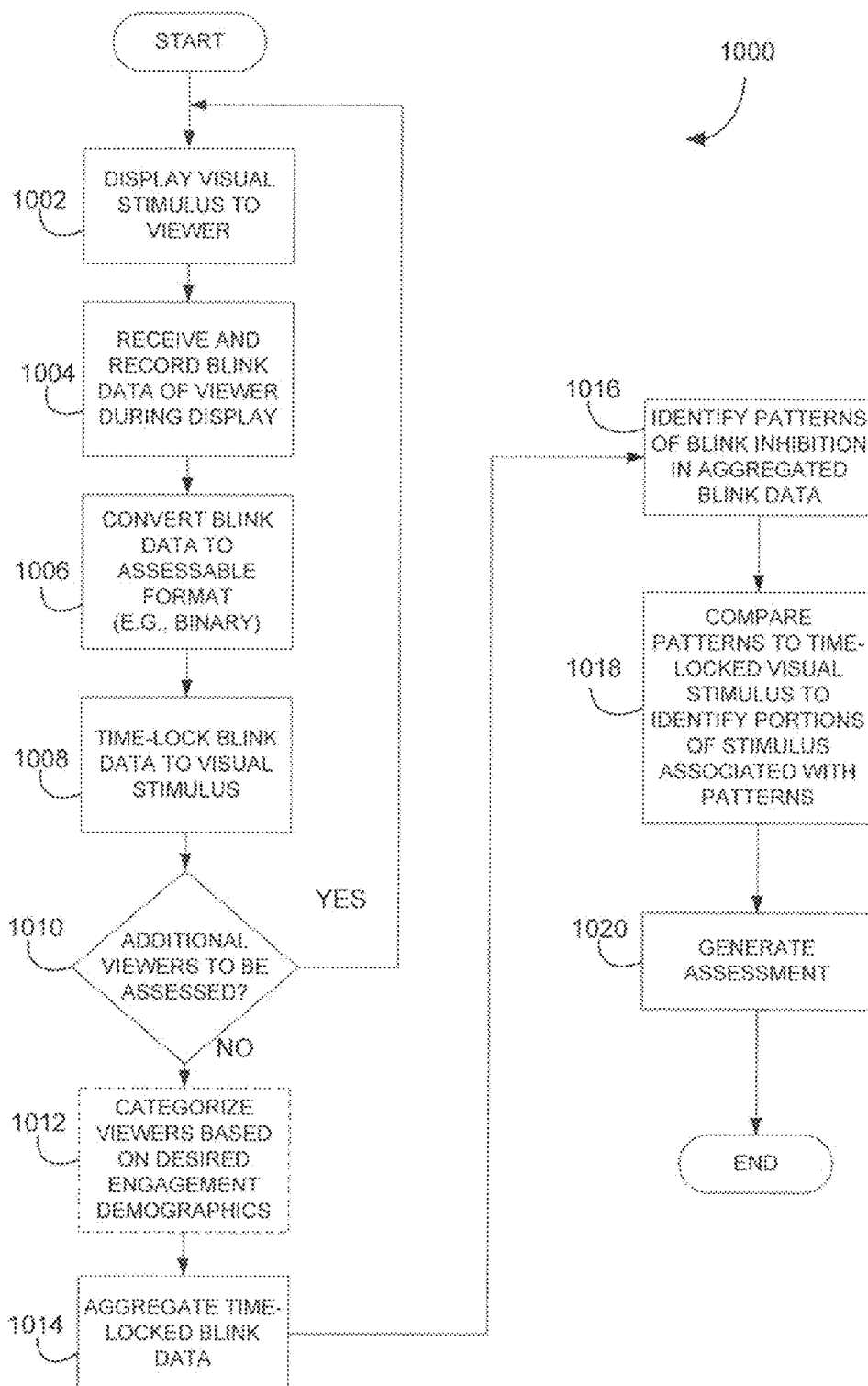
FIG. 10 – EXEMPLARY PROCESS FOR DETERMINING ENGAGEMENT ACTIVITY

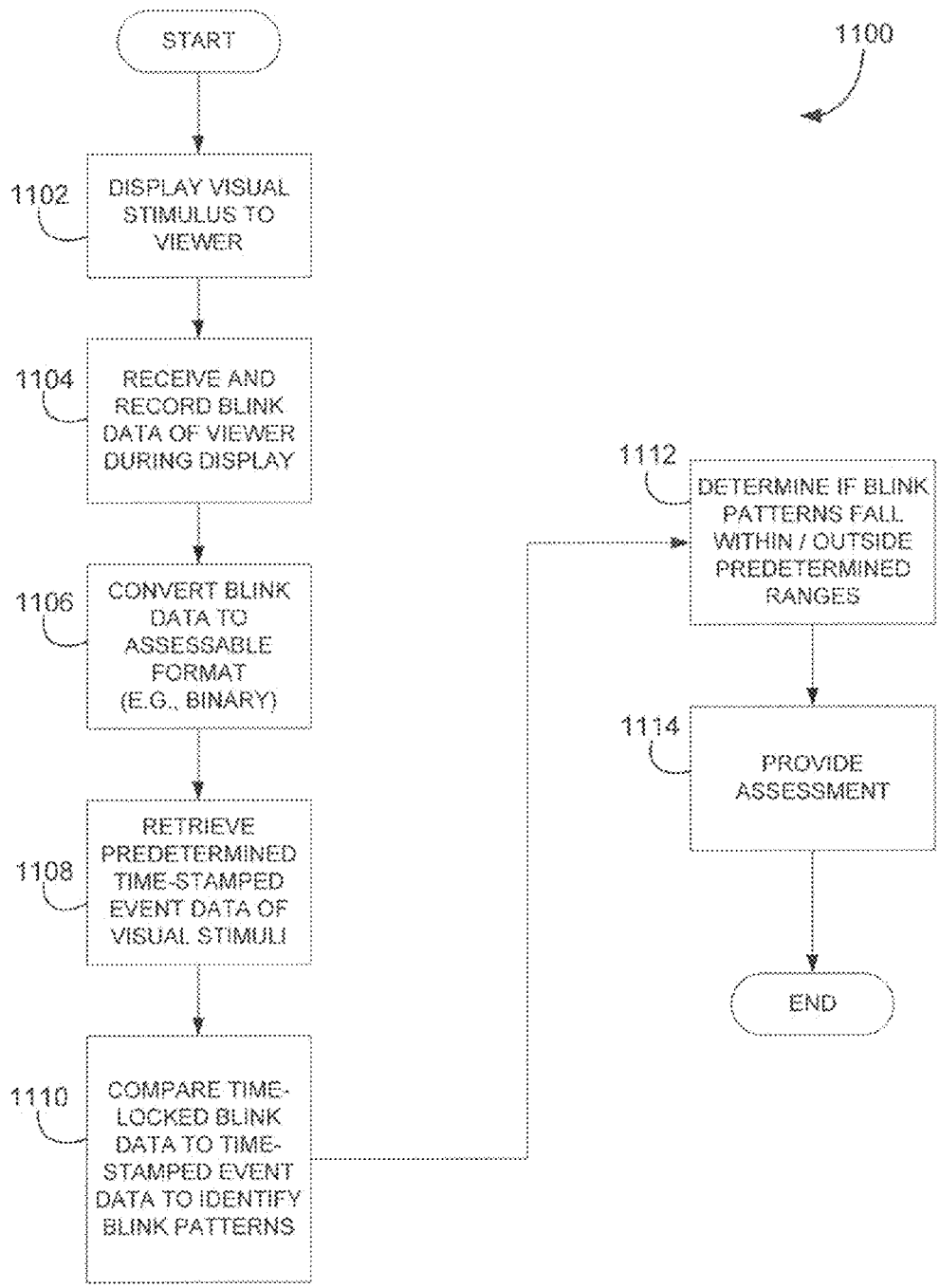
*FIG. 11* – EXEMPLARY PROCESS FOR ASSESSING/CATEGORIZING VIEWER

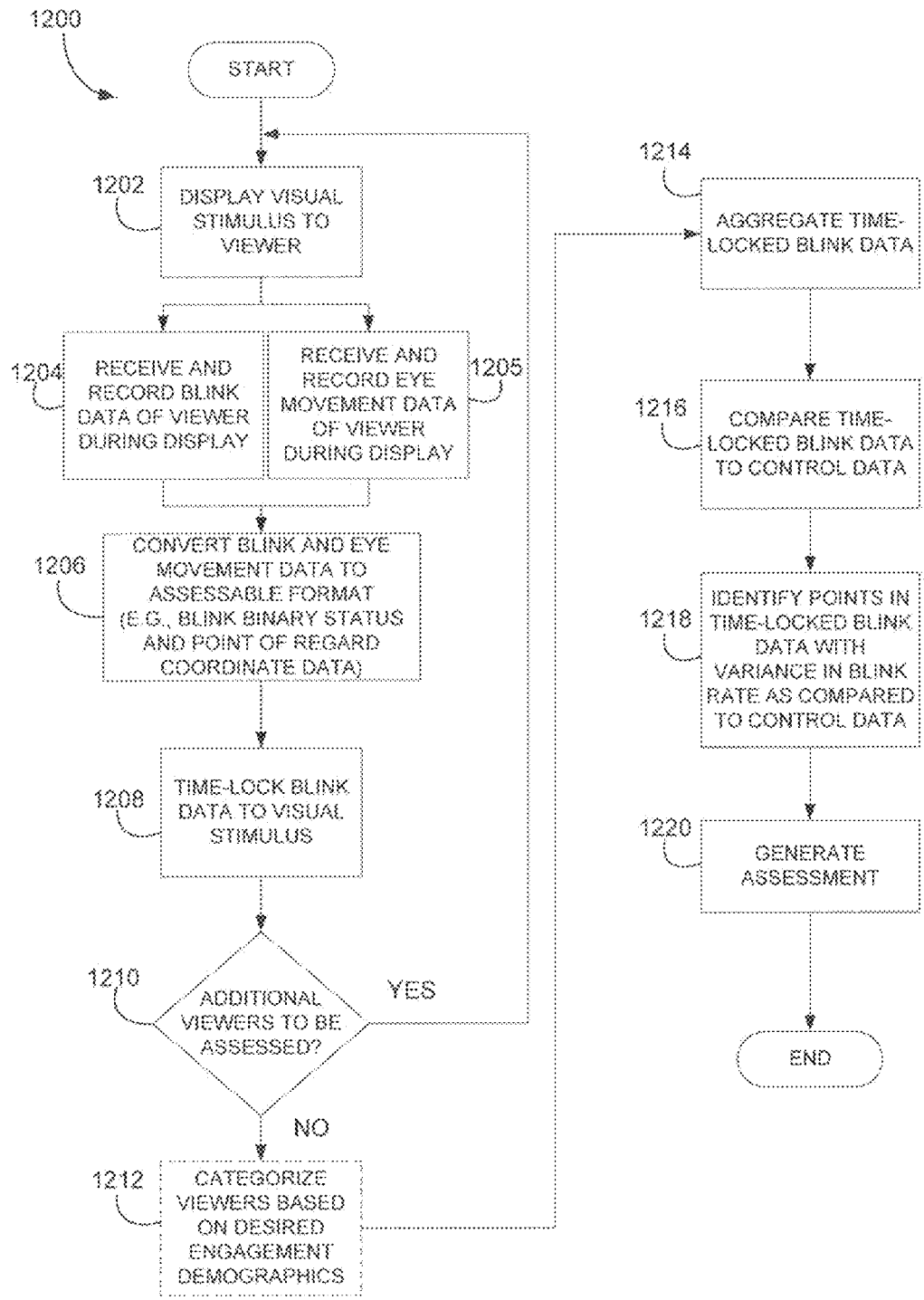
FIG. 12 – EXEMPLARY BLINK AND EYE MOVEMENT DATA COLLECTION AND ASSESSMENT PROCESS

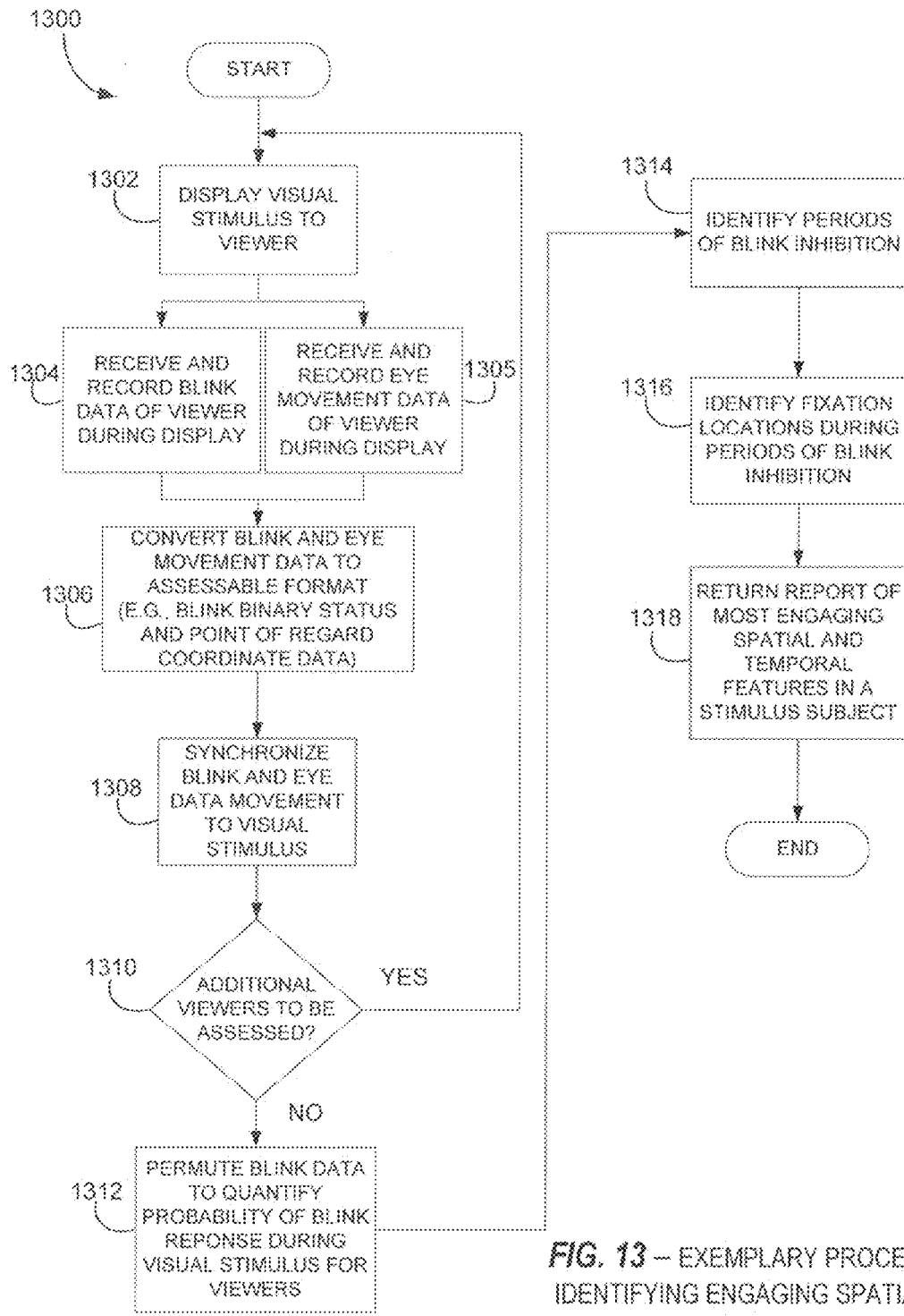

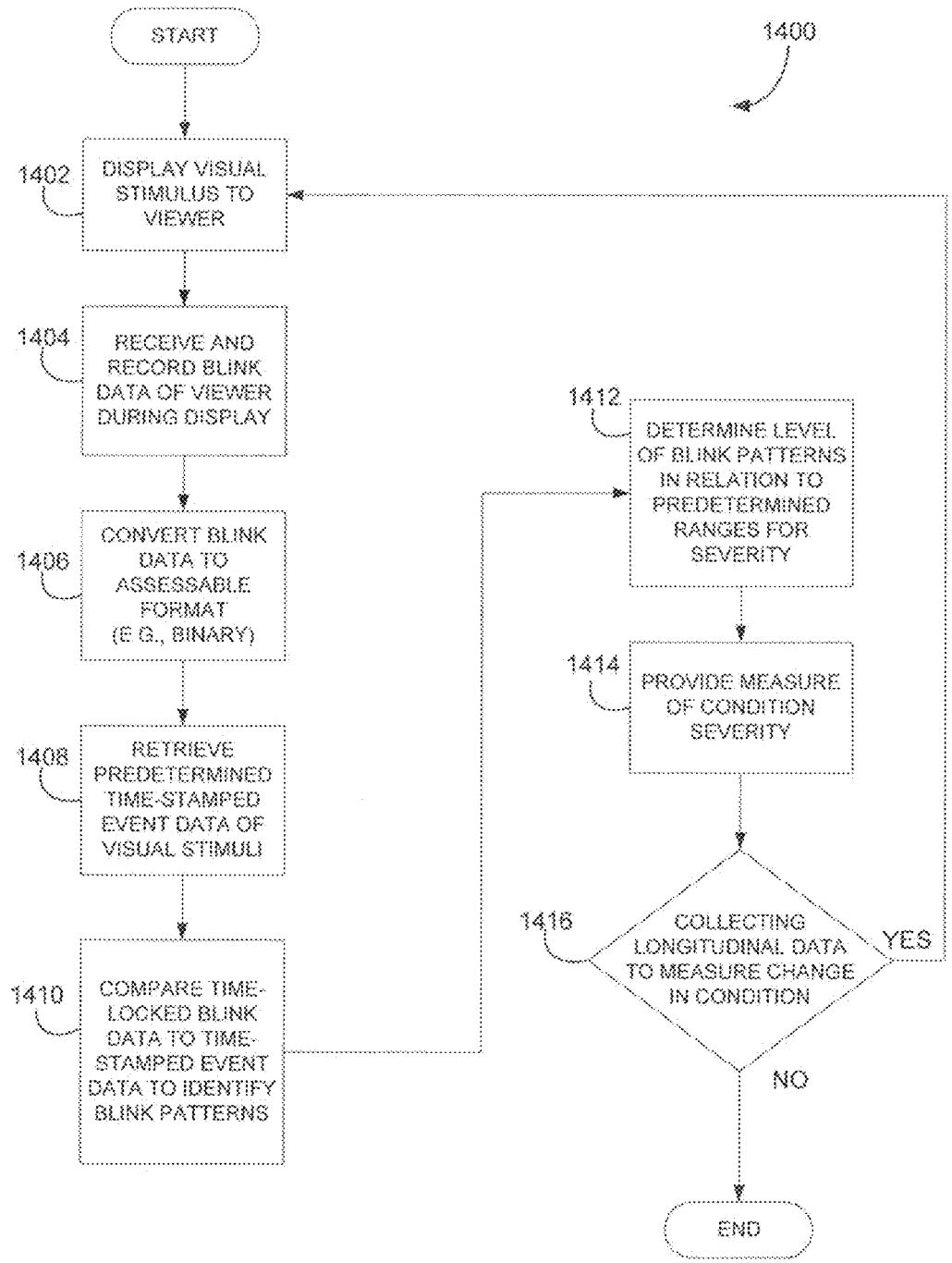
FIG. 14 – EXEMPLARY PATIENT/CONDITION ASSESSMENT PROCESS

SYSTEMS AND METHODS FOR DETECTING BLINK INHIBITION AS A MARKER OF ENGAGEMENT AND PERCEIVED STIMULUS SALIENCE

CROSS REFERENCE TO RELATED APPLICATION

This application is a divisional of, and claims benefit of and priority under 35 U.S.C. 120 to U.S. Non-Provisional application Ser. No. 14/103,640, filed Dec. 11, 2013, and entitled "SYSTEMS AND METHODS FOR DETECTING BLINK INHIBITION AS A MARKER OF ENGAGEMENT AND PERCEIVED STIMULUS SALIENCE", and claims benefit under 35 U.S.C. §119(e) of U.S. Provisional Patent Application No. 61/735,865, filed Dec. 11, 2012, and entitled "Blink Inhibition as a Marker of Engagement and Perceived Stimulus Salience", both of which are incorporated herein by reference as if set forth herein in their entireties.

STATEMENT REGARDING FEDERALLY-SPONSORED RESEARCH

This invention was made with government support under grant number P50-MH081756-01 awarded by the National Institute of Mental Health. The government has certain rights in the invention.

TECHNICAL FIELD

The present systems and methods relate generally to measuring eye-blink behavior and eye-blink inhibition as indicators of viewer engagement with visual or auditory stimuli, and relate more particularly to utilizing the timing of blink inhibition during natural viewing to: assess viewer engagement with stimuli, to assess viewer perception of the relative salience of stimuli, to assess a stimulus's power to engage specific viewers or groups of viewers, to identify the most engaging spatial and temporal features of a stimulus, and to categorize or rate viewers as a function of their engagement with a given stimulus for demographic or diagnostic purposes.

BACKGROUND

When we blink, the flow of visual information between the world and one's retina is temporarily interrupted. In that instant of blinking, visual stimulation from the external world is lost for 150-400 milliseconds (ms or msecs). As a result, the average adult in the course of a single waking day will spend approximately 44 minutes with his or her eyelids closed missing visual information. During those moments, a variety of neural systems encompassing movement of the oculomotor muscles, activity in supplementary and frontal eye fields, and widespread activity in visual, parietal, and prefrontal cortical areas work together to suppress the actual visual signal of an occluding eyelid. These systems create the illusion of perceptual continuity, but if new visual information is presented in that instant of blinking, it will be missed.

During the collection of eye movement data, eye-blinks have been traditionally regarded as noise or artifact data and are generally deemed useless. However, blinking also relates to cognitive states beyond mere physiological function. It is also generally known that individuals remain largely unaware of their blinking, although blinking may be generally related to both explicit and implicit attentional pauses in task content.

Identification and quantification of a person's engagement with a visual stimulus can provide insights for many different fields. In cognitive and behavioral testing, as for autism, attention deficit hyperactivity disorder (ADHD), developmental disabilities, and other cognitive conditions, measuring how engaged a viewer is with specific types of visual (or audible) content can provide a biomarker of disease/disorder state, disease/disorder progression, and/or treatment response. For instance, children with developmental disabilities, which affect 1 in 10 within the general population, show delayed acquisition of speech and language skills. A measure of a child's engagement with speech and language cues (e.g., level of engagement with talking faces or communication gestures, which are precursors to language acquisition) can aid in the diagnostic identification of a child with developmental disabilities at a much earlier age than diagnosis of such disabilities conventionally occurs.

In another example, in commercial industries, one of the main concerns for many marketing companies is measuring the effectiveness of various marketing campaigns. Traditional approaches to determining visual marketing campaign effectiveness include conducting consumer surveys and questionnaires, analyzing sales numbers, social media "buzz", etc. However, marketing companies would benefit from having a mechanism to determine directly from viewer behavior, without secondhand reporting or surveys, the effectiveness of a visual marketing campaign by measuring the level of a viewer's or group of viewers' engagement to that marketing campaign during test trials prior to releasing the campaign or during the actual campaign. In another example, developers of visual teaching aids may also benefit from having a measure of student engagement levels during the development phase of the teaching aids. Other industries could benefit from measuring indicators of engagement to visual stimuli, such as video game developers, flying and driving simulator developers, etc.

Therefore, there is a long-felt but otherwise unresolved need for a system and method that can assess and measure viewer engagement. Moreover, there is a need to measure engagement with certain visual and/or auditory stimuli, such as movies, television shows, marketing campaigns, print ads, web pages, emergency videos, teaching aids, even physical environments and objects, etc. in order to enable optimization thereof. Further, there is an additional need for a system and method to use measures of viewer engagement as biomarkers for assessing disease/disorder state, disease/disorder progression, and/or treatment response in conditions such as autism, ADHD, schizophrenia, bipolar disorder, depression, and others that effect engagement with circumscribed content.

BRIEF SUMMARY OF THE DISCLOSURE

Briefly described, and according to one embodiment, aspects of the present disclosure generally relate to systems and methods for assessing blink inhibition and blink response as indicators of engagement with visual stimuli. In particular, aspects of the present disclosure relate to utilizing the timing of blink inhibition during natural viewing and in response to visual stimuli to accomplish the following: to assess viewer engagement with stimuli, to assess viewer perception of the relative salience of stimuli, to assess a stimulus's power to engage specific viewers or groups of viewers, to identify the most engaging spatial and temporal features of a stimulus, and to categorize or rate viewers as a function of their engagement with a given stimulus for demographic or diagnostic purposes. According to one embodiment, the present systems and methods provide a tool for assessing viewer engagement on the basis of blink rate and the timing of blinking and blink inhibition, during natural viewing. In one embodiment, the present systems and methods provide a tool for quantifying viewers' moment-by-moment engagement with visual content and the degree to which viewer engagement varies dynamically. In another embodiment, the present systems and methods provide a tool for quantifying listener's moment-by-moment engagement with auditory content and the degree to which listener engagement varies dramatically as it relates to blink inhibition and blink data.

Further, and according to one embodiment, the present systems and methods provide a mechanism for determining, by a "data mining" approach, the most engaging spatial and temporal features of a stimulus on the basis of time-varying viewer engagement. Further aspects of the present disclosure relate to the way in which these measures of engagement can be combined with eye-tracking point-of-gaze data to measure the specific parts of a stimulus that a viewer is fixating upon at moments of greater or lesser engagement (e.g., fixation locations).

Further aspects of the present disclosure relate to systems and methods for assessing disease/disorder state (e.g., presence/absence of a condition), disease/disorder state progression, and/or treatment response in conditions for example but not limited to autism spectrum disorders (ASD), ADHD, schizophrenia, bipolar disorder, depression, post-traumatic stress disorder (PTSD), and others that effect engagement with circumscribed content or engagement. In one embodiment, in research leading to the present disclosure, toddlers with ASD, unlike typically developing comparison children, demonstrate markedly delayed blink inhibition in relation to specific visual events. The present systems and methods indicate that typical toddlers, relative to the same visual events, inhibit their blinking earlier than toddlers with ASD. This difference provides evidence of intact cognitive processes in typical toddlers and evidence that those processes are disrupted in toddlers with ASD: typical toddlers inhibited their blinking in active anticipation of the unfolding of salient social events, while toddlers with ASD did not. These measurements provide information that can be used for assessing diagnostic status as well as for measuring severity of symptomatology. Related embodiments can be deployed to measure the level of engagement of, for example, recovering drug addicts with environmental triggers (for example, images of alcohol, drugs, or locations in which such substances are typically procured or consumed) in order to assess risk for relapse.

In one embodiment, the present disclosure describes a method for displaying visual engagement over time of a plurality of individuals with respect to a dynamic visual stimulus. This embodiment includes the steps receiving blink data indicative of blink responses to the dynamic visual stimulus for each of the plurality of individuals; retrieving control blink data from a database; comparing the received blink data to the control blink data to identify one or more differences between the received blink data and the control blink data; and generating a display of the one or more differences between the received blink data and the control blink data. In certain embodiments, the above steps may be executed via software on a processor.

In one aspect, the method comprises blink data for each of the plurality of individuals corresponding to a rate of change for each individual's pupil size and/or eyelid closure.

In one aspect, the method comprises the step of converting the blink data to binary format for comparison purposes and the step of aggregating the blink data for the plurality of individuals. In certain embodiments, the above steps may be executed via software on a processor.

In one aspect, the method includes control blink data comprising an average blink rate for the plurality of individuals when no dynamic visual stimulus is present, and/or an average blink rate for a group of individuals different from the plurality of individuals when no dynamic visual stimulus is present, and/or a probability distribution of average blink rates for the plurality of individuals as obtained by permuting the blink data of the plurality of individuals.

In one aspect, the method comprises the step of permuting the data of the plurality of individuals comprises circular shifting with respect to an original timing of blink data collection and/or the step of permuting the data of the plurality of individuals comprises randomizing an order of blinks and inter-blink intervals for each individual.

In one aspect, the method comprises one or more differences between the received blink data and the control blink data comprising one or more of the following: increased blink rate as compared to the control blink data, decreased blink rate as compared to the control blink data, lack of blinks within a predetermined time period, exceeding a predetermined number of blinks within a predetermined time period and/or one or more differences between the received blink data and the control blink data is a marker of a developmental, cognitive, or mental disorder.

In one aspect, the method comprises the step of using the display of the one or more differences between the received blink data and the control blink data in connection with a diagnosis of an individual, wherein the above step may be executed via software on a processor.

In one aspect, the method further comprises the steps of synchronizing the received blink data with the dynamic visual stimulus; and/or generating a display of the one or more differences between the received blink data and the control blink data in connection with the dynamic visual stimulus. In certain embodiments, the above steps can be executed via software on a processor.

In one embodiment, the present disclosure includes a method for displaying visual engagement over time of a plurality of individuals with respect to a stimulus. This embodiment includes the steps of receiving blink data indicative of blink responses to the stimulus for each of the plurality of individuals; retrieving control blink data from a database; comparing the received blink data to the control blink data to identify one or more differences between the received blink data and the control blink data; and generating a display of the one or more differences between the received blink data and the control blink data. In certain embodiments, the above steps can be executed via software on a processor.

In one aspect, the method includes the steps of: receiving eye-movement data indicative of eye movements for each of the plurality of individuals with respect to the stimulus; determining from the eye-movement data a plurality of fixation locations with respect to the stimulus for the plurality of individuals; synchronizing the plurality of fixation locations and the received blink data with the stimulus; and generating a display of the plurality of fixation locations at one or more time points corresponding to the one or more differences between the received blink data and the control blink data.

In one aspect, the method includes the display of the plurality of fixation locations comprising a three-dimensional display, wherein two of the dimensions correspond to the plurality of fixation locations for each of the plurality of individuals and one of the dimensions corresponds to time. Further, in one aspect, the method includes the plurality of fixation locations corresponding to each of the plurality of individual's eye fixation locations with respect to one or more frames of the stimulus. In another aspect, the method includes the plurality of fixation locations corresponding to point-of-gaze coordinate data for each of the plurality of individuals with respect to the stimulus. In one aspect, the method further includes the display of the plurality of fixation locations comprising a three-dimensional scanpath. According to one aspect, the method includes wherein the step of synchronizing comprising time-locking or time-correlating the plurality of fixation locations to the received blink data.

In one aspect, the method comprises the blink data for each of the plurality of individuals corresponding to a rate of change for each individual's pupil size. According to one aspect, the method includes the blink data for each of the plurality of individuals corresponding to eyelid closure.

In one aspect, the method further comprises the steps of converting the blink data to binary format for comparison purposes; and/or converting the eye-movement data to coordinate data for comparison purposes; and/or aggregating the blink data and the eye-movement data for the plurality of individuals. In certain embodiments, the above steps can be executed via software on a processor.

In one aspect, the method includes the control blink data comprising an average blink rate for the plurality of individuals when no stimulus is present. According to one aspect, the method includes the control blink data comprising an average blink rate for a group of individuals different from the plurality of individuals when no stimulus is present. In one aspect, the control blink data comprising a probability distribution of average blink rates for the plurality of individuals as obtained by permuting the blink data of the plurality of individuals.

In another aspect, the method includes the steps of permuting the data of the plurality of individuals comprises circular shifting with respect to an original timing of blink data collection and/or permuting the data of the plurality of individuals comprises randomizing an order of blinks and inter-blink intervals for each individual, wherein the steps may be executed via software on a processor.

In one aspect, the method includes one or more differences between the received blink data and the control blink data comprising one or more of the following: increased blink rate as compared to the control blink data, decreased blink rate as compared to the control blink data, lack of blinks within a predetermined time period, exceeding a predetermined number of blinks within a predetermined time period.

In one aspect, the method comprises the one or more differences between the received blink data and the control blink data as a marker of a developmental, cognitive, or mental disorder.

In one aspect, the method includes the steps of using the display of the plurality of fixation locations at one or more time points corresponding to the one or more differences between the received blink data and the control blink data in connection with a diagnosis of an individual; and/or synchronizing on the processor, the received blink data with the stimulus; and/or generating, a display of the one or more differences between the received blink data and the control blink data in connection with the stimulus. In certain embodiments, the above steps can be executed via software on a processor.

In one aspect, the method includes the stimulus as an auditory stimulus, a dynamic visual stimulus, and/or a static visual stimulus. In another aspect, the method includes the stimulus comprising one or more of the following: a dynamic stimulus, a dynamic visual stimulus, a pre-recorded visual stimulus, a pre-recorded audio stimulus, a pre-recorded audiovisual stimulus, a live visual stimulus, a live audio stimulus, a live audiovisual stimulus, a two-dimensional stimulus, or a three-dimensional stimulus.

In one embodiment, the present disclosure comprises a method for determining a measure of engagement by an individual with respect to a dynamic visual stimulus. This embodiment includes the steps of: receiving blink data indicative of the individual's blink responses to the dynamic visual stimulus; synchronizing the blink data with the dynamic visual stimulus; identifying a pattern of blink inhibition in the synchronized blink data; and comparing the pattern of blink inhibition in the synchronized blink data with the dynamic visual stimulus to identify a portion of the dynamic visual stimulus contemporaneous with the pattern of blink inhibition, whereby the pattern of blink inhibition indicates a marker of engagement by the individual with the contemporaneous portion of the dynamic visual stimulus. In certain embodiments, the above steps can be executed via software on a processor.

In one aspect, the method includes the dynamic visual stimulus comprising one or more of the following: a pre-recorded visual stimulus, a pre-recorded audiovisual stimulus, a live visual stimulus, a live audiovisual stimulus, a two-dimensional stimulus, or a three-dimensional stimulus.

In one aspect, the method includes the pattern of blink inhibition comprising a mean blink rate for the individual during the dynamic visual stimulus. In one aspect, the method further includes the pattern of blink inhibition comprising a comparison between the individual's blink data and a chance probability of blinking associated with the individual. In another aspect, the method includes the pattern of blink inhibition comprising a moment-by-moment blink rate for the individual. According to one aspect, the method includes the pattern of blink inhibition comprising a measure of an instantaneous blink rate for the individual at a certain time point as compared to a mean blink rate for the individual. In one aspect, the method includes the pattern of blink inhibition comprising a measure of an instantaneous blink rate for the individual at a certain time point as compared to a mean blink rate for a control group.

In one aspect, the method includes the pattern of blink inhibition comprising a measure of an instantaneous blink rate for the individual as compared to measure of variance in a mean blink rate for the individual. In another aspect, the method includes the pattern of blink inhibition comprising a measure of the synchronized blink data as compared with control blink data. In one aspect, the method includes the pattern of blink inhibition comprising a measure of blink inhibition relative to an event in the dynamic visual stimulus.

In one aspect, the contemporaneous portion of the dynamic visual stimulus comprises the entirety of the dynamic visual stimulus. According to one aspect, the method includes the event in the dynamic visual stimulus comprising a physical event or an affective event.

In one aspect, the method includes the step of categorizing the individual into one or more predefined categories based on the marker of engagement. In another aspect, the marker of engagement relates to a salient portion of the dynamic visual stimulus.

According to one aspect, the method includes the step of synchronizing, which comprises time-locking or time-correlating the blink data with the dynamic visual stimulus.

In one aspect, the method includes the blink data corresponding to a rate of change of the individual's pupil size. In another aspect, the method includes the blink data corresponding to eyelid closure of the individual.

In another aspect, the method further comprises the steps of converting, via software executing on the processor, the blink data to binary format for comparison purposes and/or categorizing, via software executing on the processor, the blink data according to predetermined demographic parameters.

In one embodiment, the present disclosure comprises a method for determining a measure of engagement by an individual with respect to a stimulus. This embodiment includes the steps of: receiving blink data indicative of the individual's blink responses to the stimulus; synchronizing the received blink data with the stimulus; identifying, via software executing on the processor, a pattern of blink inhibition in the synchronized blink data; and comparing the pattern of blink inhibition in the synchronized blink data with the stimulus to identify a portion of the stimulus contemporaneous with the pattern of blink inhibition, whereby the pattern of blink inhibition indicates a marker of engagement by the individual with the contemporaneous portion of the stimulus. In certain embodiments, the above steps can be performed via software on a processor.

In one aspect, the method includes the steps of receiving eye-movement data indicative of the individual's eye movements with respect to the stimulus; determining from the eye-movement data a plurality of fixation locations with respect to the stimulus; and comparing the plurality of fixation locations with the stimulus at the contemporaneous portion of the stimulus. In certain embodiments, the above steps can be executed via software on a processor.

According to one aspect, the method includes the pattern of blink inhibition comprising a comparison between the individual's blink data and a chance probability of blinking associated with the individual. In one aspect, the method includes the stimulus comprising one or more of the following: a dynamic stimulus, a dynamic visual stimulus, a pre-recorded visual stimulus, a pre-recorded audio stimulus, a pre-recorded audiovisual stimulus, a live visual stimulus, a live audio stimulus, a live audiovisual stimulus, a two-dimensional visual or audiovisual stimulus, or a three-dimensional visual or audiovisual stimulus.

In one aspect, the method includes the pattern of blink inhibition comprising a mean blink rate for the individual during the stimulus. According to one aspect, the method includes the pattern of blink inhibition comprising a moment-by-moment blink rate for the individual. In one aspect, the method includes the pattern of blink inhibition comprising a measure of an instantaneous blink rate for the individual at a certain time point as compared to a mean blink rate for the individual. In another aspect, the present method includes the pattern of blink inhibition comprising a measure of an instantaneous blink rate for the individual at a certain time point as compared to a mean blink rate for a control group. According to one aspect, the method includes the pattern of blink inhibition comprising a measure of the synchronized blink data as compared with predetermined control blink data. In yet another aspect, the present method includes the pattern of blink inhibition comprising a measure of blink inhibition relative to an event in the stimulus.

In one aspect, the method includes the contemporaneous portion of the stimulus comprising the entirety of the stimulus. In another aspect, the method includes the event in the stimulus comprising a physical event or an affective event.

According to one aspect, the method comprises the steps of categorizing the individual into one or more predefined categories based on the marker of engagement and/or synchronizing comprises time-locking or time-correlating the blink data with the stimulus.

In one aspect, the method comprises the marker of engagement relating to a salient portion of the stimulus.

In one aspect, the method further includes the blink data corresponds to a rate of change of the individual's pupil size. According to one aspect, the method comprises the blink data corresponds to eyelid closure of the individual.

In one aspect, the method further comprises the steps of converting the blink data to binary format for comparison purposes and/or categorizing the blink data according to predetermined demographic parameters. In certain embodiments, the above steps can be executed via software on a processor.

In one aspect, the method includes a stimulus comprising an auditory stimulus, dynamic visual stimulus, and/or static stimulus.

In one embodiment, the present disclosure comprises a method for determining perceived stimulus salience by an individual with respect to a stimulus. This embodiment comprises the steps of: receiving blink data indicative of the individual's blink responses to the stimulus; receiving eye-movement data indicative of eye movements for the individual with respect to the stimulus; synchronizing the received blink data and the received eye-movement data with the stimulus; identifying a period of blink inhibition in the synchronized blink data; and determining for the period of blink inhibition identified in the synchronized blink data, at least one spatial fixation location from the synchronized eye-movement data for the individual with respect to the stimulus, whereby the period of blink inhibition and the at least one spatial fixation location indicate markers of perceived temporal and spatial salience with respect to the stimulus. In certain embodiments, the above steps can be executed via software on a processor.

In one aspect, the method includes the step of synchronizing, which comprises time-locking or time-correlating the received blink data and the received eye-movement data with the stimulus.

In one aspect, the method further comprises the steps of converting the blink data to binary format for determination purposes; and/or converting the eye-movement data to coordinate data for determination purposes. In certain embodiments, the above steps can be executed via software on a processor.

According to one aspect, the method further comprises the step of identifying the period of blink inhibition in the synchronized blink data further including the steps of: retrieving control blink data from a database; and comparing the synchronized blink data to the control blink data to identify a difference between the synchronized blink data and the control blink data, whereby the difference corresponds to the period of blink inhibition. In certain embodiments, the above steps can be executed via software on a processor.

In one aspect, the present method includes the control blink data comprising an average blink rate for a plurality of individuals when no stimulus is present. In one aspect, the present method includes the difference between the synchronized blink data and the control blink data comprising one of the following: increased blink rate for the individual as compared to the control blink data, decreased blink rate for the individual as compared to the control blink data, lack of blinks within a predetermined time period, exceeding a predetermined number of blinks within a predetermined time period. According to one aspect, the present method comprises the difference between the synchronized blink data and the control blink data provides a marker of a developmental, cognitive, or mental disorder of the individual. In one embodiment, the present method includes the blink data corresponding to a blink rate for the individual during a defined time period.

According to one aspect, the present method includes the stimulus comprising an auditory stimulus, a dynamic visual stimulus, and/or a static visual stimulus. In one aspect, the present method includes the stimulus comprising one or more of the following: a pre-recorded visual stimulus, a pre-recorded audio stimulus, a pre-recorded audiovisual stimulus, a live visual stimulus, a live audio stimulus, a live audiovisual stimulus, a two-dimensional stimulus, or a three-dimensional stimulus.

In one embodiment, the present disclosure comprises a method for assessing an ability of a stimulus to engage an individual, comprising the steps of: presenting the stimulus to an individual; receiving blink data indicative of the individual's blink responses to the stimulus; identifying a measure of blink inhibition for the individual from the received blink data; and determining, via software executing on the processor, whether the measure of blink inhibition in the received blink data meets a threshold blink inhibition value, whereby the threshold blink inhibition value indicates the ability of the stimulus to engage the individual. In certain embodiments, the above steps can be executed via software on a processor.

In one aspect, the present method includes the step of categorizing, via software executing on the processor, the blink data according to predetermined demographic parameters.

In one aspect, the present method includes the stimulus comprising one or more of the following: a dynamic stimulus, a dynamic visual stimulus, a pre-recorded visual stimulus, a pre-recorded audio stimulus, a pre-recorded audiovisual stimulus, a live visual stimulus, a live audio stimulus, a live audiovisual stimulus, a two-dimensional stimulus, or a three-dimensional stimulus.

According to one aspect, the present method includes the measure of blink inhibition comprising a mean blink rate for the individual during the stimulus. In one aspect, the present method includes the measure of blink inhibition comprising a moment-by-moment blink rate for the individual. In one aspect, the present method includes the measure of blink inhibition comprising a measure of an instantaneous blink rate for the individual at a certain time point as compared to a mean blink rate for the individual, a measure of an instantaneous blink rate for the individual at a certain time point as compared to a mean blink rate for a control group, a measure of the received blink data as compared with predetermined control blink data, and/or a measure of blink inhibition relative to an event in the stimulus.

In one aspect, the present method includes the event in the stimulus comprising a physical event or an affective event.

In one aspect, the present method includes the blink data corresponding to a rate of change of the individual's pupil size and/or eyelid closure of the individual.

According to one aspect of the present method, the method further comprises the steps of, via software executing on the processor, converting the blink data to binary format for determination purposes, categorizing the blink data according to predetermined demographic parameters.

In one aspect, the present method comprises the threshold blink inhibition value indicates a marker for a mental condition. In another aspect, the present method includes the threshold blink inhibition value as selected from a range spanning normality to psychopathology. In one aspect, the present method includes the threshold blink inhibition value corresponding to a diagnostic measure for diagnosing the individual with a mental condition. In one aspect, the present method includes the threshold blink inhibition value corresponding to a predetermined measure of engagement with the stimulus. In another aspect, the present method further includes the threshold blink inhibition value corresponding to a predetermined category for categorizing the individual.

In one aspect, the present method includes the measure of blink inhibition for the individual corresponding to a portion of the stimulus. In another aspect, the present method includes the measure of blink inhibition for the individual corresponding to an entirety of the stimulus.

According to one aspect, the present method includes the stimulus as an auditory stimulus, a dynamic visual stimulus, and/or a static visual stimulus.

In one embodiment, the present disclosure comprises a method for assessing the risk of a mental condition in an individual using an eye monitoring device. This embodiment comprises the steps of: receiving blink data indicative of the individual's blink responses to a dynamic visual stimulus displayed to the individual, wherein the blink data is collected via the eye monitoring device; synchronizing the received blink data with the dynamic visual stimulus; identifying a pattern of blink inhibition in the synchronized blink data; retrieving event data related to the dynamic visual stimulus from a database; and comparing a parameter of the pattern of blink inhibition in the synchronized blink data with a parameter of the event data related to the dynamic visual stimulus to determine at least one delta parameter, wherein the at least one delta parameter indicates a likelihood that the individual has a mental disorder. In certain embodiments, the above steps can be executed via software on a processor.

In one aspect, the present method includes the parameter of the event data comprising a predetermined time-stamped event. In another aspect, the present method includes the event data comprising a time value.

In one aspect, the present method includes the parameter of the pattern of blink inhibition comprising a time value. In one aspect, the present method includes the pattern of blink inhibition comprising a comparison between the individual's blink data and a chance probability of blinking associated with the individual. In another aspect, the present method includes the pattern of blink inhibition comprising a mean blink rate for the individual during the dynamic visual stimulus. Further, in one aspect, the present method includes the pattern of blink inhibition comprising a moment-by-moment blink rate for the individual. In one aspect, the present method includes the pattern of blink inhibition comprising a measure of an instantaneous blink rate for the individual at a certain time point as compared to a mean blink rate for the individual. In yet another aspect, the present method includes the pattern of blink inhibition comprising a measure of an instantaneous blink rate for the individual at a certain time point as compared to a mean blink rate for a control group. In one aspect, the present method includes the pattern of blink inhibition comprising a measure of an instantaneous blink rate for the individual as compared to measure of variance in a mean blink rate for the individual.

In one aspect, the present method includes the at least one delta parameter comprising a time value that exceeds a predetermined threshold value. In one aspect, the present method includes the at least one delta parameter comprising a time value that is less than a predetermined threshold value.

In one aspect, the present method comprises the steps of providing a diagnosis to the individual based on the at least one delta parameter and/or synchronizing, which comprises time-locking or time-correlating the received blink data with the dynamic visual stimulus.

In one aspect, the present method includes the mental condition comprising a developmental or cognitive disorder.

In one aspect, the present method includes the event data corresponding to one or more of the following: physical events within the dynamic visual stimulus, affective events within the dynamic visual stimulus, events presumed to cause or inhibit blinking based on the dynamic visual stimulus.

In one embodiment, the present disclosure comprises A method for evaluating, monitoring, or diagnosing a mental disorder in an individual using an eye monitoring device. This embodiment comprises the steps of: receiving blink data indicative of the individual's blink responses to a stimulus, wherein the blink data is collected via the eye monitoring device; synchronizing the received blink data with the stimulus; identifying, via software executing on the processor, a pattern of blink inhibition in the synchronized blink data; retrieving event data related to the visual stimulus from a database; and comparing a parameter of the pattern of blink inhibition in the synchronized blink data with a parameter of the event data related to the visual stimulus to determine a delta parameter, wherein the delta parameter indicates a likelihood that the individual has a mental disorder. In certain embodiments, the above steps can be executed via software on a processor.

In one aspect, the present method further comprises the steps of: receiving eye-movement data indicative of the individual's eye movements with respect to the stimulus; receiving eye-movement data indicative of each member of a control group's eye movements with respect to the stimulus; generating a three-dimensional scanpath based on the data for each of the members of the control group and for the individual, wherein two of the dimensions of the scanpath correspond to a position of a point of regard for each of the members and the individual and one of the dimensions corresponds to time; identifying a convergence of the scanpaths of the members of the control group; and comparing via software executing on the processor, the scanpath of the individual to the scanpaths of the members of the control group in the region of the convergence. In certain embodiments, the above steps can be executed via software on a processor.

In one aspect, the present method includes wherein the parameter of the event data comprising a predetermined time-stamped event. In one aspect, the present method includes the parameter of the event data comprising a time value. In another aspect, the present method includes the parameter of the pattern of blink inhibition comprising a time value.

In one aspect, the present method includes the delta parameter comprising a time value that exceeds a predetermined threshold value. In one aspect, the present method includes the delta parameter comprising a time value that is less than a predetermined threshold value.

In one aspect, the present method includes the stimulus as an auditory stimulus, a dynamic visual stimulus, and/or a static visual stimulus.

In one aspect, the present method includes the event data corresponding to one or more of the following: physical events within the dynamic visual stimulus, affective events within the dynamic visual stimulus, events presumed to cause or inhibit blinking based on the dynamic visual stimulus.

In one aspect, the present method includes the step of synchronizing which comprises time-locking or time-correlating the received blink data with the stimulus.

In one aspect, the present method includes the pattern of blink inhibition comprising a comparison between the individual's blink data and a chance probability of blinking associated with the individual. In one aspect, the present method includes the pattern of blink inhibition comprising a mean blink rate for the individual during the stimulus. In another aspect, the present method includes the pattern of blink inhibition comprising a moment-by-moment blink rate for the individual. In one aspect, the present method includes the pattern of blink inhibition comprising a measure of an instantaneous blink rate for the individual at a certain time point as compared to a mean blink rate for the individual. In yet another aspect, the present method includes the pattern of blink inhibition comprising a measure of an instantaneous blink rate for the individual at a certain time point as compared to a mean blink rate for a control group. Further, in another aspect, the present method includes the pattern of blink inhibition comprising a measure of an instantaneous blink rate for the individual as compared to measure of variance in a mean blink rate for the individual.

In one embodiment, the present disclosure comprises a method for evaluating, monitoring, or diagnosing a mental condition in an individual using an eye monitoring device. This embodiment comprises the steps of: receiving blink data indicative of the individual's blink responses to a dynamic visual stimulus displayed to the individual, wherein the blink data is collected using the eye monitoring device; synchronizing the received blink data with the dynamic visual stimulus; identifying a pattern of blink inhibition in the synchronized blink data; retrieving a control pattern of blink inhibition for the dynamic visual stimulus displayed to the individual from a database; and comparing the pattern of blink inhibition in the synchronized blink data with the control pattern of blink inhibition to determine whether the pattern of blink inhibition falls outside a range of the control pattern of blink inhibition and thereby indicates a likelihood that the individual has a mental condition. In certain embodiments, the above steps can be executed via software on a processor.

In one aspect, the present method includes the mental condition comprising a developmental or cognitive disorder.

In one aspect, the present method further includes the steps of synchronizing comprises time-locking or time-correlating the received blink data with the dynamic visual stimulus and/or converting, via software executing on the processor, the blink data to binary format for identification purposes.

In one aspect, the present method includes the blink data for the individual corresponding to a rate of change of pupil size for the individual. In one aspect, the present method includes the blink data corresponding to eyelid closure for the individual.

In one aspect, the present method includes the control pattern of blink inhibition comprising an average blink rate for a plurality of individuals in response to the dynamic visual stimulus. According to one aspect, the present method includes the control pattern of blink inhibition comprising a probability distribution of average blink rates for a plurality of individuals as obtained by permuting the blink data of the plurality of individuals. According to one aspect, the present method includes the control pattern of blink inhibition indicating a severity of the mental condition.

In one aspect, the present method includes the steps of permuting the data of the plurality of individuals comprising circular shifting with respect to an original timing of blink data collection and/or the step of permuting the data of the plurality of individuals comprising randomizing an order of blinks and inter-blink intervals for each individual.

In one aspect, the present method includes the pattern of blink inhibition comprising a mean blink rate for the individual during the dynamic visual stimulus. In another aspect, the present method includes the pattern of blink inhibition comprising a moment-by-moment blink rate for the individual. In one aspect, the present method includes the pattern of blink inhibition comprising a measure of an instantaneous blink rate for the individual at a certain time point and the control pattern of blink inhibition comprises an instantaneous blink rate for a control group. In one aspect, the present method includes the control pattern of blink inhibition comprising an average blink rate for the individual when no dynamic visual stimulus is present. In yet another aspect, the present method includes the pattern of blink inhibition comprising a measure of blink inhibition relative to an event in the dynamic visual stimulus.

In one aspect, the present method includes the event in the dynamic visual stimulus comprising a physical event or an affective event.

In one embodiment, the present disclosure comprises a method for assessing user responses to a stimulus based on blink inhibition. This embodiment comprises the steps of: receiving blink data indicative of a user's blink responses to a stimulus; identifying a pattern of blink inhibition in the blink data; retrieving a control pattern of blink inhibition for the stimulus from a database, wherein the control pattern corresponds to a predefined user category; and comparing the pattern of blink inhibition in the blink data with the control pattern of blink inhibition to determine whether the user within the predefined user category. In certain embodiments, the above steps can be executed via software on a processor.

In one aspect, the present method includes the blink data is received via the use of an eye monitoring device.

In one aspect, the present method includes the stimulus comprising an auditory stimulus, a dynamic visual stimulus, and/or a static visual stimulus. In one aspect, the present method includes the stimulus comprising one or more of the following: a dynamic stimulus, a dynamic visual stimulus, a pre-recorded visual stimulus, a pre-recorded audio stimulus, a pre-recorded audiovisual stimulus, a live visual stimulus, a live audio stimulus, a live audiovisual stimulus, a two-dimensional stimulus, or a three-dimensional stimulus.

In one aspect, the present method includes the blink data for the user corresponding to a rate of change of pupil size for the user. In another aspect, the present method comprises the blink data corresponds to eyelid closure for the user.

In one aspect, the present method includes the control pattern of blink inhibition comprising an average blink rate for a plurality of users in response to the stimulus. In one aspect, the present method includes the control pattern of blink inhibition comprising a probability distribution of average blink rates for a plurality of users as obtained by permuting the blink data of the plurality of users.

In one aspect, the present method includes the steps of converting, via software executing on the processor, the blink data to binary format for comparison purposes, permuting the data of the plurality of users comprising circular shifting with respect to an original timing of blink data collection, and/or permuting the data of the plurality of users comprises randomizing an order of blinks and inter-blink intervals for each user.

In one aspect, the present method includes the pattern of blink inhibition comprising a mean blink rate for the user during the stimulus. In another aspect, the present method includes the pattern of blink inhibition comprising a moment-by-moment blink rate for the user. In one aspect, the present method includes the pattern of blink inhibition comprising a measure of an instantaneous blink rate for the user at a certain time point and the control pattern of blink inhibition comprising an instantaneous blink rate for a control group. In another aspect, the present method includes the pattern of blink inhibition comprising a measure of blink inhibition relative to an event in the stimulus.

In one aspect, the present method includes the control pattern of blink inhibition comprising an average blink rate for the user when no stimulus is present.

In one aspect, the present method includes wherein the event in the dynamic stimulus comprising a physical event or an affective event.

In one aspect, the present method includes the steps of receiving additional blink data for the user over time; identifying an additional pattern of blink inhibition in the additional blink data; comparing the additional pattern of blink inhibition to the pattern of blink inhibition to determine whether the user remains within the predetermined user category. In certain embodiments, the above steps can be executed via software on a processor.

These and other aspects, features, and benefits of the claimed invention(s) will become apparent from the following detailed written description of the preferred embodiments and aspects taken in conjunction with the following drawings, although variations and modifications thereto may be effected without departing from the spirit and scope of the novel concepts of the disclosure.

BRIEF DESCRIPTION OF THE DRAWINGS

The accompanying drawings illustrate one or more embodiments and/or aspects of the disclosure and, together with the written description, serve to explain the principles of the disclosure. Wherever possible, the same reference numbers are used throughout the drawings to refer to the same or like elements of an embodiment, and wherein:

FIG. 2 is a flowchart showing an overview of the data collection and assessment process of an eye monitoring system, according to one embodiment of the present disclosure.

FIG. 3 illustrates blinking and statistically significant blink inhibition while viewing a visual stimulus, according to one embodiment of the present disclosure.

FIG. 4 is a graph illustrating an exemplary blink rate comparison between typical toddlers and toddlers with autism spectrum disorder, according to one embodiment of the present disclosure.

FIG. 5A is a graph illustrating an exemplary correlation of blink rates and age in typical toddlers, according to one aspect of the present disclosure.

FIG. 5B is a graph illustrating an exemplary correlation of blink rates and age in toddlers diagnosed with autism spectrum disorder, according to one aspect of the present disclosure.

FIG. 7A is a graph illustrating participant blink data versus time, according to one embodiment of the present disclosure.

FIG. 7B is a graph illustrating instantaneous blink rate versus time, according to one embodiment of the present disclosure.

FIG. 7C is a graph illustrating the $95^{th}$ and $5^{th}$ percentile of permuted blink data versus time, according to one embodiment of the present disclosure.

FIG. 7D is a graph illustrating periods of blink inhibition plotted with respect to time, according to one embodiment of the present disclosure.

FIG. 8G is a graph illustrating blink inhibition relative to affective events for toddlers diagnosed with autism spectrum disorder, according to one embodiment of the present disclosure.

FIG. 8H is a graph illustrating blink inhibition relative to physical events for toddlers diagnosed with autism spectrum disorder, according to one embodiment of the present disclosure.

FIG. 8I is a graph illustrating blink response relative to non-affective and nonphysical events for toddlers diagnosed with autism spectrum disorder, according to one embodiment of the present disclosure.

FIG. 8J illustrates exemplary visual fixation relating to affective events for toddlers with autism spectrum disorder, according to one embodiment of the present disclosure.

FIG. 8K illustrates exemplary visual fixation relating to physical events for toddlers with autism spectrum disorder, according to one embodiment of the present disclosure.

FIG. 8L illustrates exemplary visual fixation relating to nonaffective and nonphysical events for toddlers with autism spectrum disorder, according to one embodiment of the present disclosure.

FIG. 8M is a graph illustrating timing of blink inhibition relative to affective and physical events for toddlers diagnosed with autism spectrum disorder and typical toddlers, according to one embodiment of the present disclosure.

FIG. 8N is a graph illustrating percent change in blinks per minute relative to affective physical and events for toddlers diagnosed with autism spectrum disorder and typical toddlers, according to one embodiment of the present disclosure.

FIG. 8O is a graph illustrating percent fixation on objects relative to affective and physical events for toddlers diagnosed with autism spectrum disorder and typical toddlers, according to one embodiment of the present disclosure.

FIG. 9A is a graph illustrating an empirical cumulative distribution function comparing actual typical toddler data with permuted typical toddler data, according to one embodiment of the present disclosure.

FIG. 9B is a graph illustrating an empirical cumulative distribution function comparing actual toddlers diagnosed with ASD data with permuted toddlers diagnosed with ASD data, according to one aspect of the present disclosure.

FIG. 10 is a flowchart illustrating an exemplary process for determining engagement activity, according to one embodiment of the present disclosure.

FIG. 11 is a flowchart illustrating an exemplary process for assessing disease/disorder state, according to one embodiment of the present disclosure.

FIG. 12 is a flowchart illustrating an exemplary process for assessing perceived stimulus salience, according to one embodiment of the present disclosure.

FIG. 13 is a flowchart illustrating an exemplary process for identifying most engaging spatial and temporal features of a visual stimulus, according to one embodiment of the present disclosure.

FIG. 14 is a flowchart illustrating an exemplary patient/condition assessment process, according to one embodiment of the present disclosure.

DETAILED DESCRIPTION

Figure 1A:
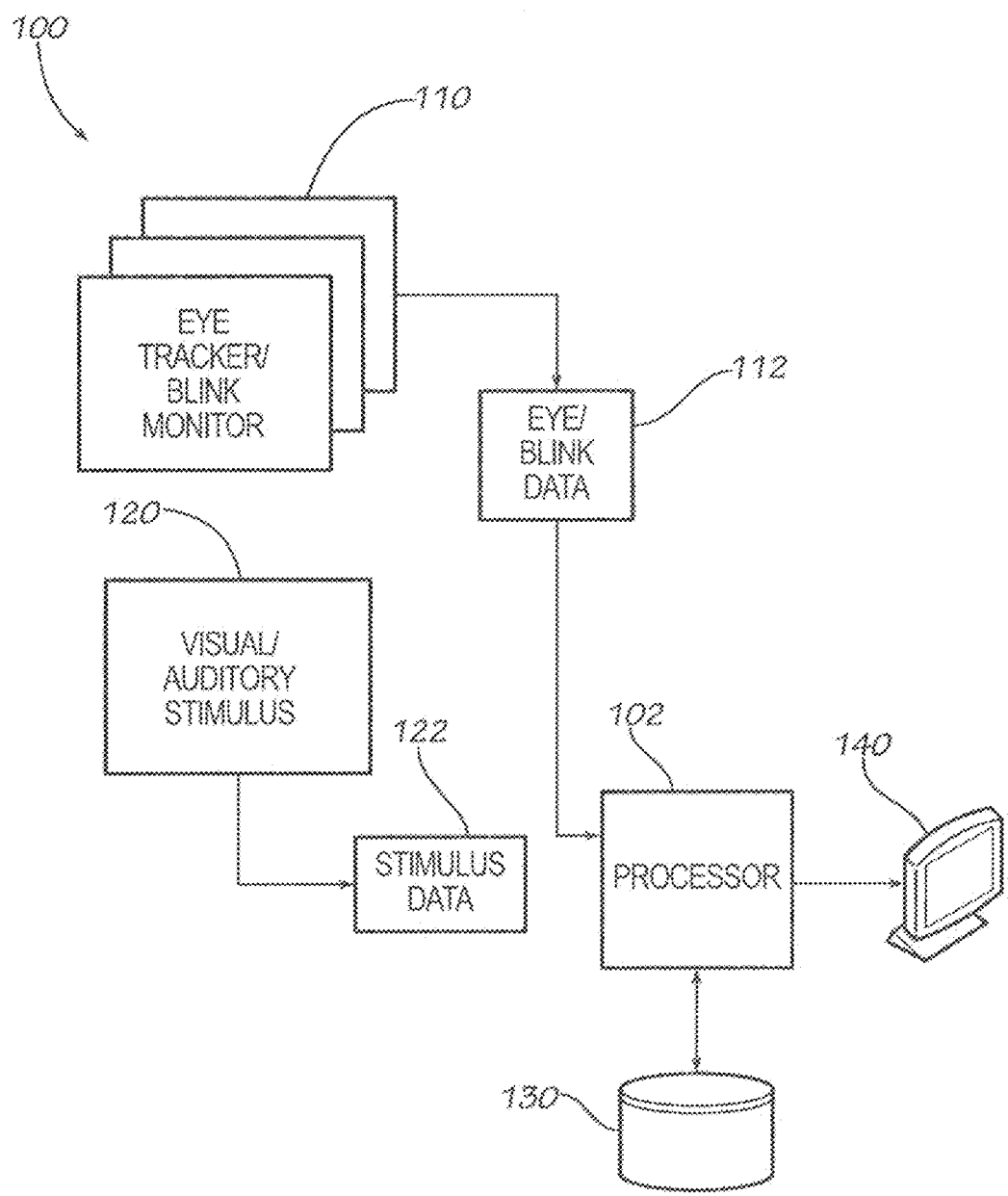
FIG. 1A illustrates an exemplary block diagram of an eye monitoring system, according to one embodiment of the present disclosure.

Prior to a detailed description of the disclosure, the following definitions are provided as an aid to understanding the subject matter and terminology of aspects of the present systems and methods, are exemplary, and not necessarily limiting of the aspects of the systems and methods, which are expressed in the claims. Whether or not a term is capitalized is not considered definitive or limiting of the meaning of a term. As used in this document, a capitalized term shall have the same meaning as an uncapitalized term, unless the context of the usage specifically indicates that a more restrictive meaning for the capitalized term is intended. However, the capitalization or lack thereof within the remainder of this document is not intended to be necessarily limiting unless the context clearly indicates that such limitation is intended.

All publications, patents, and published patent applications referred to in this application are specifically incorporated by reference herein. In case of conflict, the present specification, including its specific definitions, will control.

Throughout this specification, the term "comprise" or variations such as "comprising" or "comprises" will be understood to imply the inclusion of a stated integer (or component) or group of integers (or components), but not the exclusion of any integer (or component) or group of integers (or components).

The singular forms "a", "an", and "the" include the plurals unless the context clearly dictates otherwise.

Definitions/Glossary

M: mean or average of a set of numerical values within a data set.

SD: standard deviation, which indicates the variation from an average or mean value of a relevant data set.

r: Pearson's product-moment correlation coefficient, which is a measure of the strength and direction of the linear relationship between two variables, normally within a related data set.

t: test statistic value from 1 or 2 sample t test.

P: is a symbol for percentage/percentile of some set of data points.

ANOVA: analysis of variance, which is a collection of statistical models used to analyze the differences between group means (averages) and associated variations of data among and between groups.

SE: Standard error, which is the standard deviation of the sampling distribution of a statistic.

F: f-test, which is a statistical test where the test statistic has an F-distribution under the null hypothesis, mostly used when comparing statistical model that fit into a data set.

z: the result of a z-test that is a statistical test for which the distribution of the test statistic under the null hypothesis can be approximated by a normal distribution within a given data set.

Overview

For the purpose of promoting an understanding of the principles of the present disclosure, reference will now be made to the embodiments illustrated in the drawings and specific language will be used to describe the same. It will, nevertheless, be understood that no limitation of the scope of the disclosure is thereby intended; any alterations and further modifications of the described or illustrated embodiments, and any further applications of the principles of the disclosure as illustrated therein are contemplated as would normally occur to one skilled in the art to which the disclosure relates. All limitations of scope should be determined in accordance with and as expressed in the claims.

Aspects of the present disclosure generally relate to systems and methods for assessing blink inhibition and blink response as indicators of engagement with visual stimuli. In particular, aspects of the present disclosure relate to utilizing the timing of blink inhibition during natural viewing and in response to visual stimuli to: to assess viewer engagement with stimuli, to assess viewer perception of the relative salience of stimuli, to assess a stimulus's power to engage specific viewers or groups of viewers, to identify the most engaging spatial and temporal features of a stimulus, and to categorize or rate viewers as a function of their engagement with a given stimulus for demographic or diagnostic purposes. According to one embodiment, the present systems and methods provide a tool for assessing viewer engagement on the basis of blink rate and the timing of blinking and blink inhibition, during natural viewing. In one embodiment, the present systems and methods provide a tool for quantifying viewers' moment-by-moment engagement with visual content and the degree to which viewer engagement varies dynamically.

Further, and according to one embodiment, the present systems and methods provide a mechanism for determining, by a "data mining" approach, the most engaging spatial and temporal features of a stimulus on the basis of time-varying viewer engagement. Further aspects of the present disclosure relate to the way in which these measures of engagement can be combined with eye-tracking point-of-gaze data to measure the specific parts of a stimulus that a viewer is fixating upon at moments of greater or lesser engagement (e.g., fixation locations).

Further aspects of the present disclosure relate to systems and methods for assessing disease/disorder state (e.g., presence/absence of a condition), disease/disorder state progression, and/or treatment response in conditions for example but not limited to autism spectrum disorders (ASD), ADHD, schizophrenia, bipolar disorder, depression, post-traumatic stress disorder (PTSD), and others that effect engagement with circumscribed content or engagement. In one embodiment, in research leading to the present disclosure, toddlers with ASD, unlike typically developing comparison children, demonstrate markedly delayed blink inhibition in relation to specific visual events. The present systems and methods indicate that typical toddlers, relative to the same visual events, inhibit their blinking earlier than toddlers with ASD. This difference provides evidence of intact cognitive processes in typical toddlers and evidence that those processes are disrupted in toddlers with ASD: typical toddlers inhibited their blinking in active anticipation of the unfolding of salient social events, while toddlers with ASD did not. These measurements provide information that can be used for assessing diagnostic status as well as for measuring severity of symptomatology. Related embodiments can be deployed to measure the level of engagement of, for example, recovering drug addicts with environmental triggers (for example, images of alcohol, drugs, or locations in which such substances are typically procured or consumed) in order to assess risk for relapse.

Experimental Data and Analysis

The following exemplary discussion relates to a conducted experiment(s) to measure blink inhibition as an indicator of viewer engagement with visual stimuli. The experiment(s) utilize the timing of blink inhibition of toddlers during natural viewing of a stimulus to assess various aspects in connection with levels of engagement. Details of the experiment(s) conducted along with associated data/parameters, exemplary settings, the associated results from the experiment(s), general implications, and alternate embodiments will be better understood in the description and accompanying figures provided in greater detail below.

In the descriptions that follow, the term "blink data" generally relates to a measurement of the timing and/or presence/number of eye-blinks during natural viewing of a visual stimulus, how blinks are modulated between as well as within tasks, and how the timing of blinks varies as a function of viewer engagement and various stimulus events. Additional examples of blink data may comprise blink rate before, during, and after a task, wherein the blink rate is measured and analyzed for variations at a plurality of intervals throughout the viewing of a visual stimulus; in particular, before, during, and after viewing the visual stimulus. Blink data may also comprise measurements of instantaneous blink rate as it relates to intratask blink inhibition. Further, it will be understood that blink data are generally used to assess various levels of blink inhibition, timing of blink inhibition, viewer engagement with stimuli, viewer perception of relative salience of stimuli, a stimuli's capability to engage a viewer, etc. In another aspect, blink data may relate to the measurement of the timing and/or presence/number of eye-blinks during the listening of an auditory stimulus. Similar to the various mechanisms relating to a visual stimulus, the same measures may apply while listening to an auditory stimulus.

Also referred to herein, stimulus events in this example, without limitation to other possible embodiments thereof, generally comprise three groups: nonaffective/nonphysical events, physical events, and affective events. Affective events generally comprise events within the visual stimulus having an effect on emotional behavior, such as facial expressions and/or vocalizations eliciting heightened emotional affect. Physical events typically relate to events wherein a discrete object within the visual stimulus is moving, shifting locations, changing states, etc. Any other portion of the visual stimulus that is not categorized as an affective or physical event is categorized as nonaffective/nonphysical events. As will be understood by one of ordinary skill in the art, the use of the terms affective, physical, nonaffective and nonphysical events are merely used in the exemplary discussion below and are not intended to limit the spirit or scope of the present disclosure.

For the experiment(s) described herein, the following methodologies, testing equipment, parameters, and standards were followed: (1) determination of ratings of affective and physical events, (2) determination of instantaneous blink rate, (3) various permutation testing in connection with assessing instantaneous blink rate, and (4) determination of control blink inhibition data. Further, various other experimental methodologies utilized in the present disclosure are similar to those used in prior patents and published papers by some of the same inventors of the present application, and are described in at least the following patents that are hereby incorporated by reference; in particular: U.S. Pat. No. 7,922,670, titled System and Method for Quantifying and Mapping Visual Salience, issued Apr. 12, 2011, U.S. Pat. No. 8,343,067, titled System and Method for Quantifying and Mapping Visual Salience, issued Jan. 1, 2013, and U.S. Pat. No. 8,551,015, titled System and Method for Evaluating and Diagnosing Patients Based on Ocular Response, issued Oct. 8, 2013.

The aforementioned references generally relate to systems and methods for mapping and analyzing visual salience (the measure of a given viewer's visual attention as it relates to or stands out against another's visual attention) as a viewer or group of viewers visually engage with a visual stimulus. In particular, the references generally describe various methods for recording, analyzing, and displaying visual salience for an individual or a distributed group of individuals or providing a mechanism to compare an individual's or selected group of individual visual responses to a known set of visual responses. In certain embodiments, a monitoring device (or eye tracker) is generally used in conjunction with the visual stimulus to measure the physical location at which a person is looking. Further, the earlier disclosures describe methods for coordinating visual salience data to a specific instance in time of the visual stimulus. This provides diagnostic information according to what a control or typical individual's data suggest in comparison with a test individual, group of test individuals, or known data.

Still referring to the earlier patents incorporated herein by reference, in one embodiment, each viewer's set of data may be graphed on an x, y, and z-axis coordinate system, wherein the x and y dimensions generally represent an area on the visual stimulus or point of regard with which a viewer engages (e.g., spatial fixation locations towards which a viewer's gaze is directed). Further, the z-axis generally corresponds to time and may be time-locked (or time-correlated or synchronized) with the visual stimulus. Accordingly, multiple sets of data or lines can be mapped onto the same plot to generate a set of data or scan path, whether it is a control group (the group whose data is known and used as the standard) or the group/individual being tested. Generally, at least two trends emerge when analyzing the visual salience data: (1) the test data (points) are loosely distributed and form a large radius (circle) if the points were connected in a circular manner, and (2) the test data or points are closely clustered together forming a tight grouping and a small radius (circle) if the points are connected in a circular manner. In the first instance, wherein the large circle is formed, this is generally called a divergent set meaning the data points are random and tend to spread away from each other. The second instance, wherein the small circle is formed, is typically called a convergent set meaning the data points have a tendency to plot closely and gravitate towards each other.

Further, the earlier patents referenced above further describe divergent data sets as a particular instance in time or a particular frame where the majority of individuals engage different areas on the screen. Conversely and according to another embodiment, a convergent set describes a scenario where most individuals engage the visual stimulus in one area (x, y-axis) on the screen during a particular frame or instance in time. Further, the individual data sets or lines are connected radially and linearly to form a varying three-dimensional shape that resembles a collection of cones or beehives horizontally connected together (also referred to herein as an attentional funnel). The wider parts of the cone represent divergent data sets and the closer segments of the cone represent convergent data sets. These three-dimensional collections of data points are used to analyze and compare various test individuals or test groups. In the scenario in which a test individual does not have visual salience data points in convergent sets, the data point is flagged and noted. If there is a pattern of data points existing outside of the convergent sets, there is an increased probability the testing individual is not engaging with the stimulus according to the control data. Further details of the aforementioned references will be described in greater detail in connection with FIGS. 1B-1D.

Now referring to the specific experiment(s) and test data described herein, test methodologies comprised the utilization of ninety-three children with a mean (M) chronological age of 2.3 years (SD=0.55) participating in the experiment(s) disclosed herein. The visual stimulus comprised a video the children watched that included an unscripted interaction between a boy and a girl playing together in a toy wagon (as representatively shown in FIG. 3). None of the participants had previously viewed the video. Further, in unscripted scenes of natural interaction, the video included various physical and affective events. For example, a physical event shown in the video comprised a door of the wagon opening and closing. Similarly, an affective event shown in the video comprised an argument between the boy and the girl. Although, the physical and affective events were not mutually exclusive, the locations of the greatest affect were spatially discrete from those of most movement, with affectively charged facial expressions separated from the physical location of the door.

The distinction between affective and physical events was relevant to the experimental design because the children who watched the video were divided into two groups that were expected to vary in their response to affective and physical cues. The video was shown to 41 two-year-olds with autism spectrum disorders (ASD) as well as 52 typical two-year-olds. Here, the children with ASD provide a preferred comparison group because the children have been shown previously to display atypical patterns of visual attention to social interaction, attenuated reactivity to varying social affect, and lack of differential response to social attentional cues, but also intact response to physical attentional cues and intact ability to predict and attend to physical events. In the present experimental paradigm, blink inhibition was tested as a marker of perceived stimulus salience, varying by group membership.

FIG. 1A illustrates an exemplary blink and/or eye monitoring system 100 for quantifying and mapping visual salience and for quantifying visual engagement over time as utilized in one test methodology. The system 100 shown in FIG. 1 is a representation of the system used to test the individuals in the experiment(s) described herein. The system includes at least one processor 102. Processor 102 may be any type of device designed to receive and execute software programs, or that which is designed to be modified in functionality by software programs. For example, the processor 102 may be selected from a group comprising digital signal processors, microcontrollers, and microprocessors, or a group consisting of field programmable gate arrays, and computer programmable logic devices. The functionality associated with the processor 102 may be centralized or distributed, whether locally or remotely.

In one embodiment, the processor 102 includes software executing thereon for receiving data indicative of a group of individual's blink responses to a visual stimulus 120. For example, the processor 102 may receive eye data 112 from any number of eye trackers 110 or eye tracking devices. Each eye tracker 110 may be any device for tracking the blink response of at least one eye of an individual (e.g., individual human or any other species/animal). In one embodiment, the eye tracker 110 may be an infrared videooculography eye-tracking device. In another embodiment, the eye tracker 110 is a binocular eye tracker. In another embodiment, the eye tracker may comprise a blink monitoring system for identifying blinks performed by a subject. In such an embodiment, the processor will receive blink data 112 indicative of the subject's blink responses to a visual stimulus 120. In yet another embodiment, the eye tracker 110 may comprise a combination of an eye-tracking device and a blink monitoring device, wherein the eye tracker 110 is capable of detecting eye data and blink data. According to another aspect, each eye tracker 110 may generate eye data 112 indicative of eye movement responses such as eye movements, direction, dilation, rotation, gaze, blinking, etc. As will be understood by one of ordinary skill in the art, eye data may include blink data for exemplary purposes and is not intended to limit the spirit or scope of the present disclosure.

In one aspect based on the eye blink data 112, the processor may determine and/or identify a measurement of the timing and/or presence/number of eye-blinks, how blinks are modulated between as well as within tasks, and how the timing of blinks varies as a function of viewer engagement and various stimulus events. Additionally the processor may determine blink rate before, during, and after a task, wherein the blink rate is measured and analyzed for variations at a plurality of intervals throughout the viewing of a visual stimulus; in particular, before, during, and after viewing the visual stimulus. Blink data may also comprise measurements of instantaneous blink rate as it relates to intratask blink inhibition.

In another aspect, based on the eye/blink data 112, the processor 102 may determine and/or identify points of regard or fixation points. A point of regard (or point-of-gaze or fixation location) is a point at which an eye and/or both eyes of an individual are focusing. A point of regard may be indicated as a coordinate in space (e.g., x, y, z) or a two-dimensional coordinate data (e.g., x, y) on a surface or visual stimulus portrayed on a surface. A point of regard may additionally be referenced with a time (t). Each point of regard may indicate a point of fixation or any point of at which an eye is focusing regardless of the length of time or fixation on the point.

In some embodiments, the system includes a visual stimulus 120. The visual stimulus 120 may be any visual stimulus such as a still image (e.g., print ad, webpage, painting, etc.), video imagery, a 2-D image or video, a 3-D image or video, a live video, a pre-recorded video, interactive media, etc. In an exemplary embodiment, the visual stimulus 120 is a dynamic visual stimulus such as a video. The video may include any imagery, broadcast, recording and/or representation of visual images of stationary or moving objects including, but not limited to, a motion picture, a video game, and/or a recording of a live event. The video may be embodied in any form of media such as film, video tape, DVD, CD-ROM and/or digital storage (e.g., storage 130). The visual stimulus 120 may also be a live event (e.g., theatrical performance, social interaction, training exercise, etc.) or any representation thereof (either two- or three-dimensional).

Further, in other embodiments, the stimulus may comprise an audio stimulus (not shown), wherein an audio stimulus may comprise a live recording, mp3, a compact disc, a DVD soundtrack, DVD audio without the picture, or any other mechanism of the like. Accordingly, the eye trackers 110 will monitor and record eye data 112 as a tester engages with the auditory stimulus. In one aspect, the eye data 112 comprises various eye movement responses for determining various areas of fixation, the level of tester engagement with the stimulus, and various data in connection to blinking and blink inhibition. In other aspects, the eye data 112 indicative of various eye movement responses for assessing a stimulus's ability to engage specific viewers or groups of viewers, to identify the most engaging special and temporal features of a stimulus, and to categorize or index viewers as a function of their engagement with a given stimulus, for either demographic or diagnostic purposes.

Some embodiments of the system further include software utilized by the processor 102 for receiving stimulus data 122 from the visual stimulus 120 or auditory stimulus (not shown). The stimulus data 122 may be, for example, data representing the visual stimulus 120 (e.g., representation or video recording of a live event), a complete video visual stimulus 120, or any portion of a visual stimulus 120 (e.g., frames and/or screenshots). Similarly, the stimulus data 122 may comprise data representing an audio stimulus (e.g., recording of audio, digital recording), a portion of an audio stimulus, etc. In some aspects, data may also include time related info to enable mapping or time-lock of the stimulus to a plurality of eye and/or blink data.

The system may also include a database 130. The database 130 may be collocated with the processor 102 or may be remotely located and accessible via a communications network. The database 130 may provide temporary storage for the processor 102 (e.g., random access memory) and/or permanent or semi-permanent data storage, e.g., for eye data 112 or stimulus data 122. The system may further include any number of displays 140. The display 140 may also be located either local or remote to the processor 102. For example, the display 140 may be remotely located and receive data or information from the processor 102 via the Internet. As will be described below, data representing blink responses, blink assessments, points of regard, distributions of visual resources, and/or a group's distribution of visual resources and/or engagement to the visual stimulus 120 may be presented on the display 140.

Figure 1B:
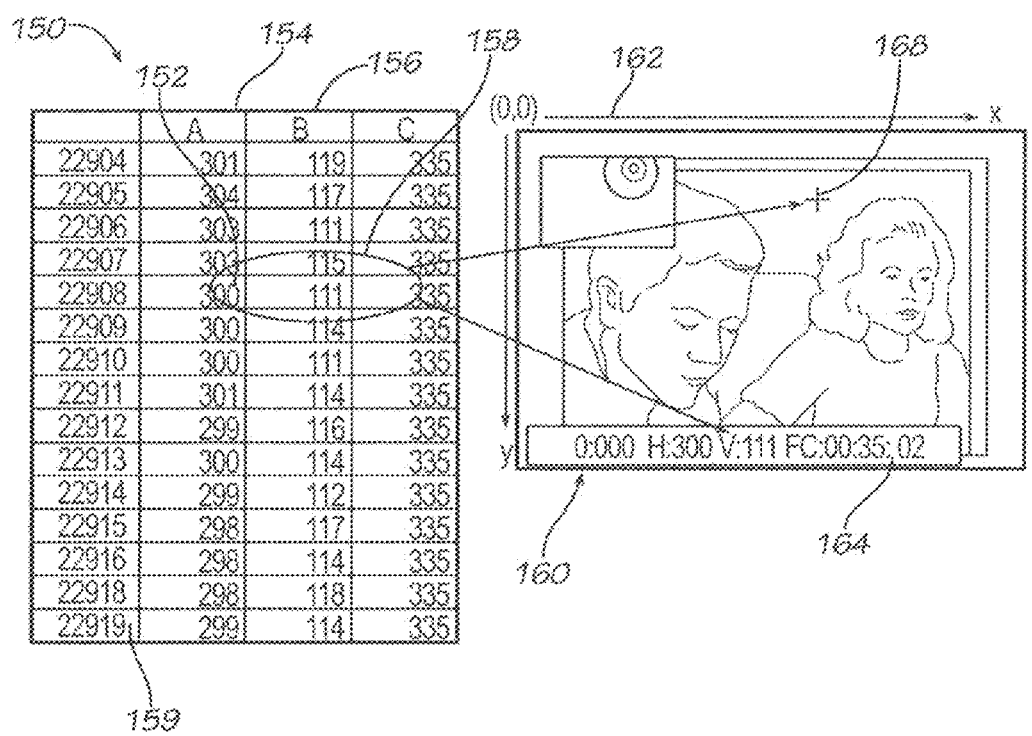
FIG. 1B illustrates data eye movement responses to a visual stimulus, according to one aspect of the present disclosure.

FIG. 1B shows an exemplary table 150 of data indicative of ocular responses to a visual stimulus, or eye data 112. It should be understood that the eye data 112 may be organized and/or maintained in any manner or format and that the table is only exemplary. As such, the table 150 may be organized in any manner such as in columns 154, 156, 159 as shown. In the present illustration, the data is referenced as coordinates describing points of regard (or fixation locations). For example, an x-value of 300 is shown at 152 with a corresponding y-value of 111 at 158. The coordinate in the present example further includes a time value in column 159, e.g., referring to a time that the particular coordinate of eye data 112 was sampled. The time value may further correspond to a time 164 of a visual stimulus 160. Any number of additional categories (e.g., columns) of eye data 112 may be represented such as a z-value referring to a distance for the point of regard.

As shown in FIG. 1B, a point of regard in the table 150 may be mapped to the visual stimulus 160. For example, the point of regard referenced at 152 and 158 may be mapped to a point 168 on a portion of the visual stimulus, e.g., using a coordinate system 162. In some embodiments, the coordinate system 162 may relate to any video pixel coordinate system (e.g., 640×480 or 720×480). The portion of the visual stimulus 160 may be a portion (e.g., frame or panel) corresponding to the time at which the point of regard was sampled.

The eye data 112 may include data sampled at any rate or frequency. For example, eye data 112 may be sampled from an individual at a sampling frequency of 60 Hz, 512 Hz, 1000 Hz, or any other sampling frequency. The rate of visualization or presentation of eye data may be increased or decreased as desired and/or adjusted based on a rate of change of the dynamic visual stimulus, e.g., 160. Both rates of analysis and rates of presentation of eye data may also be based on analysis of meaningful segments of video isolated for scrutiny. For example, if meaningful events in the stimuli occur at a rate of 30 times per second, rates of sampling, analysis, and presentation could equal or exceed 30 Hz.

Figure 1C:
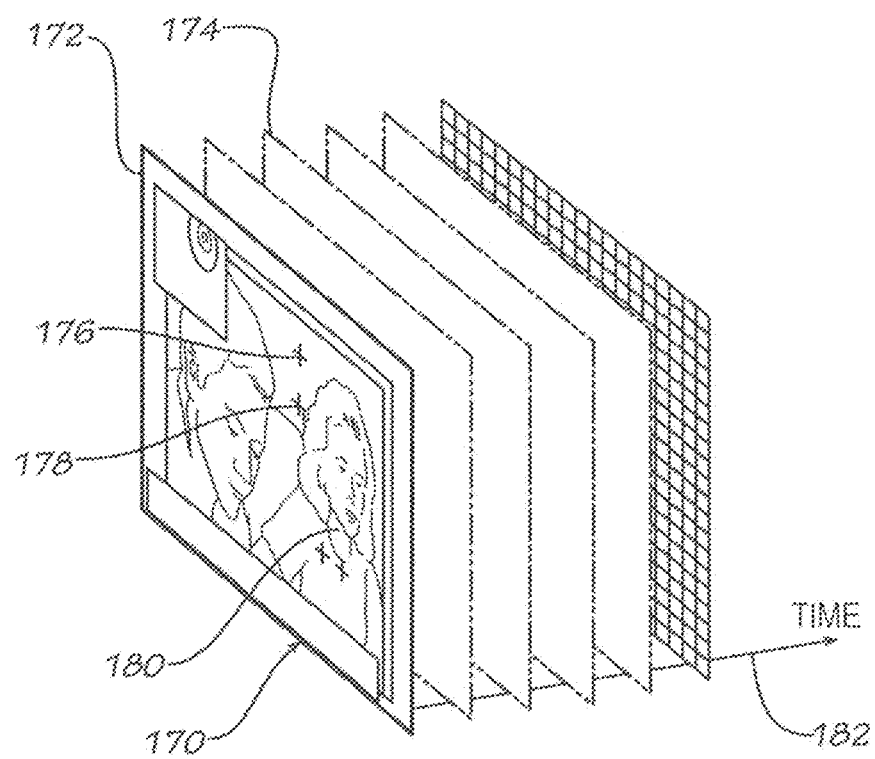
FIG. 1C illustrates a display of portions of a dynamic visual stimulus over time and data indicative of eye movement responses to the dynamic visual stimulus, according to one embodiment of the present disclosure.

FIG. 1C shows a display 170 of several portions and/or frames of a dynamic visual stimulus. As shown, the display 170 includes a time axis 182 and any number of frames, e.g., 172, 174, corresponding to different times of the dynamic visual stimulus. Further represented in the display 170 are points of regard, e.g., 176, 178, 180, on the frame 172. Each of the points of regard may be determined from eye data 112 sampled from different individuals. Alternatively, each point of regard may be determined from different viewings of the same dynamic visual stimulus by one individual.

Figure 1D:
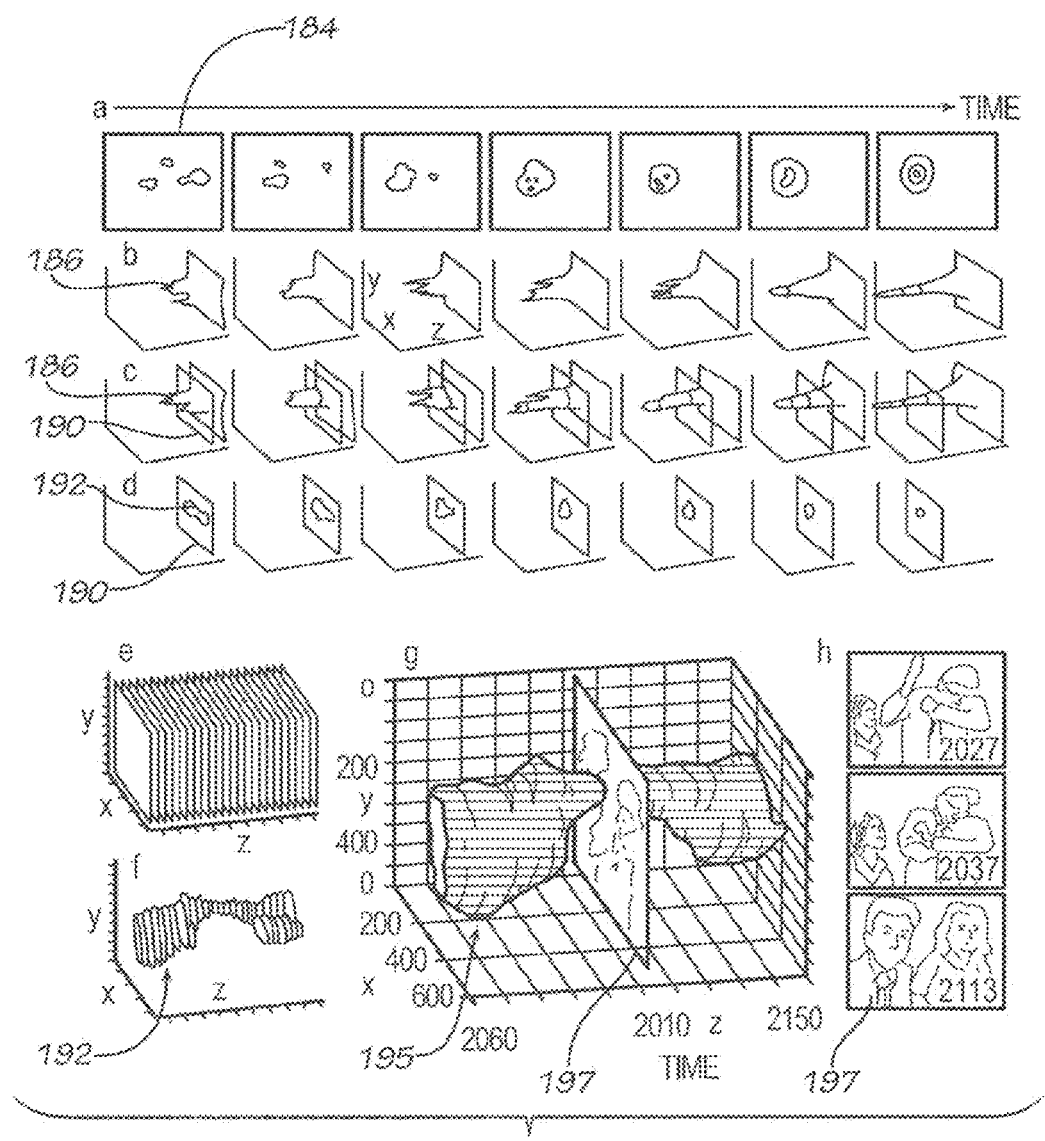
FIG. 1D shows an exemplary generation of display of a group's distribution of visual resources, according to one embodiment of the present disclosure.

Referring to FIG. 1D, the system 100 according to the present disclosure further includes software for generating a display of the test group's distribution of visual resources to the visual stimulus. FIGS. 1Da-1Dh show an example of a mechanisms by which to generate a display of the group's distribution of visual resources according to the present disclosure. FIG. 1Da shows two-dimensional representations of a group of individuals' distribution of visual resources (e.g., 184) at particular times in response to a visual stimulus. In FIG. 1Db, the distributions are displayed topographically (e.g., 186) over the same period of time. As will be apparent to one skilled in the art upon reading the present description, the group's distribution of visual resources is changing over the exemplary period of time (i.e., from left to right) from divergent to convergent (e.g., identifying an area of heightened attention). FIG. 1Dc shows the group's distribution of visual resources at each time and a plane (e.g., 190) at an average (e.g., mean or median) value of relative salience or height value.

FIG. 1Dd shows each plane (e.g. 190) and an area of maximal salience (e.g., 192) provided by the plane at each time. FIGS. 1De and 1Df further show the areas of maximal salience (e.g., 192) at any number of times. To generate a preferred display of the group's distribution of visual resources according to the present disclosure, the areas may be connected and/or extruded to develop an attentional funnel 195 over the period of time as shown in FIG. 1Dg. The funnel 195 may be mapped to the visual stimulus and portions (e.g., frame 197) of the visual stimulus included in the display to show the areas of the visual stimulus which correspond to the areas of maximal salience. As shown, a convergence is shown at the frame 197 indicating an area of heightened attention to the eyes of the male actor. FIG. 1Hd shows the frame 197 as well as two preceding frames leading up to the convergence.

Turning now to a description of the collection and assessment of blink data in connection with the experiment(s) described in the present disclosure, FIG. 2 illustrates an exemplary data collection and assessment process 200 as disclosed in the experiment(s) herein. Various aspects of the exemplary data collection and assessment process were utilized a plurality of times with the various test participants described herein. In one embodiment, the first parameter examined utilizing the process illustrated in FIG. 2 and commencing the present experiment(s) was overall blink rate and blink duration to test for physiological differences in eye-blink behavior between toddlers with ASD and typical toddlers. Eye movement data was recorded at the rate of 60 Hz, and blinks were recorded as events with a measurable duration, identified by an automated algorithm, supplemented and verified by simultaneous video recording in all participants (as described in step 204 of FIG. 2), and separately verified by simultaneous electromyography recordings in one adult viewer.

At the beginning of each test session, participants viewed a children's video (e.g., Baby Mozart, Elmo) played on a computer monitor (step 202 of FIG. 2). The computer monitor was mounted within a wall panel, and the audio soundtrack was played through a set of concealed speakers. Toddlers were seated and buckled into a car seat mounted on a pneumatic lift so that viewing height (line-of-sight) was standardized for all children. Viewers' eyes were 30 in (76.2 cm) from the computer monitor, which subtended approximately a 23°×30° portion of each child's visual field. Lights in the room were dimmed so that only images displayed on the computer monitor could be easily seen. A five-point calibration scheme was used, presenting spinning and/or flashing points of light as well as cartoon animations, ranging in size from 0.5° to 1.5° of visual angle, all with accompanying sounds. The calibration routine was followed by verification of calibration in which more animations were presented at five on-screen locations. Throughout the remainder of the testing session, animated targets (as used in the calibration process) were shown between experimental videos to measure drift in data. In this way, accuracy of the eye-tracking and eye blink data 112 was verified before beginning experimental trials and was then repeatedly checked between video segments as the testing continued. In the case that drift exceeded 3°, data collection was stopped and the child was recalibrated before further videos were presented. All aspects of the experimental protocol were performed by personnel blinded to the diagnostic status of the children. Most aspects of data acquisition and all aspects of coding, processing, and data summary are automated, such that separation between the diagnostic characterization protocol and the experimental protocol was assured.

To analyze blink inhibition as an index of perceived stimulus salience, children were shown a video scene of a boy and girl playing together in a toy wagon (some frames of which are shown FIG. 3). The video scene was excerpted from Karen Bruso and Mary Richardson's commercially available children's video, Toddler Takes! Take 1: Toddlers at Play. The video was presented in full-screen mode with an accompanying audio soundtrack on a 20-in (50.8 cm) computer monitor 140 (refresh rate of 60 Hz non-interlaced), according to step 202 in FIG. 2. Video frames were eight-bit color images, 640×480 pixels in resolution. The video frame rate of presentation was 30 frames per second. The audio soundtrack was a single (mono) channel sampled at 44.1 kHz. The original audio soundtrack contained an instance of adult narrator voiceover; this was removed digitally to make the video scene as naturalistic as possible. The duration of the video was 1 min and 13.6 s. Individual measures of blink rate and blink duration (see FIGS. 3 and 4) were measured during video watching, as opposed to during intertrial intervals.

Before and after the video, a centering cue was presented on an otherwise blank screen to draw the attention of viewers to common fixation location. The centering cue was 1.5° in visual angle with alternating blue and white sections, rotating in time to a chiming sound. During presentation of the centering cue, 91.4% of the children were compliant in looking at the cue; there were no between-group differences in the proportion of children who were compliant (z=1.12, P=0.24).

Visual fixation patterns were measured with eye-tracking equipment 110 using hardware and software created by ISCAN, Inc. (see step 204 of FIG. 2). The eye-tracking technology was video-based, using a dark pupil/corneal reflection technique with eye movement data collected at the rate of 60 Hz. Analysis of eye movements and coding of fixation data were performed with proprietary software written in MATLAB (MathWorks). The first phase of analysis was an automated identification of nonfixation data, comprising blinks, saccades, and fixations directed away from the stimuli presentation screen (see step 204 of FIG. 2). This eye tracking technology is exemplary only, and is not intended to limit the spirit or the scope of the present disclosure.

Blinks were identified by an automated algorithm measuring occlusion of the pupil by rate of change in pupil diameter and by vertical displacement of the measured pupil center. As will be understood and appreciated, other methods could be used to detect blinks, such as eyelid closure, certain eyelid movement, and the like. The blink detection algorithm was supplemented by simultaneous video re-cording in all participants and verified by manual coding of the video data in 10% of participants' data. The algorithm was also verified by simultaneous video and electromyography (EMG) recording in one adult viewer. In comparison with video recordings, the algorithm accurately detected 95.0% of all blinks identified by manual coding of video images. In comparison with EMG recordings, the algorithm accurately detected 96.4% of blinks recorded by EMG. Events identified by the algorithm as blinks but shorter than 166.7 ms or longer than 566.7 ms were excluded from analysis in accordance with previous studies of blink duration and in agreement with visual inspection of the video images (blinks in FIG. 7, which appear longer than 566.7 ms, are actually multiple blinks separated by brief fixations, obscured by the plot resolution). Duration measurements comparing blinks detected by the algorithm and blinks detected by EMG were different by less than 10 ms (i.e., less than the sampling detection threshold of the eye-tracker). Saccades were identified by eye velocity using a velocity threshold of 30° per second. Off-screen fixations, when a participant looked away from the video screen, were identified by fixation coordinates to locations beyond the screen bounds. Throughout all viewing data, the proportion of nonfixation data (saccades+blinks+off-screen fixations) was not significantly different between the ASD (M=24.25%, SE=1.2) and typical (M=24.7%, SE=1.5) groups [$t_{(91)}$=0.22, p=0.82] (see step 204 of FIG. 2).

No difference was found in blinks per minute (bpm) between toddlers with ASD (M=5.58 bpm, SD=3.88) and typical toddlers (M=5.18 bpm, SD=3.66) [$t_{(91)}$=0.519, P=0.60](FIG. 4). In addition, no difference in blink duration was found between toddlers with ASD (M=300.0 ms, SD=98.7) and typical toddlers (M=301.3 ms, SD=98.0) [$t_{(91)}$=−0.23, P=0.82]. Consistent with previous research on the ontogeny of blinking, individual blink rates (bpm) were positively correlated with chronological age in both groups (r=0.33, p<0.05 for the toddlers with ASD and r=0.27, P<0.05 for typical toddlers.) There was no between-group difference in the strength or direction of this correlation (z=0.28, P>0.05).

Figure 6A:
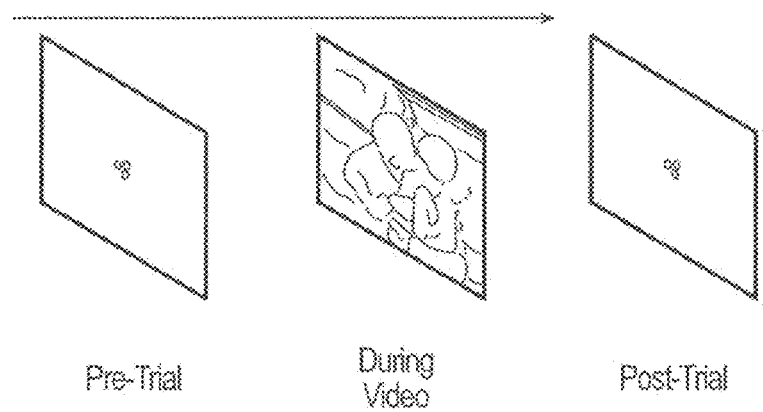
FIG. 6A illustrates an exemplary visual stimulus in connection with task dependent modulation of blink rate of typical toddlers and toddlers with ASD, according to one embodiment of the present disclosure.

Anecdotal observation of variation in blink rate during the intertrial intervals before and after each experimental trial (the video scene) (see FIG. 6A) was also tested. During these intervals, a centering cue was presented on an otherwise blank screen to draw the attention of viewers to a common fixation location. Based on earlier observations, by the indicators it was predicted that blink rate would decrease during the experimental trial relative to intertrial intervals.

Figure 6B:
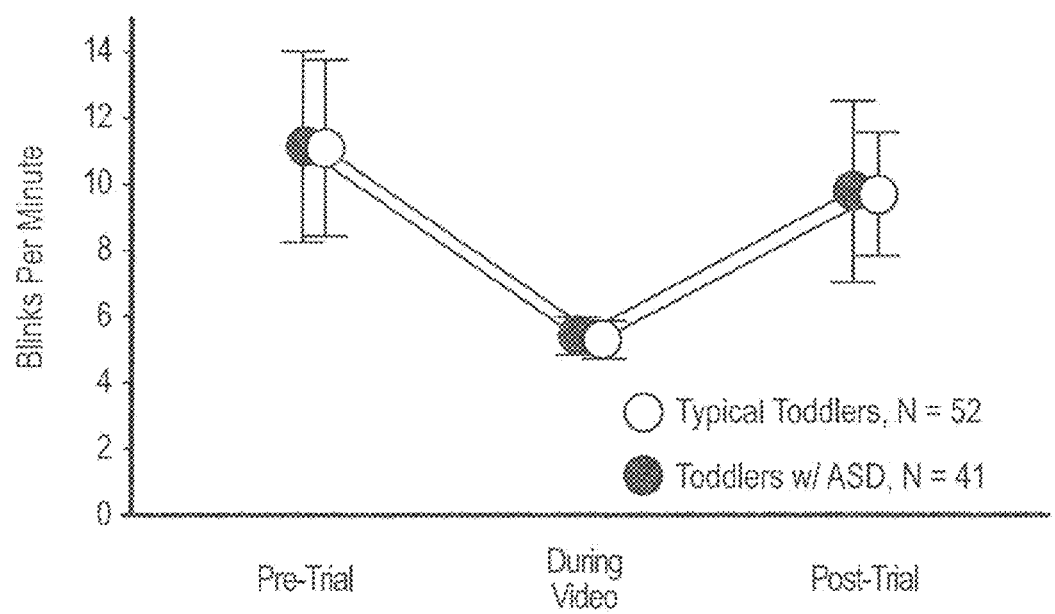
FIG. 6B illustrates task dependent modulation of blink rate of typical toddlers and toddlers with ASD, according to one embodiment of the present disclosure.

As shown in FIG. 6B, the mean blink rate of both toddlers with ASD and typical toddlers decreased during the experimental trial relative to pre- and post-trial periods. Given the positive skew of the dependent variable (bpm), with larger variance than mean, repeated measures of analysis of variance (ANOVA) [diagnostic group (2 levels)×trial type (3 levels: pretrial, during trial, and post-trial)] with underlying negative binomial distributions assumed was performed. The ANOVA yielded a significant main effect of trial type (Wald $X^2=18.70$, df=2, P<0.001). Post hoc comparisons indicated that mean bpm pre- and post-trial were not significantly different from one another (Wald $X^2=0.64$, df=1, P=0.42), but that blink rate during each of those conditions was significantly greater than blink rate during the experimental trial (Wald $X^2=20.58$, df=1, P<0.001 and Wald $X^2=14.57$, df=1, P<0.001, respectively). There was no main effect of diagnosis (Wald $X^2=0.002$, df=1, P=0.97) and no significant interaction of diagnosis by condition (Wald $X^2=0.003$, df=2, P=0.99).

A determination of instantaneous blink rate as it relates to the blink data was also tested. Instantaneous blink rate is computed as a density function. Data for each individual was recorded as 60-Hz time series. Binary values indicating whether a given individual was blinking or not were recorded at each point in the time series (0 for not blinking and 1 for blinking, with a contiguous sequence of 1's indicating a complete blink with duration equal to the length of that contiguous sequence) as described in 206 of FIG. 2. At each time, t, in the time series, instantaneous blink rate was calculated according to the following equation:

$$bpm_i(t) = \frac{1}{\Delta t} \times \frac{n_b(t)}{N_v(t)}$$

where bpm(t) is the instantaneous blink rate (blinks per minute) at time t, $\Delta t$ is the sampling interval (1/60 s for 60-Hz sampling, converted to minutes as 1/3,600 min), $n_b(t)$ is the sum of blinks (i.e., summed across individuals) occurring at time t, and $N_v(t)$ is the total number of viewers either blinking or looking at the screen at time t. Finally, the instantaneous blink rate density function was smoothed with a Gaussian window (300 ms at full-width half-maximum) selected to match the mean individual blink duration.

Note that in a free-viewing experiment(s), $N_v(t)$ should exclude any participant looking away from the screen at time t. Also, note that $n_b$ is a fractional count of total blinks: a single blink lasting 300 ms, measured in 60-Hz samples, would span 18 samples in the time series and would be counted as 1/18 of a blink at each time t.

Further, to test whether instantaneous blink rate was significantly modulated during the video watching, permutation testing was used. In each of 1,000 iterations, the binary times series blink data for each child (0=not blinking, 1=blinking) were permuted by circular shifting, following the equation:

$$b_{j,c}(t)=b_j(t-s_j, \text{modulo} T)$$

written as $$b_{j,c}(t)=b_j((t-s)_T),$$

which, for $s_j \geq 0$, equals $$b_{j,c}(t) = \begin{cases} b_j[t-s_j], & s_j < 1 \leq T \\ b_j[T-s_j+t], & 0 \leq 1 \leq s_j \end{cases}$$

where $b_j$ is the measured blink time series data for each participant, j; $b_{j,c}$ is the circular-shifted blink time series data for the same participant j; t is a time point in the time series defined over the interval $0 \leq t \leq T$; T is the total duration of the stimulus (in the present case, the duration of the entire movie shown to participants); and $s_j$ is the size of the circular shift, in the same units of time as t, for each participant j. The size of the circular shift for each participant was drawn independently from a random number generator with uniform distribution, with possible values ranging from −T to T. After circular shifting, for each iteration, i, instantaneous blink rate was calculated as previously described:

$$bpm_i(t) = \frac{1}{\Delta t} \times \frac{n_{b_c}(t)}{N_{v_c}(t)}$$

In this way, in each iteration, durations of blinks and interblink intervals were preserved for each individual but the timing of each blink was made random in relation to both the actual time line of video content and in relation to the timing of other participants' blinking. By this approach, in the permuted data, the mean blink rate of participants during the entire task remains unchanged (and task-specific), but the timing of when instantaneous blink rate is increased or decreased is made random.

The permutation process was repeated on 1,000 iterations and then measured against the statistical distribution of blink rate across all iterations at each point in the time series. At each time point across all iterations, the fifth percentile of permuted data was used as a nonparametric threshold for identifying time points of significant blink inhibition. This enabled the comparison of actual patterns of eye blinking to randomized, chance patterns of eye blinking, enabling the null hypothesis that the timing of eye blinks was unrelated to scene content to be tested.

Based on the experiment(s) above, it was found that the blink rate for typical toddlers was significantly inhibited exhibiting values less than the 0.05 threshold of shuffled data) during 8.8% of video viewing time and that the blink rate for the ASD group was significantly inhibited during 7.0% of viewing time. The difference between observed blink rates and permuted data for each group was tested by two-sample Kolmogorov-Smirnov tests, finding significant differences for each (D=0.22, P<0.001 for typical toddlers and D=0.28, P<0.001 for toddlers with ASD).

FIG. 9 shows graphs of the empirical cumulative distribution functions comparing actual blink data with permuted data. These plots show both an increase in low blink rates (the gap between actual data and permuted data at the left end of abscissa) as well as an increase in blink rates (gap between actual data and permuted data at the right end of abscissa).

It was tested whether instantaneous blink rate was significantly modulated during the video itself (see FIG. 7A). Individual data were recorded as 60-Hz time series (with binary values at each point in the series indicating whether a given individual was blinking or not). Instantaneous blink rate was computed across all individuals for each group. To test the null hypothesis that the timing of blink inhibition was unrelated to scene content, permutation testing was used. In each of 1,000 iterations, for each group, the binary times series blink data for each child were permuted by circular shifting, with shift size for each child drawn independently from a random number generator with uniform distribution. Instantaneous blink rate was then calculated across the shifted individual data. Because each individual's data had been shifted independently, the timing of each shifted blink time series was random in relation to the actual time line of video content and random in relation to the timing of other participants' blinking. By this approach, in the permuted data, the mean blink rate of participants during the entire task remains unchanged (and task-specific), but the timing of when instantaneous blink rate is increased or decreased is made random.

This enabled a basic permutation test with exact probabilities: at each time point, the fifth percentile across all permuted data served as a statistical threshold (P=0.05) for identifying periods of statistically significant blink inhibition (see FIGS. 7C and 7D). If the timing of actual measured blinks was random with respect to ongoing video content, it was expected that the measured instantaneous blink rate for each group would differ from that of the permuted data no more than 5% of the time. In contrast, in the actual data, it was found that the blink rate for typical toddlers was significantly inhibited (exhibiting values less than the 0.05 threshold of permuted data) during 8.8% of video viewing time and that the blink rate for the ASD group was significantly inhibited during 7.0% of video viewing time. This difference was tested between observed blink rates and permuted data for each group by two-sample Kolmogorov-Smirnov tests, finding significant differences for each (D=0.22, P<0.001 for typical toddlers and D=0.28, P<0.001 for toddlers with ASD).

As part of the correlation of blink inhibition to the visual stimulus 120, a plurality of segments of the visual stimulus was identified as affective content and physical content (also referred to herein as affective events and physical events). Ten adults rated the affective content of the video scene in a two-stage process. First, the entire video was divided into 15 segments, and viewers were asked to rank the segments from most affective to least affective. Interrater coefficient of concordance for these rankings was highly significant (Kendall's W=0.879, $X^2$=123.02, df=14, P<0.0001). The eight segments ranked most highly were then used to identify precise timing of the affective events. To do so, adult raters examined each of the eight most affective segments frame-by-frame and selected the time point at which the affective event began and the time point at which the affective event ended. The SE of start and end times across all raters was 152 ms. Start and end times for each affective segment were averaged across the 10 raters, resulting in eight affective events. Physical events were defined as all-time points in which a wagon door was moving (with start and end points set by the start and stop of the door's motion). As will be generally understood by one of ordinary skill in the art, events do not necessarily have to be categorized as affective or physical events, and such categorizations are merely used as exemplary purposes for the present experiment(s) and disclosure. Furthermore, a plurality of mechanisms may be utilized for determining and measuring changes in blink rate in relation to any kind of event.

Having confirmed that blinking was inhibited at levels greater than expected by chance and inhibited at specific times during unconstrained viewing of natural scenes, it was tested whether blink inhibition varied selectively with respect to video content, visual fixation, and viewer group. As described above, the experimental paradigm presented two categories of content (affective and physical events) to two populations of children known for differential attention to those categories (children with ASD and typical toddlers). In the video shown to participants, the boy in the video desires to leave the wagon door open, whereas the girl wants it to be closed; this scenario conveniently created varying levels of affective content (the discord between the boy and the girl) and a repeated physical action (the closing or opening of the wagon door).

To operationalize the designation of affective and physical events in a video of unscripted natural interaction, 10 adult viewers rated the level of affect throughout the entire video, identifying eight segments within the video in which facial expressions and/or vocalizations showed heightened emotional affect (e.g., time periods when the boy or the girl in the video became visibly angry). The coefficient of concordance for interrater affective ranking was highly significant (Kendall's W=0.879, $X^2$=1223.02, df=14, P<0.00001). Physical events were operationalized as times when the wagon door was moving. The two event types were not mutually exclusive but, per the independent raters, overlapped less than 25.18% of the time.

The remaining segments of the video were classified as nonaffective/nonphysical events. It was predicted that viewers would inhibit their blinking during moments perceived to be particularly important to process and would increase their blinking during moments perceived to be less important. To examine how the timing of blink inhibition varied with respect to affective and physical events, peristimulus (or "perievent") time histograms (PSTHs) were used. PSTHs were constructed by aligning segments of individual time series blink data to the onset of events and by then computing counts of an individual's blinks occurring in 33.3 ms bins in a surrounding 2,000 ms window (as shown in step 208 in FIG. 2). Bin counts were computed for each participant across all events and then averaged across all participants to obtain group means.

To test whether the observed changes in blink rate differed from those expected by chance, a second set of PSTHs from permuted blink data was computed. As before, individual blink sequences were permuted by circular shifting of individual data 1,000 times. PSTHs were then computed on each of those permuted datasets. The mean instantaneous blink rate, during each bin, across all 1,000 PSTHs from permuted data quantified the blink rate one would observe if blink rate were random with respect to onscreen events. If, on the other hand, blink rate were time-locked to onscreen events and not random, one would expect to see significant deviations from the permuted data distribution. The 5th and 95th percentiles of instantaneous blink rate across all PSTHs from permuted data served as a P=0.05 confidence level against which to compare blink rates in the actual data (one-tailed comparisons). To test for between-group differences, confidence intervals (CIs) of bootstrapped data for each group were computed, as noted in step 216 of FIG. 2.

Figures 8A, 8B, 8C:
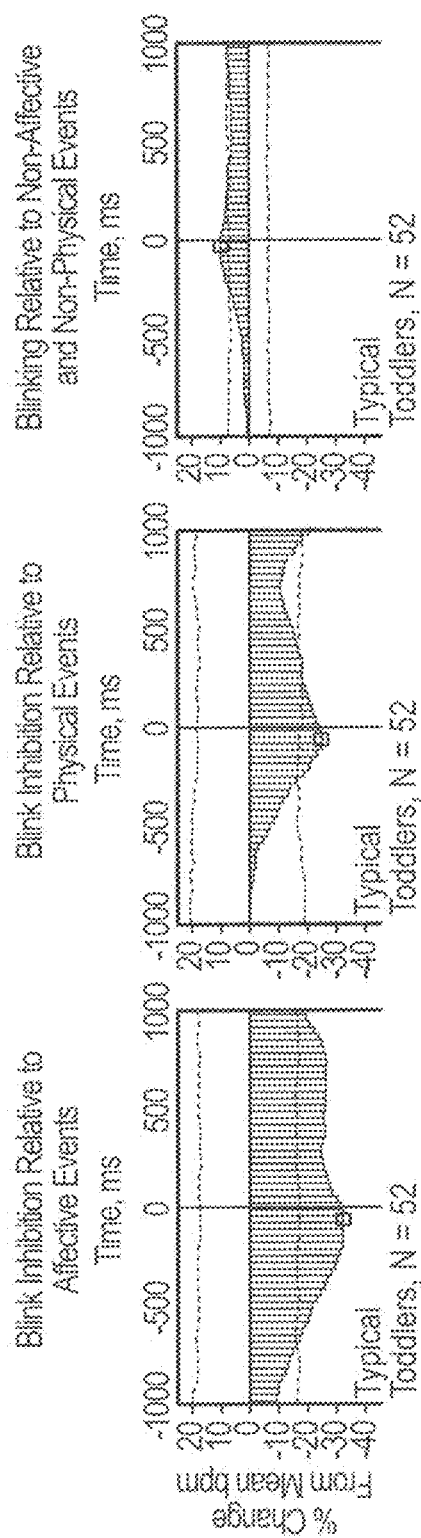
FIG. 8A is a graph illustrating blink inhibition relative to affective events for typical toddlers, according to one embodiment of the present disclosure.
FIG. 8B is a graph illustrating blink inhibition relative to physical events for typical toddlers, according to one embodiment of the present disclosure.
FIG. 8C is a graph illustrating blink response relative to nonaffective and nonphysical events for typical toddlers, according to one embodiment of the present disclosure.
Figure 8F:
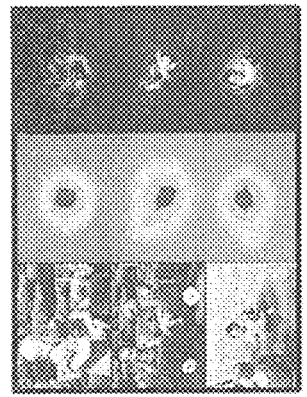
FIG. 8F illustrates exemplary visual fixation relating to nonaffective and nonphysical events for typical toddlers, according to one embodiment of the present disclosure.
Figure 8E:
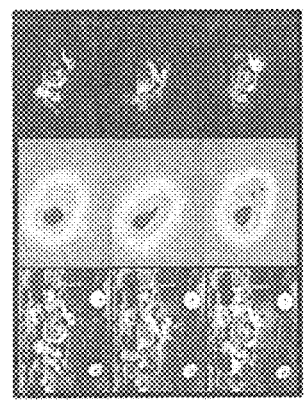
FIG. 8E illustrates exemplary visual fixation relating to physical events for typical toddlers, according to one embodiment of the present disclosure.
Figure 8D:
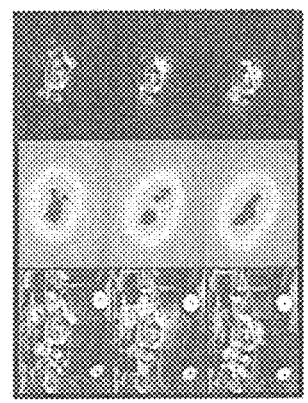
FIG. 8D illustrates exemplary visual fixation relating to affective events for typical toddlers, according to one embodiment of the present disclosure.

As shown in FIG. 8A and described in step 218 of FIG. 2, the PSTH for typical toddlers reveals a 32.4% reduction in blink rate for affective events, reaching its minimum 66 ms prior to the zero lag. This indicates statistically significant blink inhibition in typical toddlers (P<0.05), time-locked to the occurrence of events with high affective valence. Toddlers with ASD also show a reduction in blink rate (35.8%), but that reduction is greatest 599 ms after the zero lag of affective events (see FIG. 8G).

The between-group difference in timing is highly significant, because the CIs of bootstrapped lag data for each group are nonoverlapping (see FIG. 8M, lag time for blink rate minimum in typical toddlers: $CI_5$=−230 ms, $CI_{95}$=0 ms; lag time for blink rate minimum in toddlers with ASD: $CI_5$=33 ms, $CI_{95}$=700 ms). The observed difference in timing was not attributable to a more general delay in speed or frequency of eye movements, because it was found that no between-group differences in latency to shift gaze [typical toddler: M=1.09 s (SE=0.20), toddlers with ASD: M=0.96 s (SE=0.28); $t_{(91)}$=0.40, P=0.69, measured as reaction time to initiate a first saccade following the onset of the movie] or in duration or frequency of fixations [duration for typical toddlers: M=442 ms (SE=16.4), duration for toddlers with ASD: M=492 (SE=29.4); $t_{(91)}$=−1.57, P=0.12 and frequency for typical toddlers: M=2.04 fixations per second (SE=0.09), frequency for toddlers with ASD: M=1.93 (SE=0.11); $t_{(91)}$=0.85, P=040].

Each group shows a numerical, although not statistically significant, reduction in blink rate by event type (see FIG. 8N): Typical toddlers exhibit greater reduction in blink rate during affective than physical events (32.4% vs. 25.4%, FIGS. 8A and 8B), whereas toddlers with ASD exhibit the reverse pattern, with a 41.7% reduction for physical events and a 35.8% reduction for affective events (see FIGS. 8G and 8H). Both groups of toddlers show a significant increase in blink rate relative to nonaffective nonphysical events (see FIGS. 8C and 8I). Helping to disambiguate the question of differential engagement is the pattern of each group's visual fixations during the two event types (see FIG. 8O). Typical toddlers spent significantly less time looking at objects than toddlers with ASD during both event types [$F_{1,91}$=12.01, P=0.001, repeated measures ANOVA with diagnosis (2 levels)×event (affective vs. physical)], and the interaction between diagnosis and event type was significant (see FIG. 8O) ($F_{1,91}$=5.99, P=0.016). Paired-samples t tests confirmed that typical toddlers showed no difference in percentage of fixation on objects during affective vs. physical events ($t_{1,51}$=0.85, P=0.4; $M_{affective}$=25.5%, SD=14.21 vs. $M_{physical}$=26.5%, SD=16.7), but that toddlers with ASD increased fixation on objects, such as the moving wagon door, during physical events (see FIG. 8O) [M (SD)=33.9(16.7) for affective vs. 40.0(17.2) for physical; $t_{1,40}$=3.57, P=0.001].

In sum, blink inhibition for typical toddlers was (i) most reduced just prior to the zero lag of events, (ii) numerically greater for affective rather than physical events, and (iii) unrelated to level of fixation on objects (marked instead by greater than 73% fixation on people during both event types). In contrast, for toddlers with ASD, blink inhibition was (i) most reduced after the zero lag of events, (ii) numerically greater for physical rather than affective events, and (iii) marked by a significant increase in fixation on objects during physical events (see step 220 of FIG. 2).

Figure 6C:
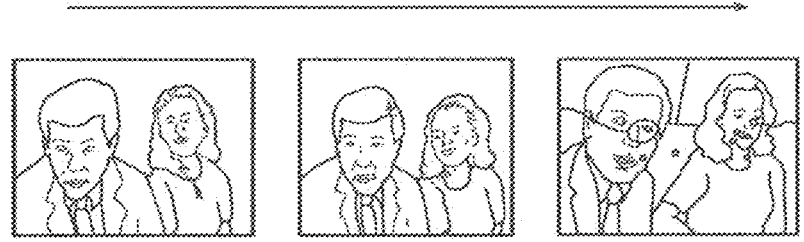
FIG. 6C illustrates an exemplary visual stimulus in connection with task dependent modulation of blink rate of typical toddlers and toddlers with ASD, according to one embodiment of the present disclosure.
Figure 6D:
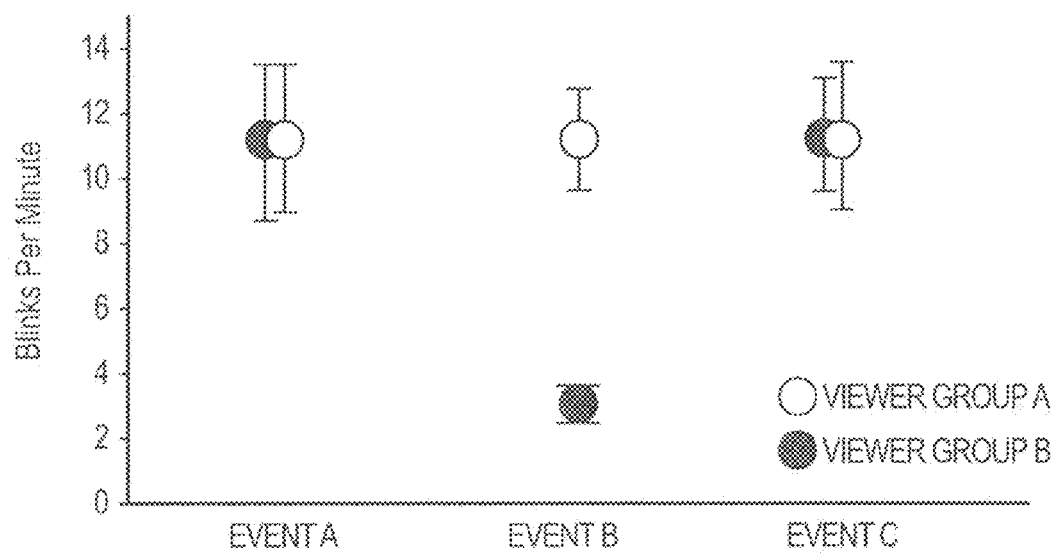
FIG. 6D illustrates task dependent modulation of blink rate between two different viewer groups, according to one embodiment of the present disclosure.

Referring now to several of the figures, in one embodiment, FIG. 6C illustrates an exemplary embodiment of task dependent modulation of blinking between two different viewer groups (viewer group A and viewer group B), in particular, an exemplary blink rate comparison between two different viewer groups (see FIG. 6E) observing three different event stimuli (see FIG. 6D). In one embodiment, viewer group A and viewer group B do not exhibit blink inhibition while viewing event A. According to one aspect and as illustrated in FIG. 6C, as both viewer groups engage with event A, neither group inhibited their blink rate as both groups' bpm remained between approximately 9 and 13 blinks per minute.

According to one aspect illustrated in FIG. 6C, in connection with event B, viewer group B's blink inhibition is modulated while the viewer group engages with event B of the visual stimulus. Alternatively, viewer group A's blink inhibition is not modulated and generally hovers around 9-13 blinks per minute. In one aspect, this demonstrates that viewer group B's level of engagement notably increases during engagement with event B; whereas viewer group A's level of engagement generally does not change.

Further, in another aspect, both viewer groups' levels of engagement remain consistent during the viewing of event A within the visual stimulus. Blink inhibition remains relatively close for both viewer groups around 9-13 blinks per minute. The discussion example of FIG. 6C demonstrates various levels of engagement amongst groups of people in response to certain events (e.g., events within a given stimulus, or between different stimuli entirely, etc.). For example, a marketing firm may use such an assessment in determining a marketing campaign's power to engage a target demographic. Accordingly, if a marketing campaign is intended to target a demographic of 30-40-year-old women, specifically during predetermined segments of a visual stimulus, viewer group A may comprise 30-40-year-old men and viewer group B may comprise 30-40-year-old women. If event B comprises the predetermined segment designed to captivate individuals belonging to viewer group B, then in this exemplary description the marketing campaign may be successful at increasing the level of engagement (assessed by measuring blink rate and blink inhibition) for viewer group B during event B. As will be generally understood, the aforementioned description is for exemplary purposes and is not intended to limit the spirit or scope of the present disclosure.

FIG. 7 illustrates an exemplary representation of statistically significant blink inhibition during natural viewing of a video scene, wherein data are plotted over time such that a time-lock with the visual stimulus occurs for further analyzation of the blink data, according to one embodiment of the present disclosure. In one embodiment, FIG. 7A illustrates an exemplary raster plot depicting eye blinks made by typical toddlers while watching an exemplary video scene. Similarly, in another embodiment, FIG. 7B illustrates instantaneous blink rate time-locked with the visual stimulus. According to one aspect, the higher points in the curve of FIG. 7B represent where viewers exhibited significant amounts of blinking (e.g., generally points closer to 17-20 blinks per minute) whereas points in the curve that are lower represent points in time where the viewer did not blink as often (e.g., generally points closer to 0-2 blinks per minute).

In another embodiment, FIG. 7C illustrates an exemplary plot of the $5^{th}$ and $95^{th}$ percentiles of permuted data (mechanisms for determining permuted data were previously discussed in further detail herein) for typical toddlers. In one aspect, the 95th percentile represents increased blinking and the 5th percentile represents decreased blinking. Plotted data shown in FIG. 7C that corresponds to the 5th percentile of instantaneous blink rate are used to generate FIG. 7D, wherein FIG. 7D illustrates an exemplary plot of instances of blink inhibition mapped (synchronized) with particular times in the video scene according to another embodiment of the present disclosure. As shown in FIG. 7, corresponding times of blink inhibition 705, 710, 715, and 720 can be seen in each of the plots of FIGS. 7A-D. Similarly, various mechanisms associated with time-locking a visual stimulus to blink data, an auditory stimulus may be time-locked with blink data to further determine periods of blink inhibition as it relates to the auditory stimulus.

FIG. 8 illustrates exemplary data in connection with time-locked (synchronized) blinks and blink inhibition during natural viewing, together with example visual fixation data, according to one embodiment of the present disclosure. In some aspects, the present experiment(s) measured time-locking of blinks and blink inhibition relative to affective events (see FIGS. 8A and 8G), physical events (see FIGS. 8B and 8H), and nonaffective/nonphysical events (see FIGS. 8C and 8I) by constructing PSTHs. PSTHs show the percent change in bpm relative to the mean of permuted blink data. Dashed horizontal lines mark 0.05 and 0.95 CIs; the percent change in bpm beyond these levels represents a change in bpm greater than expected by chance (one-tailed, P<0.05).

CIs scale inversely with the number of events (with approximately double the number of events in the nonaffective nonphysical category).

According to further aspects, absolute minimum and maximum changes in bpm are highlighted by black squares in each plot. Exemplary visual fixation data during changing in blink rate for typical toddlers and toddlers with ASD are illustrated relating to affective event in FIGS. 8D and 8J, relating to physical events in FIGS. 8E and 8K, and relating to nonaffective/nonphysical events in FIGS. 8F and 8L, respectively. Three column plots show a still frame from the video (first column, sampled at the absolute minimum decrease in bpm); kernel density plot of fixation data at the same moment (second column, with hotter colors denoting greater density); and the same kernel density plot scaled from black to transparent, overlaid on the original frame (third column). The color of fixation density plots is scaled relative to the sample size of each group, such that maximum and minimum possible densities have the same color values for each group despite differences in sample size. FIG. 8M illustrates timing of blink inhibition for affective vs. physical events. FIG. 8N illustrates percent decrease in bpm for affective vs. physical events. FIG. 8O illustrates percent fixation on objects for affective vs. physical events.

FIG. 10 illustrates an overview 1000 of an exemplary process for determining the level of viewer engagement activity with respect to a given stimulus. The exemplary determination of viewer engagement activity process utilizes similar mechanisms as described in connection with FIG. 2. For example, the process generally initiates by displaying a visual stimulus to a viewer (see step 1002). As previously described, a visual stimulus may comprise a plurality of forms of media including: a DVD, stored digital media, a video game, etc. Subsequently, a processor 102 receives and records blink data (see step 1004) corresponding to a viewer while simultaneously receiving stimulus data 122 that corresponds to the visual stimulus. Blink data is generally captured via an eye tracker or eye-monitoring device 110 before propagating to the processor. The processor typically comprises software enabling the blink data to be transformed to a usable, assessable format as executed in process 1006.

Further, the processor 102 generally comprises software to time-lock stimulus data 122 to a usable and assessable format of blink data (see step 1008). As previously discussed, time-locking blink data with stimulus data 122 enables assessment of blink behavior and blink inhibition relative to various indicators within the visual stimulus. In some instances, the process of determining viewer engagement activity may involve gathering data for one or a plurality of viewers, wherein generally for assessing a plurality of viewers the aforementioned steps 1002-1010 are repeated until the desired group of viewers is attained. Furthermore, viewers may be categorized into various demographics according to the intent and spirit of the target experiment(s) (step 1012). For example, an illegal-substance screening stimulus may be created, wherein a viewer is tested for their level of engagement as he or she views various illegal substances to potentially categorize as a user or ex-user of illegal substances.

Additionally at step 1014, the processor 102 generally comprises software to aggregate time-locked or synchronized blink data, for example, by combining and permuting the data for many viewers. In one embodiment, the aggregated time-locked blink data is generally assessed for a plurality of indicators including: determining an individual's instantaneous blink rate, the probability of whether an individual blinked or will blink, etc. Generally, these indicators are synchronized with one or multiple points in time with respect to the visual stimulus 120. Utilizing the aggregated and parsed blink data, the results are assessed to identify various patterns of blink inhibition (see step 1016) and compared with predetermined indicators within the stimulus data and other predetermined factors (see step 1018). Subsequently, a general assessment can be made regarding the viewer(s) level of engagement as it relates to various events within the visual stimulus (see step 1020). For example, when engaging a viewer regarding an illegal substance screening, a drug user may vary his or her level of engagement or blink timing when shown an illegal substance versus someone who does not use illegal substances.

In one embodiment, FIG. 10 may also describe a similar process for determining engagement activity as it relates to listening to an auditory stimulus, wherein step 1002 a listener hears/listens to an auditory stimulus. Accordingly, the remaining steps of the process described in FIG. 10 would generally be similar to those utilized for a visual stimulus. Similarly, a listener's measure of blink inhibition determines the listener's level of engagement to the auditory stimulus. For example, teachers may want students to listen to an auditory stimulus for teaching a foreign language. The teachers may utilize this exemplary process to assess how engaged students are to the teaching aid.

According to one embodiment of the present disclosure, FIG. 11 illustrates an overview of an exemplary process 1100 for categorizing or rating viewers as a function of their engagement with a given stimulus for assessing disease/disorder state, wherein the assessment of disease/disorder state generally comprises the presence/absence of a condition, disease/disorder state progression, and/or treatment response in connection with a prior diagnosis. Similar to some other processes in the present disclosure, the process for assessing disease/disorder state 1100 generally commences with displaying a visual stimulus (see step 1102) to a viewer on a monitor device 140, receiving and recording at the processor 102 blink data for the viewer (see step 1104), and conversion of blink data to assessable format (see step 1106) at the processor.

The processor 102 retrieves predetermined time-stamped event data (step 1108) corresponding to the visual stimulus 120 from the database 130. The predetermined time-stamped event data may relate to a number of parameters. For example, the data may comprise control data describing patterns of time moments at which either typical or atypical viewers heighten or lessen their level of engagement according to various event indicators. For example, the time stamped events could relate to physical or affective events in the visual stimuli. The recorded viewer blink data is then time-locked to the visual stimulus and compared to the predetermined time-stamped data (see step 1110) to identify various patterns of blink inhibition and further to determine levels of engagement throughout the visual stimulus. Further in certain embodiments (described in greater detail below), in addition to comparing the level of engagement at particular points in time, a comparison is made to locations of visual fixation according to various times within the visual stimulus. The comparison can be used for identifying areas of convergence and divergence within the data sets such that an assessment may be generated to determine if the viewer's blink data exists within/outside of the limits of the predetermined ranges of acceptable data (see step 1112). Subsequently, a further assessment can be made (see step 1114) as to the disease/disorder state of the viewer utilizing the comparison of the control data and the viewer's blink inhibition data. For example, if blinking is inhibited before a predetermined event, then a toddler may be categorized as typical, but if blinking is inhibited after a predetermined event, then a toddler may potentially show early signs of ASD.

As will be generally understood by one of ordinary skill in the art, typical toddlers and toddlers diagnosed with ASD were assessed during the experiment(s) described by aspects of the present disclosure, but any viewer group may be targeted and analyzed for various levels of viewer engagement using the disclosed mechanisms of gathering and analyzing eye data. For example, a viewer group may comprise a group of teenagers for marketing research, a group of college students for a psychology experiment(s), a group of adults for medical testing, etc.

The process described in connection with FIG. 11 may also be utilized to rank and/or categorize viewers depending on a viewer's level of engagement. In one embodiment, based on the assessed level of engagement of a viewer, a further assessment may be made in connection with categorizing the viewer. In one aspect, utilizing blink data it is possible to determine a viewers' level of engagement with a stimulus, wherein the various levels of engagement may provide a viewer ranking or maybe further used in conjunction with a predetermined index to classify or categorize viewers. For example, a flight simulator may be developed to engage potential flight school candidates and generate reports that assess and categorize the potential candidates according to a potential success rate for flight school.

According to one aspect similar to the process described in connection with FIG. 11, in connection with categorizing a viewer or group of viewers as a function of their engagement with a given stimulus, steps 1102-1112 can be repeated for gathering and comparing blink data. Accordingly, similar to step 1114, an assessment as to a viewer's index level, rating, or category can be provided as a function of viewer engagement. For example, students in a school may be classified based on their level of engagement with a lecture, such that teachers would know and understand which students need more attention based on their engagement level.

In one embodiment, FIG. 11 may also describe a similar process for assessing/categorizing as it relates to listening to an auditory stimulus, wherein step 1102 a listener hears/listens to an auditory stimulus. Accordingly, the remaining steps of the process described in FIG. 11 would generally be similar to those utilized for a visual stimulus. Similarly, a listener's measure of blink inhibition determines the listener's level of engagement to the auditory stimulus. For example, an auditory stimulus may comprise a mechanism for assessing the disease/disorder state of various individuals. As predetermined blink patterns may be known, if a listener does not follow or correlate with the predetermined blink data, the individual may be categorized into a certain group as it relates to a state of a mental disease/disorder/condition. Further a mental disease/disorder/condition may comprise a cognitive or developmental disease/disorder/condition.

In one aspect similar to the process describe in connection with FIG. 11, concerning analyzing the measure of a stimulus's ability to engage a viewer, the blink data may be compared to a predetermined index that correlates viewer engagement to a stimulus's power to engage a viewer or group of viewers. In another aspect, the processor 102 may retrieve predetermined time event data and using an algorithm to determine a stimulus's ability to engage viewers. For example, a marketing company may have a predetermined viewer engagement index the dictates the prediction of success of a marketing campaign. During trial showings of various marketing campaigns, if the marketing campaign does not reach the minimum predetermined viewer engagement index by successfully engaging viewers, it will not be released for marketing.

According to another embodiment, blink inhibition data may provide a quantifiable metric for the level of effectiveness a visual stimulus may have by utilizing a measure of perceived visual salience. In one aspect, effectiveness of a visual stimulus may comprise using an index of viewer engagement to determine whether the visual stimulus possesses the desired or undesired effect of captivating a viewer. As previously described and according to one aspect, the level of viewer engagement may be analyzed with blink data and time-locked with particular points in the visual stimulus (e.g., frame-by-frame, predetermined segments, etc.). Therefore, according to one aspect, determining the level of engagement of a viewer at particular points will assist in determining how engaging a visual stimulus is at that particular point or segment to an audience or viewer. Similarly, level of engagement of a viewer may help to identify the effectiveness of a whole or complete visual stimulus at captivating an audience or individual. For example, a marketing company may utilize level of engagement trends via capturing measures of blink data during trial testing of marketing campaigns as an indication of the campaign's ability to engage. A marketing company may also utilize blink data to determine whether stimulus A is more effective than stimulus B to verify unproven/untested theories.

In one embodiment, blink inhibition data can be utilized a similar process for determining the power of an auditory stimulus's power to engage as it relates to a listener listening to an auditory stimulus, wherein the initial step a listener hears/listens to an auditory stimulus. Accordingly, the remaining steps of the aforementioned processes would generally be similar to those utilized for a visual stimulus. Similarly, a listener's measure of blink inhibition determines the listener's level of engagement to the auditory stimulus. For example, teachers may want students to listen to an auditory stimulus for teaching a foreign language. The teachers may utilize this exemplary process to assess how engaged students are to the teaching aid.

In one embodiment and as previously described, blink data correlated with viewer level of engagement that is used to categorize a viewer may be further used in connection with determining effectiveness of a visual stimulus. For example, a particular visual stimulus may be targeted for 10-14-year-old girls. By testing a sample of a target audience, blink data may further assist in identifying effectiveness of the visual stimulus intended for a target audience. Further, a comparison may be made between 6-10-year-old girls and 10-14-year-old girls for example, to ensure the accuracy of viewer engagement.

FIG. 12 illustrates one embodiment of the present disclosure comprising an exemplary process 1200 for collecting and assessing various types of data including assessing perceived stimulus salience of a visual stimulus. In one aspect, the eye tracker 110 may comprise a combination of an eye tracker and a blink monitor, wherein the eye tracker records eye movement data (e.g., saccades, fixations, pupil dilations, etc.) and the blink monitor records blink data. In another aspect, the eye monitoring system may comprise a separate eye tracker and blink monitor working in conjunction to send eye and blink data 112 to the processor 102 for assessment. According to one aspect of the present embodiment, eye data 112 received by the processor 102 (see step 1205) can be utilized to create attentional funnels (as previously described herein) for quantifying and mapping visual salience to further assess a viewer's level of engagement.

As previously described, the eye tracker may receive and record blink data and eye data similarly to other processes described in the present disclosure (see steps 1204 and 1205). Eye movement and blink data can be converted to assessable formats (see step 1206), such as binary blink data and point of regard (point-of-gaze) coordinate data and the processor 102 can retrieve predetermined time stamped events for the visual stimulus 120 (see step 1208). Similar to the process described in connection with FIG. 2, eye and blink can be collected for many viewers in a group and the viewers can be optionally categorized based on desired engagement demographics or other category criteria (see steps 1210 and 1212).

Accordingly, the processor 102 can create a mapping of perceived visual salience, compare time-locked eye data to predetermined data, and provide an assessment of perceived stimulus salience. In one embodiment, a quantified mapping of perceived visual salience describes a viewer's fixation or point of regard, wherein the point generally determines the location on a stimulus one focuses his or her attention. In one aspect, eye data 112 corresponding to a control group or control data can be used to create an attentional funnel (previously described in connection with FIG. 1D) delineating areas of convergence and divergence. As previously described, areas of convergence generally represent particular instances in time where the majority of viewers distribution of point of regards are within a small two-dimension area on a stimulus. This data and/or display can be overlaid or time-locked to blink data for the same stimulus, which enables confirming diagnostic methods, etc. This mechanism is utilized to assess viewers who do not follow the distribution of convergence and further may be able to provide an assessment of disease/disorder state.

In one embodiment illustrated in FIG. 13, a process 1300 is illustrated for identifying the most engaging temporal and spatial features within a stimulus. Similarly to the process described in FIG. 12, a stimulus may be displayed to one or more viewers (step 1302), eye-movement and blink data may be recorded (steps 1304 and 1305) and converted to an assessable format (step 1306), and the eye-movement and blink data can be time synchronized to the visual stimulus (step 1308). Further, the time-locked eye and blink data may be permuted to quantify the probability of blink response during the viewing of the visual stimulus for participating viewers (see step 1312). As previously described, permuting blink data enables an accurate analysis of blink response; hence, enabling periods of blink inhibition to be identified for a given viewer or group of viewers (see step 1314).

Through the aforementioned process of quantifying visual salience, the eye-movement data is assessed to determine areas of fixation and correlated with periods of blink inhibition to identify the most engaging temporal and spatial features of a visual stimulus (see steps 1316 and 1318). In particular, if it is assumed a viewer is engaged with a video exhibiting blink inhibition, then identifying location of fixation data may indicate spatial and temporal locations of the video that are most engaging. Through a "data-mining" process executing numerous trials to collect a plurality of data, assessing the level of viewer engagement to a visual stimulus, and specifically to various features within the stimulus, can help assess the most engaging temporal and spatial features of the stimulus based on time-varying viewer engagement.

FIG. 14 illustrates an exemplary process 1400 of assessing patient condition state, according to one embodiment of the present disclosure. Similarly to the process described in connection with FIG. 11, blink data is recorded (step 1404), converted to assessable format (step 1406), and compared to time-stamped events to identify various blink patterns (step 1410). A further assessment regarding the level of blink patterns relative to predetermined ranges is conducted to identify severity, mildness, or change of condition state (see step 1412). For example, a viewer may be previously diagnosed with a cognitive condition and is routinely assessed to monitor the state of that cognitive condition. Further, the predetermined data that the newly acquired blink data is compared to may comprise previous data from the viewer at an earlier stage of his or her diagnosed condition. According to the measure of condition severity, longitudinal data may be collected to determine the measure of change in the state of the present condition (see step 1416).

Further Analysis

According to some embodiments of the present disclosure (in particular, the experiment(s)s described above), patterns of blink inhibition and the distribution of visual fixations map onto well established between-group differences, but also reveal more subtle differences in the subjective assessment of stimulus salience. For example, according to one aspect, when data were time-aligned to scenes of heightened affective content (FIG. 6A), typical toddlers showed a persistent inhibition of blinking that peaked before the zero event lag. Toddlers with ASD, in contrast, exhibited a peak in blink inhibition that occurred more than 0.5 s after the zero event lag.

That typical toddlers inhibit their blinking earlier than toddlers with ASD shows the unexpected possibility that typical toddlers are actively anticipating the unfolding of salient events, and are doing so in time-locked fashion. The visual fixation data tell a similar story: Toddlers with ASD look more at physical objects in the video scene and selectively increase their fixation on those objects when the objects move (that is, during the designated physical events). Accordingly, utilizing time-locked blink inhibition and/or visual fixation data can be used in assisting diagnosis of various cognitive disorders or degradations.

In contrast, typical toddlers' attention to socially relevant cues, such as eye-gaze, facial expression, and body posture, may allow them to anticipate actions that have not yet happened but may be about to happen (as when angry facial expressions precede a yell or the slamming of the wagon door). These cues help typical toddlers generate expectations about how actions in the world will subsequently unfold. For toddlers with ASD, however, blink inhibition, as an after-the-fact reaction, can be seen as reflecting a lack of sensitivity to those environmental (and, in particular, social) cues. It suggests an engagement with affective and physical stimuli separate from the social context in which they are typically perceived: although typical toddlers may be engaged by the slamming of the car door because of its relevance to the ongoing social interaction between the characters, engagement by toddlers with ASD may be in reaction to the salient physical properties of such events.

These hypotheses regarding between-group differences in how movie events were perceived underscore the point that even though movie events may be classified as affective or physical, it is unlikely that they were perceived as mutually exclusive dualities. One of the main goals of the experiment (s) was to test for blink inhibition using semi-structured, naturalistic stimuli. In such situations, categorical boundaries of affective and physical become blurred: typical toddlers, for instance, are likely to perceive the social significance and affective meaning behind the slamming wagon door. This blurring of affective and physical categories may account for why reductions in blink rate trended in the expected directions but did not reach statistical significance in this particular analysis, with typical toddlers showing a larger reduction in response to affective events, whereas toddlers with ASD showed greater reduction to physical events. Further, events do not necessarily have to be categorized into either affective or physical events to determine a level of engagement, as will be understood by one of ordinary skill in the art.

The results demonstrate that patterns of blink inhibition can provide an inroad into an aspect of social affective experience that has been lacking in the field of autism research and in many neuroethological studies of visual perception in general: a measure of not only what someone is looking at but of how engaged he or she is with what he or she is looking at. Although previous work has shown that children with ASD allocate fewer attentional resources to socially relevant stimuli than their typically developing peers, these studies have failed to capture how engaged children are with what they are fixating on.

Further, measures of blink inhibition are well suited to providing temporally precise indices of perceived stimulus salience during naturalistic, fast-paced presentations of visual content. In comparison to other autonomic responses traditionally used in psychophysiological studies, such as electrodermal and cardiovascular activity, blink inhibition compares well for measuring reactivity to emotional stimuli: electrodermal and cardiovascular responses are highly multi-determined, preventing strong inferences about their relationship to mental activity; in addition, their latency and refractory periods undermine precise temporal markings of their measurements relative to affective or cognitive state. Blink inhibition, in contrast, is intrinsic to the visual system rather than a peripheral function; its on- and off-set parameters are precise and temporally sensitive to ecologically valid, fast-paced presentations of content; and, finally, blink inhibition can be measured by entirely noninvasive, even concealed, eye-tracking cameras, or other devices, circumventing the need for obtrusive equipment that would alter the ethological validity of other measures.

In one embodiment, the present systems and methods provide a mechanism to assess viewer behavior, features of stimuli, and the interaction between viewer behavior and stimuli. Specifically and according to one aspect, because blinking interrupts the flow of visual information to a viewer, and because the inhibition of blinking ensures that the flow of visual information will not be disrupted, measurements of the precise timing of when individuals do or do not inhibit their blinking can provide robust quantitative indices of viewer engagement and the subjective assessment of perceived stimulus salience, even though individuals are largely unaware of their own blinking during everyday situations. Therefore, the systems and methods described herein for quantifying blink response and blink inhibition provide moment-by-moments measurements of viewer engagement by measuring what is or is not engaging enough to warrant viewers' inhibition of blinking.

One embodiment of the present disclosure describes measures of visual scanning, eye movements, blink data, and blink timing data to derive a measure of how engaged a person is with what he or she is looking at. In one aspect, blink related data as a measure of viewer engagement provides a mechanism for determining the most engaging spatial and temporal aspects of a stimulus. According to another aspect, measures of blink inhibition provide a promising index of autonomic reactivity and differential engagement, time-locked to salient moments within fast-paced, rapidly changing visual displays. By precisely measuring the timing of blink inhibition relative to unfolding content, one can determine, on a moment-by-moment basis, a viewer's subjective assessment of the importance of what he or she is watching.

Accordingly, it will be understood that various embodiments of the present system described herein are generally implemented as a special purpose or general-purpose computer including various computer hardware as discussed in greater detail below. Embodiments within the scope of the present disclosure also include computer-readable media for carrying or having computer-executable instructions or data structures stored thereon. Such computer-readable media can be any available media which can be accessed by a general purpose or special purpose computer, or downloadable through communication networks. By way of example, and not limitation, such computer-readable media can comprise physical storage media such as RAM, ROM, flash memory, EEPROM, CD-ROM, DVD, or other optical disk storage, magnetic disk storage or other magnetic storage devices, any type of removable non-volatile memories such as secure digital (SD), flash memory, memory stick etc., or any other medium which can be used to carry or store computer program code in the form of computer-executable instructions or data structures and which can be accessed by a general purpose or special purpose computer, or a mobile device.

When information is transferred or provided over a network or another communications connection (either hardwired, wireless, or a combination of hardwired or wireless) to a computer, the computer properly views the connection as a computer-readable medium. Thus, any such a connection is properly termed and considered a computer-readable medium. Combinations of the above should also be included within the scope of computer-readable media. Computer-executable instructions comprise, for example, instructions and data which cause a general purpose computer, special purpose computer, or special purpose processing device such as a mobile device processor to perform one specific function or a group of functions.

Those skilled in the art will understand the features and aspects of a suitable computing environment in which aspects of the disclosure may be implemented. Although not required, the inventions are described in the general context of computer-executable instructions, such as program modules or engines, as described earlier, being executed by computers in networked environments. Such program modules are often reflected and illustrated by flow charts, sequence diagrams, exemplary screen displays, and other techniques used by those skilled in the art to communicate how to make and use such computer program modules. Generally, program modules include routines, programs, objects, components, data structures, etc. that perform particular tasks or implement particular abstract data types, within the computer. Computer-executable instructions, associated data structures, and program modules represent examples of the program code for executing steps of the methods disclosed herein. The particular sequence of such executable instructions or associated data structures represent examples of corresponding acts for implementing the functions described in such steps.

Those skilled in the art will also appreciate that the invention may be practiced in network computing environments with many types of computer system configurations, including personal computers, hand-held devices, multi-processor systems, microprocessor-based or programmable consumer electronics, networked PCs, minicomputers, mainframe computers, and the like. The invention is practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the inventions, which is not illustrated, includes a general purpose computing device in the form of a conventional computer, including a processing unit, a system memory, and a system bus that couples various system components including the system memory to the processing unit. The computer will typically include one or more magnetic hard disk drives (also called "data stores" or "data storage" or other names) for reading from and writing to. The drives and their associated computer-readable media provide nonvolatile storage of computer-executable instructions, data structures, program modules, and other data for the computer. Although the exemplary environment described herein employs a magnetic hard disk, a removable magnetic disk, removable optical disks, other types of computer readable media for storing data can be used, including magnetic cassettes, flash memory cards, digital video disks (DVDs), Bernoulli cartridges, RAMs, ROMs, and the like.

Computer program code that implements most of the functionality described herein typically comprises one or more program modules may be stored on the hard disk or other storage medium. This program code, as is known to those skilled in the art, usually includes an operating system, one or more application programs, other program modules, and program data. A user may enter commands and information into the computer through keyboard, pointing device, a script containing computer program code written in a scripting language or other input devices (not shown), such as a microphone, etc. These and other input devices are often connected to the processing unit through known electrical, optical, or wireless connections.

The main computer that effects many aspects of the inventions will typically operate in a networked environment using logical connections to one or more remote computers or data sources, which are described further below. Remote computers may be another personal computer, a server, a router, a network PC, a peer device or other common network node, and typically include many or all of the elements described above relative to the main computer system in which the inventions are embodied. The logical connections between computers include a local area network (LAN), a wide area network (WAN), and wireless LANs (WLAN) that are presented here by way of example and not limitation. Such networking environments are commonplace in office-wide or enterprise-wide computer networks, intranets and the Internet.

When used in a LAN or WLAN networking environment, the main computer system implementing aspects of the invention is connected to the local network through a network interface or adapter. When used in a WAN or WLAN networking environment, the computer may include a modem, a wireless link, or other mechanisms for establishing communications over the wide area network, such as the Internet. In a networked environment, program modules depicted relative to the computer, or portions thereof, may be stored in a remote memory storage device. It will be appreciated that the network connections described or shown are exemplary and other mechanisms of establishing communications over wide area networks or the Internet may be used.

In view of the foregoing detailed description of preferred embodiments of the present invention, it readily will be understood by those persons skilled in the art that the present invention is susceptible to broad utility and application. While various aspects have been described in the context of a preferred embodiment, additional aspects, features, and methodologies of the present invention will be readily discernible from the description herein, by those of ordinary skill in the art. Many embodiments and adaptations of the present invention other than those herein described, as well as many variations, modifications, and equivalent arrangements and methodologies, will be apparent from or reasonably suggested by the present invention and the foregoing description thereof, without departing from the substance or scope of the present invention. Furthermore, any sequence(s) and/or temporal order of steps of various processes described and claimed herein are those considered to be the best mode contemplated for carrying out the present invention. It should also be understood that, although steps of various processes may be shown and described as being in a preferred sequence or temporal order, the steps of any such processes are not limited to being carried out in any particular sequence or order, absent a specific indication of such to achieve a particular intended result. In most cases, the steps of such processes may be carried out in a variety of different sequences and orders, while still falling within the scope of the present inventions. In addition, some steps may be carried out simultaneously.

The embodiments were chosen and described in order to explain the principles of the inventions and their practical application so as to enable others skilled in the art to utilize the inventions and various embodiments and with various modifications as are suited to the particular use contemplated. Alternative embodiments will become apparent to those skilled in the art to which the present inventions pertain without departing from their spirit and scope. Accordingly, the scope of the present inventions is defined by the appended claims rather than the foregoing description and the exemplary embodiments described therein.

What is claimed is:

1. A method for assessing the risk of a mental condition in an individual using an eye monitoring device, comprising the steps of:
   receiving blink data indicative of the individual's blink responses to a dynamic visual stimulus displayed to the individual, wherein the blink data is collected via the eye monitoring device;
   synchronizing, via software executing on a processor, the received blink data with the dynamic visual stimulus;
   identifying, via software executing on the processor, a pattern of blink inhibition in the synchronized blink data;
   retrieving, via software executing on the processor, event data related to the dynamic visual stimulus from a database; and
   comparing, via software executing on the processor, a parameter of the pattern of blink inhibition in the synchronized blink data with a parameter of the event data related to the dynamic visual stimulus to determine at least one delta parameter, wherein the at least one delta parameter indicates a likelihood that the individual has a mental disorder.

2. The method of claim 1, wherein the parameter of the event data comprises a predetermined time-stamped event.

3. The method of claim 1, wherein the parameter of the event data comprises a time value.

4. The method of claim 1, wherein the parameter of the pattern of blink inhibition comprises a time value.

5. The method of claim 1, wherein the at least one delta parameter comprises a time value that exceeds a predetermined threshold value.

6. The method of claim 1, wherein the at least one delta parameter comprises a time value that is less than a predetermined threshold value.

7. The method of claim 1, further comprising the step of providing a diagnosis to the individual based on the at least one delta parameter.

8. The method of claim 1, wherein the mental condition comprises a developmental or cognitive disorder.

9. The method of claim 1, wherein the event data corresponds to one or more of the following: physical events within the dynamic visual stimulus, affective events within the dynamic visual stimulus, events presumed to cause or inhibit blinking based on the dynamic visual stimulus.

10. The method of claim 1, wherein the step of synchronizing comprises time-locking or time-correlating the received blink data with the dynamic visual stimulus.

11. The method of claim 1, wherein the pattern of blink inhibition comprises a comparison between the individual's blink data and a chance probability of blinking associated with the individual.

12. The method of claim 1, wherein the pattern of blink inhibition comprises a mean blink rate for the individual during the dynamic visual stimulus.

13. The method of claim 1, wherein the pattern of blink inhibition comprises a moment-by-moment blink rate for the individual.

14. The method of claim 1, wherein the pattern of blink inhibition comprises a measure of an instantaneous blink rate for the individual at a certain time point as compared to a mean blink rate for the individual.

15. The method of claim 1, wherein the pattern of blink inhibition comprises a measure of an instantaneous blink rate for the individual at a certain time point as compared to a mean blink rate for a control group.

16. The method of claim 1, wherein the pattern of blink inhibition comprises a measure of an instantaneous blink rate for the individual as compared to measure of variance in a mean blink rate for the individual.

17. A system for assessing the risk of a mental condition in an individual using an eye monitoring device, comprising:
a processor;
software executing on the processor for receiving blink data indicative of the individual's blink responses to a dynamic visual stimulus displayed to the individual, wherein the blink data is collected via the eye monitoring device;
software executing on the processor for synchronizing the received blink data with the dynamic visual stimulus;
software executing on the processor for identifying a pattern of blink inhibition in the synchronized blink data;
software executing on the processor for retrieving event data related to the dynamic visual stimulus from a database; and
software executing on the processor for comparing a parameter of the pattern of blink inhibition in the synchronized blink data with a parameter of the event data related to the dynamic visual stimulus to determine at least one delta parameter, wherein the at least one delta parameter indicates a likelihood that the individual has a mental disorder.

18. The system of claim 17, wherein the parameter of the event data comprises a predetermined time-stamped event.

19. The system of claim 17, wherein the parameter of the event data comprises a time value.

20. The system of claim 17, wherein the parameter of the pattern of blink inhibition comprises a time value.

21. The system of claim 17, wherein the at least one delta parameter comprises a time value that exceeds a predetermined threshold value.

22. The system of claim 17, wherein the at least one delta parameter comprises a time value that is less than a predetermined threshold value.

23. The system of claim 17, further comprising software executing on the processor for providing a diagnosis to the individual based on the at least one delta parameter.

24. The system of claim 17, wherein the mental condition comprises a developmental or cognitive disorder.

25. The system of claim 17, wherein the event data corresponds to one or more of the following: physical events within the dynamic visual stimulus, affective events within the dynamic visual stimulus, events presumed to cause or inhibit blinking based on the dynamic visual stimulus.

26. The system of claim 17, wherein the software for synchronizing further comprises software executing on the processor for time-locking or time-correlating the received blink data with the dynamic visual stimulus.

27. The system of claim 17, wherein the pattern of blink inhibition comprises a comparison between the individual's blink data and a chance probability of blinking associated with the individual.

28. The system of claim 17, wherein the pattern of blink inhibition comprises a mean blink rate for the individual during the dynamic visual stimulus.

29. The system of claim 17, wherein the pattern of blink inhibition comprises a moment-by-moment blink rate for the individual.

30. The system of claim 17, wherein the pattern of blink inhibition comprises a measure of an instantaneous blink rate for the individual at a certain time point as compared to a mean blink rate for the individual.

31. The system of claim 17, wherein the pattern of blink inhibition comprises a measure of an instantaneous blink rate for the individual at a certain time point as compared to a mean blink rate for a control group.

32. The system of claim 17, wherein the pattern of blink inhibition comprises a measure of an instantaneous blink rate for the individual as compared to measure of variance in a mean blink rate for the individual.

33. A method for evaluating, monitoring, or diagnosing a mental condition in an individual using an eye monitoring device, comprising the steps of:
receiving blink data indicative of the individual's blink responses to a dynamic visual stimulus displayed to the individual, wherein the blink data is collected using the eye monitoring device;
synchronizing, via software executing on a processor, the received blink data with the dynamic visual stimulus;
identifying, via software executing on the processor, a pattern of blink inhibition in the synchronized blink data;
retrieving, via software executing on the processor, a control pattern of blink inhibition for the dynamic visual stimulus displayed to the individual from a database; and comparing, via software executing on the processor, the pattern of blink inhibition in the synchronized blink data with the control pattern of blink inhibition to determine whether the pattern of blink inhibition falls outside a range of the control pattern of blink inhibition and thereby indicates a likelihood that the individual has a mental condition.

34. The method of claim 33, wherein the mental condition comprises a developmental or cognitive disorder.

35. The method of claim 33, wherein the step of synchronizing comprises time-locking or time-correlating the received blink data with the dynamic visual stimulus.

36. The method of claim 33, wherein the blink data for the individual corresponds to a rate of change of pupil size for the individual.

37. The method of claim 33, wherein the blink data corresponds to eyelid closure for the individual.

38. The method of claim 33, further comprising the step of converting, via software executing on the processor, the blink data to binary format for identification purposes.

39. The method of claim 33, wherein the control pattern of blink inhibition comprises an average blink rate for a plurality of individuals in response to the dynamic visual stimulus.

40. The method of claim 33, wherein the control pattern of blink inhibition comprises a probability distribution of average blink rates for a plurality of individuals as obtained by permuting the blink data of the plurality of individuals.

41. The method of claim 40, wherein the step of permuting the data of the plurality of individuals comprises circular shifting with respect to an original timing of blink data collection.

42. The method of claim 40, wherein the step of permuting the data of the plurality of individuals comprises randomizing an order of blinks and inter-blink intervals for each individual.

43. The method of claim 33, wherein the pattern of blink inhibition comprises a mean blink rate for the individual during the dynamic visual stimulus.

44. The method of claim 33, wherein the pattern of blink inhibition comprises a moment-by-moment blink rate for the individual.

45. The method of claim 33, wherein the pattern of blink inhibition comprises a measure of an instantaneous blink rate for the individual at a certain time point and the control pattern of blink inhibition comprises an instantaneous blink rate for a control group.

46. The method of claim 33, wherein the control pattern of blink inhibition comprises an average blink rate for the individual when no dynamic visual stimulus is present.

47. The method of claim 33, wherein the pattern of blink inhibition comprises a measure of blink inhibition relative to an event in the dynamic visual stimulus.

48. The method of claim 47, wherein the event in the dynamic visual stimulus comprises a physical event or an affective event.

49. The method of claim 33, wherein the control pattern of blink inhibition indicates a severity of the mental condition.

50. A system for evaluating, monitoring, or diagnosing a mental condition in an individual using an eye monitoring device, comprising:
a processor;
software executing on the processor for receiving blink data indicative of the individual's blink responses to a dynamic visual stimulus displayed to the individual, wherein the blink data is collected using the eye monitoring device;
software executing on the processor for synchronizing the received blink data with the dynamic visual stimulus;
software executing on the processor for identifying a pattern of blink inhibition in the synchronized blink data;
software executing on the processor for retrieving a control pattern of blink inhibition for the dynamic visual stimulus displayed to the individual from a database; and
software executing on the processor for comparing the pattern of blink inhibition in the synchronized blink data with the control pattern of blink inhibition to determine whether the pattern of blink inhibition falls outside a range of the control pattern of blink inhibition and thereby indicates a likelihood that the individual has a mental condition.

51. The system of claim 50, wherein the mental condition comprises a developmental or cognitive disorder.

52. The system of claim 50, wherein the software for synchronizing further comprises software executing on the processor for time-locking or time-correlating the received blink data with the dynamic visual stimulus.

53. The system of claim 50, wherein the blink data for the individual corresponds to a rate of change of pupil size for the individual.

54. The system of claim 50, wherein the blink data corresponds to eyelid closure for the individual.

55. The system of claim 50, further comprising software executing on the processor for converting the blink data to binary format for identification purposes.

56. The system of claim 50, wherein the control pattern of blink inhibition comprises an average blink rate for a plurality of individuals in response to the dynamic visual stimulus.

57. The system of claim 50, wherein the control pattern of blink inhibition comprises a probability distribution of average blink rates for a plurality of individuals as obtained by permuting the blink data of the plurality of individuals.

58. The system of claim 57, wherein the step of permuting the data of the plurality of individuals comprises circular shifting with respect to an original timing of blink data collection.

59. The system of claim 57, wherein the step of permuting the data of the plurality of individuals comprises randomizing an order of blinks and inter-blink intervals for each individual.

60. The system of claim 50, wherein the pattern of blink inhibition comprises a mean blink rate for the individual during the dynamic visual stimulus.

61. The system of claim 50, wherein the pattern of blink inhibition comprises a moment-by-moment blink rate for the individual.

62. The system of claim 50, wherein the pattern of blink inhibition comprises a measure of an instantaneous blink rate for the individual at a certain time point and the control pattern of blink inhibition comprises an instantaneous blink rate for a control group.

63. The system of claim 50, wherein the control pattern of blink inhibition comprises an average blink rate for the individual when no dynamic visual stimulus is present.

64. The system of claim 50, wherein the pattern of blink inhibition comprises a measure of blink inhibition relative to an event in the dynamic visual stimulus.

65. The system of claim 64, wherein the event in the dynamic visual stimulus comprises a physical event or an affective event.

66. The system of claim 50, wherein the control pattern of blink inhibition indicates a severity of the mental condition.

\* \* \* \* \*